US009133258B2

(12) United States Patent
Wang et al.

(10) Patent No.: US 9,133,258 B2
(45) Date of Patent: Sep. 15, 2015

(54) MYOMEGALIN VARIANT 8

(75) Inventors: Zhe Wang, Hong Kong (CN); Robert Zhong Qi, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 0 days.

(21) Appl. No.: 13/825,945

(22) PCT Filed: Nov. 15, 2011

(86) PCT No.: PCT/CN2011/001907

§ 371 (c)(1), (2), (4) Date: May 20, 2013

(87) PCT Pub. No.: WO2012/065362

PCT Pub. Date: May 24, 2012

(65) Prior Publication Data

US 2013/0230532 A1 Sep. 5, 2013

Related U.S. Application Data

(60) Provisional application No. 61/344,927, filed on Nov. 19, 2010.

(51) Int. Cl.

| | |
|---|---|
| ***C07H 21/04*** | (2006.01) |
| ***A61K 38/00*** | (2006.01) |
| ***A61K 38/43*** | (2006.01) |
| ***C12P 21/06*** | (2006.01) |
| ***C07K 14/47*** | (2006.01) |
| ***G01N 33/68*** | (2006.01) |
| ***C12Q 1/68*** | (2006.01) |
| ***C07K 16/18*** | (2006.01) |
| ***C12N 15/113*** | (2010.01) |

(52) U.S. Cl.

CPC ............. *C07K 14/47* (2013.01); *C07K 14/4716* (2013.01); *C07K 16/18* (2013.01); *C12N 15/113* (2013.01); *C12Q 1/6876* (2013.01); *G01N 33/6887* (2013.01); *G01N 33/6893* (2013.01); *A61K 38/00* (2013.01); *C12N 2310/14* (2013.01); *G01N 2500/00* (2013.01)

(58) Field of Classification Search

CPC . C12N 15/52; C07K 14/4716; A61K 38/1719

See application file for complete search history.

(56) References Cited

U.S. PATENT DOCUMENTS

2007/0083334 A1* 4/2007 Mintz et al. ..................... 702/19

OTHER PUBLICATIONS

Mickle, J.E., et al. Genotype-phenotype relationships in cystic fibrosis. Med. Clin. N. Am., 2000, vol. 83, No. 3, p. 597-607.*

Wells, J.A. Additivity of mutational effects in proteins. Biochemistry, 1990, vol. 29, No. 37, p. 8509-8517.*

Database GenBank Accession No. CAH92060. Bloecker, H. "hypothetical protein [*Pongo abelii*]". May 1, 2008.

Database GenBank Accession No. CR859904. Bloecker, H. "*Pongo abelii* mRNA; cDNA DKFZp469C1614 (from clone DKFZp469C1614)". May 1, 2008.

Honnappa, S. et al. "An EB1-Binding Motif Acts as a Microtubule Tip Localization Signal" *Cell*, Jul. 24, 2009, 138:366-376.

International Search Report in International Application No. PCT/CN2011/001907, filed Nov. 15, 2011.

* cited by examiner

*Primary Examiner* — Robert Landsman

*Assistant Examiner* — Bruce D Hissong

(74) *Attorney, Agent, or Firm* — Saliwanchik, Lloyd & Eisenschenk

(57) ABSTRACT

The present invention provides a novel myomegalin isoform—myomegalin variant 8 (MMG8). The myomegalin variant 8 regulates microtubule organization at the Golgi apparatus, protein modification, secretion and trafficking, and cell proliferation. The present invention also provides nucleic acid molecules encoding the myomegalin isoforms, and vectors and host cells containing the nucleic acid molecules. Also provided are fusion constructs comprising the myomegalin isoform and antibodies that bind specifically to the myomegalin isoforms of the present invention. The present invention further provides uses of the myomegalin isoform as a diagnostic biomarker and as a target for screening for therapeutics for diseases such as cancer, diabetes, and lysosomal storage diseases.

7 Claims, 8 Drawing Sheets

SEQUENCE LISTING

```
<160> NUMBER OF SEQ ID NOS: 39

<210> SEQ ID NO 1
<211> LENGTH: 3351
<212> TYPE: DNA
<213> ORGANISM: Homo sapiens

<400> SEQUENCE: 1

atgaaggaga tttgcaggat ctgtgcccga gagctgtgtg gaaaccagcg gcgctggatc      60

ttccacacgg cgtccaagct caatctccag gttctgcttt cgcacgtctt gggcaaggat     120

gtccccccgcg atggcaaagc cgagttcgct tgcagcaagt gtgctttcat gcttgatcga    180

atctatcgat tcgacacagt tattgcccgg attgaagcgc tttctattga gcgcttgcaa     240

aagctgctac tggagaagga tcgcctcaag ttctgcattg ccagtatgta tcggaagaat     300
```

```
aacgatgact ctggcgcgga gatcaaggcg gggaatggga cggttgacat gtccgtctta    360
cccgatgcga gatactctgc actgctccag gaggacttcg cctattcagg gtttgagtgc    420
tgggtggaga atgaggatca gatccaggag ccacacagct gccatggttc agaaggccct    480
ggaaaccgac ccaggagatg ccgtggttgt gccgctttgc gggttgctga ttctgactat    540
gaagccattt gtaaggtacc tcgaaaggtg gccagaagta tctcctgcgg cccttctagc    600
aggtggtcga ccagcatttg cactgaagaa ccagcgttgt ctgaggttgg gccacccgac    660
ttagcaagca caaaggtacc cccagatgga gaaagcatgg aggaagagac gcctggttcc    720
tctgtggaat ctttggatgc aagcgtccag gctagccctc cacaacagaa agatgaggag    780
actgagagaa gtgcaaagga acttggaaag tgtgactgtt gttcagatga tcaggctccg    840
cagcatgggt gtaatcacaa gctggaatta gctcttagca tgattaaagg tcttgattat    900
aagcccatcc agagcccccg agggagcagg cttccgattc cagtgaaatc cagcctacct    960
ggagccaagc ctggccctag catgacagat ggagttagtt ccggtttcct taacaggtct   1020
ttgaaacccc tttacaagac acctgtgagt tatcccttgg agctttcaga cctgcaggag   1080
ctgtgggatg atctctgtga agattatttg ccgctccggg tccagcccat gactgaagag   1140
ttgctgaaac aacaaaagct gaattcacat gagaccacta taactcagca gtctgtatct   1200
gattcccact tggcagaact ccaggaaaaa atccagcaaa cagaggccac caacaagatt   1260
cttcaagaga aacttaatga aatgagctat gaactaaagt gtgctcagga gtcgtctcaa   1320
aagcaagatg gtacaattca gaacctcaag gaaactctga aaagcaggga acgtgagact   1380
gaggagttgt accaggtaat tgaaggtcaa aatgacacaa tggcaaagct tcgagaaatg   1440
ctgcaccaaa gccagcttgg acaacttcac agctcagagg gtacttctcc agctcagcaa   1500
caggtagctc tgcttgatct tcagagtgct ttattctgca gccaacttga aatacagaag   1560
ctccagaggg tggtacgaca gaaagagcgc caactggctg atgccaaaca atgtgtgcaa   1620
tttgtagagg ctgcagcaca cgagagtgaa cagcagaaag aggcttcttg gaaacataac   1680
caggaattgc gaaaagcctt gcagcagcta caagaagaat tgcagaataa gagccaacag   1740
cttcgtgcct gggaggctga aaaatacaat gagattcgaa cccaggaaca aaacatccag   1800
cacctaaacc atagtctgag tcacaaggag cagttgcttc aggaatttcg ggagctccta   1860
cagtatcgag ataactcaga caaaaccctt gaagcaaatg aaatgttgct tgagaaactt   1920
cgccagcgaa tacatgataa agctgttgct ctggagcggg ctatagatga aaaattctct   1980
gctctagaag agaaagaaaa agaactgcgc cagcttcgtc ttgctgtgag agagcgagat   2040
catgacttag agagactgcg cgatgtcctc tcctccaatg aagctactat gcaaagtatg   2100
gagagtctcc tgagggccaa aggcctggaa gtggaacagt tatctactac ctgtcaaaac   2160
ctccagtggc tgaaagaaga aatggaaacc aaatttagcc gttggcagaa ggaacaagag   2220
agtatcattc agcagttaca gacgtctctt catgatagga acaaagaagt ggaggatctt   2280
agtgcaacac tgctctgcaa acttggacca gggcagagtg agatagcaga ggagctgtgc   2340
cagcgtctac agcgaaagga aaggatgctg caggaccttc taagtgatcg aaataaacaa   2400
gtgctggaac atgaaatgga gattcaaggc ctgcttcagt ctgtgagcac cagggagcag   2460
gaaagccaag ctgctgcaga gaagttggtg caagccttaa tggaaagaaa ttcagaatta   2520
caggccctgc gccaatattt aggagggaga gactccctga tgtcccaagc acccatctct   2580
aaccaacaag ctgaagttac cccccactggc tgtcttggaa aacagactga tcaaggttca   2640
atgcagatac cttccagaga tgatagcact tcattgactg ccaaagagga tgtcagcata   2700
```

```
cccagatcca cattaggaga cttggacaca gttgcagggc tggaaaaaga actgagtaat   2760

gccaaagagg aacttgaact catggctaaa aaagaaagag aaagtcagat ggaactttct   2820

gctctacagt ccatgatggc tgtgcaggaa gaagagctgc aggtgcaggc tgctgatatg   2880

gagtctctga ccaggaacat acagattaaa gaagatctca taaaggacct gcaaatgcaa   2940

ctggttgatc ctgaagacat accagctatg gaacgcctga cccaggaagt cttacttctt   3000

cgggaaaaag ttgcttcagt agaatcccag ggtcaagaaa tttcaggaaa ccgaagacaa   3060

cagttgctgc tgatgctaga aggactagta gatgaacgga gtcggctcaa tgaggcctta   3120

caagcagaga gacagctcta tagcagtctg gtgaagttcc atgcccatcc agagagctct   3180

gagagagacc gaactctgca ggtggaactg gaaggggctc aggtgttacg cagtcggcta   3240

gaagaagttc ttggaagaag cttggagcgc ttaaacaggc tggagaccct ggccgccatt   3300

ggaggtgggg aactggaaag tgtgcgaatt catcacaagc atgcctactg a            3351
```

```
<210> SEQ ID NO 2
<211> LENGTH: 1116
<212> TYPE: PRT
<213> ORGANISM: Homo sapiens

<400> SEQUENCE: 2

Met Lys Glu Ile Cys Arg Ile Cys Ala Arg Glu Leu Cys Gly Asn Gln
1               5                   10                  15

Arg Arg Trp Ile Phe His Thr Ala Ser Lys Leu Asn Leu Gln Val Leu
            20                  25                  30

Leu Ser His Val Leu Gly Lys Asp Val Pro Arg Asp Gly Lys Ala Glu
        35                  40                  45

Phe Ala Cys Ser Lys Cys Ala Phe Met Leu Asp Arg Ile Tyr Arg Phe
    50                  55                  60

Asp Thr Val Ile Ala Arg Ile Glu Ala Leu Ser Ile Glu Arg Leu Gln
65                  70                  75                  80

Lys Leu Leu Leu Glu Lys Asp Arg Leu Lys Phe Cys Ile Ala Ser Met
                85                  90                  95

Tyr Arg Lys Asn Asn Asp Asp Ser Gly Ala Glu Ile Lys Ala Gly Asn
            100                 105                 110

Gly Thr Val Asp Met Ser Val Leu Pro Asp Ala Arg Tyr Ser Ala Leu
        115                 120                 125

Leu Gln Glu Asp Phe Ala Tyr Ser Gly Phe Glu Cys Trp Val Glu Asn
    130                 135                 140

Glu Asp Gln Ile Gln Glu Pro His Ser Cys His Gly Ser Glu Gly Pro
145                 150                 155                 160

Gly Asn Arg Pro Arg Arg Cys Arg Gly Cys Ala Ala Leu Arg Val Ala
                165                 170                 175

Asp Ser Asp Tyr Glu Ala Ile Cys Lys Val Pro Arg Lys Val Ala Arg
            180                 185                 190

Ser Ile Ser Cys Gly Pro Ser Ser Arg Trp Ser Thr Ser Ile Cys Thr
        195                 200                 205

Glu Glu Pro Ala Leu Ser Glu Val Gly Pro Pro Asp Leu Ala Ser Thr
    210                 215                 220

Lys Val Pro Pro Asp Gly Glu Ser Met Glu Glu Glu Thr Pro Gly Ser
225                 230                 235                 240

Ser Val Glu Ser Leu Asp Ala Ser Val Gln Ala Ser Pro Pro Gln Gln
                245                 250                 255
```

```
Lys Asp Glu Glu Thr Glu Arg Ser Ala Lys Glu Leu Gly Lys Cys Asp
            260                 265                 270

Cys Cys Ser Asp Asp Gln Ala Pro Gln His Gly Cys Asn His Lys Leu
        275                 280                 285

Glu Leu Ala Leu Ser Met Ile Lys Gly Leu Asp Tyr Lys Pro Ile Gln
    290                 295                 300

Ser Pro Arg Gly Ser Arg Leu Pro Ile Pro Val Lys Ser Ser Leu Pro
305                 310                 315                 320

Gly Ala Lys Pro Gly Pro Ser Met Thr Asp Gly Val Ser Ser Gly Phe
                325                 330                 335

Leu Asn Arg Ser Leu Lys Pro Leu Tyr Lys Thr Pro Val Ser Tyr Pro
            340                 345                 350

Leu Glu Leu Ser Asp Leu Gln Glu Leu Trp Asp Asp Leu Cys Glu Asp
        355                 360                 365

Tyr Leu Pro Leu Arg Val Gln Pro Met Thr Glu Glu Leu Leu Lys Gln
    370                 375                 380

Gln Lys Leu Asn Ser His Glu Thr Thr Ile Thr Gln Gln Ser Val Ser
385                 390                 395                 400

Asp Ser His Leu Ala Glu Leu Gln Glu Lys Ile Gln Gln Thr Glu Ala
                405                 410                 415

Thr Asn Lys Ile Leu Gln Glu Lys Leu Asn Glu Met Ser Tyr Glu Leu
            420                 425                 430

Lys Cys Ala Gln Glu Ser Ser Gln Lys Gln Asp Gly Thr Ile Gln Asn
        435                 440                 445

Leu Lys Glu Thr Leu Lys Ser Arg Glu Arg Glu Thr Glu Glu Leu Tyr
    450                 455                 460

Gln Val Ile Glu Gly Gln Asn Asp Thr Met Ala Lys Leu Arg Glu Met
465                 470                 475                 480

Leu His Gln Ser Gln Leu Gly Gln Leu His Ser Ser Glu Gly Thr Ser
                485                 490                 495

Pro Ala Gln Gln Gln Val Ala Leu Leu Asp Leu Gln Ser Ala Leu Phe
            500                 505                 510

Cys Ser Gln Leu Glu Ile Gln Lys Leu Gln Arg Val Val Arg Gln Lys
        515                 520                 525

Glu Arg Gln Leu Ala Asp Ala Lys Gln Cys Val Gln Phe Val Glu Ala
    530                 535                 540

Ala Ala His Glu Ser Glu Gln Gln Lys Glu Ala Ser Trp Lys His Asn
545                 550                 555                 560

Gln Glu Leu Arg Lys Ala Leu Gln Gln Leu Gln Glu Glu Leu Gln Asn
                565                 570                 575

Lys Ser Gln Gln Leu Arg Ala Trp Glu Ala Glu Lys Tyr Asn Glu Ile
            580                 585                 590

Arg Thr Gln Glu Gln Asn Ile Gln His Leu Asn His Ser Leu Ser His
        595                 600                 605

Lys Glu Gln Leu Leu Gln Glu Phe Arg Glu Leu Leu Gln Tyr Arg Asp
    610                 615                 620

Asn Ser Asp Lys Thr Leu Glu Ala Asn Glu Met Leu Leu Glu Lys Leu
625                 630                 635                 640

Arg Gln Arg Ile His Asp Lys Ala Val Ala Leu Glu Arg Ala Ile Asp
                645                 650                 655

Glu Lys Phe Ser Ala Leu Glu Glu Lys Glu Lys Glu Leu Arg Gln Leu
            660                 665                 670

Arg Leu Ala Val Arg Glu Arg Asp His Asp Leu Glu Arg Leu Arg Asp
```

-continued

```
        675                 680                 685

Val Leu Ser Ser Asn Glu Ala Thr Met Gln Ser Met Glu Ser Leu Leu
    690                 695                 700

Arg Ala Lys Gly Leu Glu Val Glu Gln Leu Ser Thr Thr Cys Gln Asn
705                 710                 715                 720

Leu Gln Trp Leu Lys Glu Glu Met Glu Thr Lys Phe Ser Arg Trp Gln
                725                 730                 735

Lys Glu Gln Glu Ser Ile Ile Gln Gln Leu Gln Thr Ser Leu His Asp
            740                 745                 750

Arg Asn Lys Glu Val Glu Asp Leu Ser Ala Thr Leu Leu Cys Lys Leu
        755                 760                 765

Gly Pro Gly Gln Ser Glu Ile Ala Glu Glu Leu Cys Gln Arg Leu Gln
    770                 775                 780

Arg Lys Glu Arg Met Leu Gln Asp Leu Leu Ser Asp Arg Asn Lys Gln
785                 790                 795                 800

Val Leu Glu His Glu Met Glu Ile Gln Gly Leu Leu Gln Ser Val Ser
                805                 810                 815

Thr Arg Glu Gln Glu Ser Gln Ala Ala Ala Glu Lys Leu Val Gln Ala
            820                 825                 830

Leu Met Glu Arg Asn Ser Glu Leu Gln Ala Leu Arg Gln Tyr Leu Gly
        835                 840                 845

Gly Arg Asp Ser Leu Met Ser Gln Ala Pro Ile Ser Asn Gln Gln Ala
    850                 855                 860

Glu Val Thr Pro Thr Gly Arg Leu Gly Lys Gln Thr Asp Gln Gly Ser
865                 870                 875                 880

Met Gln Ile Pro Ser Arg Asp Asp Ser Thr Ser Leu Thr Ala Lys Glu
                885                 890                 895

Asp Val Ser Ile Pro Arg Ser Thr Leu Gly Asp Leu Asp Thr Val Ala
            900                 905                 910

Gly Leu Glu Lys Glu Leu Ser Asn Ala Lys Glu Glu Leu Glu Leu Met
        915                 920                 925

Ala Lys Lys Glu Arg Glu Ser Gln Met Glu Leu Ser Ala Leu Gln Ser
    930                 935                 940

Met Met Ala Val Gln Glu Glu Glu Leu Gln Val Gln Ala Ala Asp Met
945                 950                 955                 960

Glu Ser Leu Thr Arg Asn Ile Gln Ile Lys Glu Asp Leu Ile Lys Asp
                965                 970                 975

Leu Gln Met Gln Leu Val Asp Pro Glu Asp Ile Pro Ala Met Glu Arg
            980                 985                 990

Leu Thr Gln Glu Val Leu Leu Leu  Arg Glu Lys Val Ala  Ser Val Glu
        995                 1000                1005

Ser Gln  Gly Gln Glu Ile Ser  Gly Asn Arg Arg Gln  Gln Leu Leu
    1010                1015                1020

Leu Met  Leu Glu Gly Leu Val  Asp Glu Arg Ser Arg  Leu Asn Glu
    1025                1030                1035

Ala Leu  Gln Ala Glu Arg Gln  Leu Tyr Ser Ser Leu  Val Lys Phe
    1040                1045                1050

His Ala  His Pro Glu Ser Ser  Glu Arg Asp Arg Thr  Leu Gln Val
    1055                1060                1065

Glu Leu  Glu Gly Ala Gln Val  Leu Arg Ser Arg Leu  Glu Glu Val
    1070                1075                1080

Leu Gly  Arg Ser Leu Glu Arg  Leu Asn Arg Leu Glu  Thr Leu Ala
    1085                1090                1095
```

```
Ala Ile  Gly Gly Gly Glu Leu  Glu Ser Val Arg Ile  His His Lys
    1100                 1105                 1110

His Ala  Tyr
    1115


<210> SEQ ID NO 3
<211> LENGTH: 2346
<212> TYPE: PRT
<213> ORGANISM: Homo sapiens

<400> SEQUENCE: 3

Met Ser Asn Gly Tyr Arg Thr Leu Ser Gln His Leu Asn Asp Leu Lys
1               5                   10                  15

Lys Glu Asn Phe Ser Leu Lys Leu Arg Ile Tyr Phe Leu Glu Glu Arg
            20                  25                  30

Met Gln Gln Lys Tyr Glu Ala Ser Arg Glu Asp Ile Tyr Lys Arg Asn
        35                  40                  45

Ile Glu Leu Lys Val Glu Val Glu Ser Leu Lys Arg Glu Leu Gln Asp
    50                  55                  60

Lys Lys Gln His Leu Asp Lys Thr Trp Ala Asp Val Glu Asn Leu Asn
65                  70                  75                  80

Ser Gln Asn Glu Ala Glu Leu Arg Arg Gln Phe Glu Glu Arg Gln Gln
                85                  90                  95

Glu Thr Glu His Val Tyr Glu Leu Leu Glu Asn Lys Ile Gln Leu Leu
            100                 105                 110

Gln Glu Glu Ser Arg Leu Ala Lys Asn Glu Ala Ala Arg Met Ala Ala
        115                 120                 125

Leu Val Glu Ala Glu Lys Glu Cys Asn Leu Glu Leu Ser Glu Lys Leu
    130                 135                 140

Lys Gly Val Thr Lys Asn Trp Glu Asp Val Pro Gly Asp Gln Val Lys
145                 150                 155                 160

Pro Asp Gln Tyr Thr Glu Ala Leu Ala Gln Arg Asp Lys Arg Ile Glu
                165                 170                 175

Glu Leu Asn Gln Ser Leu Ala Ala Gln Glu Arg Leu Val Glu Gln Leu
            180                 185                 190

Ser Arg Glu Lys Gln Gln Leu Leu His Leu Leu Glu Glu Pro Thr Ser
        195                 200                 205

Met Glu Val Gln Pro Met Thr Glu Glu Leu Leu Lys Gln Gln Lys Leu
    210                 215                 220

Asn Ser His Glu Thr Thr Ile Thr Gln Gln Ser Val Ser Asp Ser His
225                 230                 235                 240

Leu Ala Glu Leu Gln Glu Lys Ile Gln Gln Thr Glu Ala Thr Asn Lys
                245                 250                 255

Ile Leu Gln Glu Lys Leu Asn Glu Met Ser Tyr Glu Leu Lys Cys Ala
            260                 265                 270

Gln Glu Ser Ser Gln Lys Gln Asp Gly Thr Ile Gln Asn Leu Lys Glu
        275                 280                 285

Thr Leu Lys Ser Arg Glu Arg Glu Thr Glu Glu Leu Tyr Gln Val Ile
    290                 295                 300

Glu Gly Gln Asn Asp Thr Met Ala Lys Leu Arg Glu Met Leu His Gln
305                 310                 315                 320

Ser Gln Leu Gly Gln Leu His Ser Ser Glu Gly Thr Ser Pro Ala Gln
                325                 330                 335

Gln Gln Val Ala Leu Leu Asp Leu Gln Ser Ala Leu Phe Cys Ser Gln
```

-continued

```
            340                 345                 350

Leu Glu Ile Gln Lys Leu Gln Arg Val Val Arg Gln Lys Glu Arg Gln
        355                 360                 365

Leu Ala Asp Ala Lys Gln Cys Val Gln Phe Val Glu Ala Ala Ala His
    370                 375                 380

Glu Ser Glu Gln Gln Lys Glu Ala Ser Trp Lys His Asn Gln Glu Leu
385                 390                 395                 400

Arg Lys Ala Leu Gln Gln Leu Gln Glu Glu Leu Gln Asn Lys Ser Gln
                405                 410                 415

Gln Leu Arg Ala Trp Glu Ala Glu Lys Tyr Asn Glu Ile Arg Thr Gln
            420                 425                 430

Glu Gln Asn Ile Gln His Leu Asn His Ser Leu Ser His Lys Glu Gln
        435                 440                 445

Leu Leu Gln Glu Phe Arg Glu Leu Leu Gln Tyr Arg Asp Asn Ser Asp
    450                 455                 460

Lys Thr Leu Glu Ala Asn Glu Met Leu Leu Glu Lys Leu Arg Gln Arg
465                 470                 475                 480

Ile His Asp Lys Ala Val Ala Leu Glu Arg Ala Ile Asp Glu Lys Phe
                485                 490                 495

Ser Ala Leu Glu Glu Lys Glu Lys Glu Leu Arg Gln Leu Arg Leu Ala
            500                 505                 510

Val Arg Glu Arg Asp His Asp Leu Glu Arg Leu Arg Asp Val Leu Ser
        515                 520                 525

Ser Asn Glu Ala Thr Met Gln Ser Met Glu Ser Leu Leu Arg Ala Lys
    530                 535                 540

Gly Leu Glu Val Glu Gln Leu Ser Thr Thr Cys Gln Asn Leu Gln Trp
545                 550                 555                 560

Leu Lys Glu Glu Met Glu Thr Lys Phe Ser Arg Trp Gln Lys Glu Gln
                565                 570                 575

Glu Ser Ile Ile Gln Gln Leu Gln Thr Ser Leu His Asp Arg Asn Lys
            580                 585                 590

Glu Val Glu Asp Leu Ser Ala Thr Leu Leu Cys Lys Leu Gly Pro Gly
        595                 600                 605

Gln Ser Glu Ile Ala Glu Glu Leu Cys Gln Arg Leu Gln Arg Lys Glu
    610                 615                 620

Arg Met Leu Gln Asp Leu Leu Ser Asp Arg Asn Lys Gln Val Leu Glu
625                 630                 635                 640

His Glu Met Glu Ile Gln Gly Leu Leu Gln Ser Val Ser Thr Arg Glu
                645                 650                 655

Gln Glu Ser Gln Ala Ala Ala Glu Lys Leu Val Gln Ala Leu Met Glu
            660                 665                 670

Arg Asn Ser Glu Leu Gln Ala Leu Arg Gln Tyr Leu Gly Gly Arg Asp
        675                 680                 685

Ser Leu Met Ser Gln Ala Pro Ile Ser Asn Gln Gln Ala Glu Val Thr
    690                 695                 700

Pro Thr Gly Cys Leu Gly Lys Gln Thr Asp Gln Gly Ser Met Gln Ile
705                 710                 715                 720

Pro Ser Arg Asp Asp Ser Thr Ser Leu Thr Ala Lys Glu Asp Val Ser
                725                 730                 735

Ile Pro Arg Ser Thr Leu Gly Asp Leu Asp Thr Val Ala Gly Leu Glu
            740                 745                 750

Lys Glu Leu Ser Asn Ala Lys Glu Glu Leu Glu Leu Met Ala Lys Lys
        755                 760                 765
```

```
Glu Arg Glu Ser Gln Met Glu Leu Ser Ala Leu Gln Ser Met Met Ala
    770                 775                 780

Val Gln Glu Glu Glu Leu Gln Val Gln Ala Ala Asp Met Glu Ser Leu
785                 790                 795                 800

Thr Arg Asn Ile Gln Ile Lys Glu Asp Leu Ile Lys Asp Leu Gln Met
                805                 810                 815

Gln Leu Val Asp Pro Glu Asp Ile Pro Ala Met Glu Arg Leu Thr Gln
            820                 825                 830

Glu Val Leu Leu Leu Arg Glu Lys Val Ala Ser Val Glu Ser Gln Gly
        835                 840                 845

Gln Glu Ile Ser Gly Asn Arg Arg Gln Gln Leu Leu Leu Met Leu Glu
    850                 855                 860

Gly Leu Val Asp Glu Arg Ser Arg Leu Asn Glu Ala Leu Gln Ala Glu
865                 870                 875                 880

Arg Gln Leu Tyr Ser Ser Leu Val Lys Phe His Ala His Pro Glu Ser
                885                 890                 895

Ser Glu Arg Asp Arg Thr Leu Gln Val Glu Leu Glu Gly Ala Gln Val
            900                 905                 910

Leu Arg Ser Arg Leu Glu Glu Val Leu Gly Arg Ser Leu Glu Arg Leu
        915                 920                 925

Asn Arg Leu Glu Thr Leu Ala Ala Ile Gly Gly Ala Ala Ala Gly Asp
    930                 935                 940

Asp Thr Glu Asp Thr Ser Thr Glu Phe Thr Asp Ser Ile Glu Glu Glu
945                 950                 955                 960

Ala Ala His His Ser His Gln Gln Leu Val Lys Val Ala Leu Glu Lys
                965                 970                 975

Ser Leu Ala Thr Val Glu Thr Gln Asn Pro Ser Phe Ser Pro Pro Ser
            980                 985                 990

Pro Met Gly Gly Asp Ser Asn Arg  Cys Leu Gln Glu Glu  Met Leu His
        995                 1000                 1005

Leu Arg  Ala Glu Phe His Gln  His Leu Glu Glu Lys  Arg Lys Ala
    1010                 1015                 1020

Glu Glu  Glu Leu Lys Glu Leu  Lys Ala Gln Ile Glu  Glu Ala Gly
    1025                 1030                 1035

Phe Ser  Ser Val Ser His Ile  Arg Asn Thr Met Leu  Ser Leu Cys
    1040                 1045                 1050

Leu Glu  Asn Ala Glu Leu Lys  Glu Gln Met Gly Glu  Ala Met Ser
    1055                 1060                 1065

Asp Gly  Trp Glu Ile Glu Glu  Asp Lys Glu Lys Gly  Glu Val Met
    1070                 1075                 1080

Val Glu  Thr Val Val Thr Lys  Glu Gly Leu Ser Glu  Ser Ser Leu
    1085                 1090                 1095

Gln Ala  Glu Phe Arg Lys Leu  Gln Gly Lys Leu Lys  Asn Ala His
    1100                 1105                 1110

Asn Ile  Ile Asn Leu Leu Lys  Glu Gln Leu Val Leu  Ser Ser Lys
    1115                 1120                 1125

Glu Gly  Asn Ser Lys Leu Thr  Pro Glu Leu Leu Val  His Leu Thr
    1130                 1135                 1140

Ser Thr  Ile Glu Arg Ile Asn  Thr Glu Leu Val Gly  Ser Pro Gly
    1145                 1150                 1155

Lys His  Gln His Gln Glu Glu  Gly Asn Val Thr Val  Arg Pro Phe
    1160                 1165                 1170
```

-continued

```
Pro Arg  Pro Gln Ser Leu Asp  Leu Gly Ala Thr Phe  Thr Val Asp
    1175                 1180                 1185

Ala His  Gln Leu Asp Asn Gln  Ser Gln Pro Arg Asp  Pro Gly Pro
    1190                 1195                 1200

Gln Ser  Ala Phe Ser Leu Pro  Gly Ser Thr Gln His  Leu Arg Ser
    1205                 1210                 1215

Gln Leu  Ser Gln Cys Lys Gln  Arg Tyr Gln Asp Leu  Gln Glu Lys
    1220                 1225                 1230

Leu Leu  Leu Ser Glu Ala Thr  Val Phe Ala Gln Ala  Asn Glu Leu
    1235                 1240                 1245

Glu Lys  Tyr Arg Val Met Leu  Thr Gly Glu Ser Leu  Val Lys Gln
    1250                 1255                 1260

Asp Ser  Lys Gln Ile Gln Val  Asp Leu Gln Asp Leu  Gly Tyr Glu
    1265                 1270                 1275

Thr Cys  Gly Arg Ser Glu Asn  Glu Ala Glu Arg Glu  Glu Thr Thr
    1280                 1285                 1290

Ser Pro  Glu Cys Glu Glu His  Asn Ser Leu Lys Glu  Met Val Leu
    1295                 1300                 1305

Met Glu  Gly Leu Cys Ser Glu  Gln Gly Arg Arg Gly  Ser Thr Leu
    1310                 1315                 1320

Ala Ser  Ser Ser Glu Arg Lys  Pro Leu Glu Asn Gln  Leu Gly Lys
    1325                 1330                 1335

Gln Glu  Glu Phe Arg Val Tyr  Gly Lys Ser Glu Asn  Ile Leu Val
    1340                 1345                 1350

Leu Arg  Lys Asp Ile Lys Asp  Leu Lys Ala Gln Leu  Gln Asn Ala
    1355                 1360                 1365

Asn Lys  Val Ile Gln Asn Leu  Lys Ser Arg Val Arg  Ser Leu Ser
    1370                 1375                 1380

Val Thr  Ser Asp Tyr Ser Ser  Ser Leu Glu Arg Pro  Trp Lys Leu
    1385                 1390                 1395

Arg Ala  Val Gly Thr Leu Glu  Gly Ser Ser Pro His  Ser Val Pro
    1400                 1405                 1410

Asp Glu  Asp Glu Gly Trp Leu  Ser Asp Gly Thr Gly  Ala Phe Tyr
    1415                 1420                 1425

Ser Pro  Gly Leu Gln Ala Lys  Lys Asp Leu Glu Ser  Leu Ile Gln
    1430                 1435                 1440

Arg Val  Ser Gln Leu Glu Ala  Gln Leu Pro Lys Asn  Gly Leu Glu
    1445                 1450                 1455

Glu Lys  Leu Ala Glu Glu Leu  Arg Ser Ala Ser Trp  Pro Gly Lys
    1460                 1465                 1470

Tyr Asp  Ser Leu Ile Gln Asp  Gln Ala Arg Glu Leu  Ser Tyr Leu
    1475                 1480                 1485

Arg Gln  Lys Ile Arg Glu Gly  Arg Gly Ile Cys Tyr  Leu Ile Thr
    1490                 1495                 1500

Arg His  Ala Lys Asp Thr Val  Lys Ser Phe Glu Asp  Leu Leu Arg
    1505                 1510                 1515

Ser Asn  Asp Ile Asp Tyr Tyr  Leu Gly Gln Ser Phe  Arg Glu Gln
    1520                 1525                 1530

Leu Ala  Gln Gly Ser Gln Leu  Thr Glu Arg Leu Thr  Ser Lys Leu
    1535                 1540                 1545

Ser Thr  Lys Asp His Lys Ser  Glu Lys Asp Gln Ala  Gly Leu Glu
    1550                 1555                 1560

Pro Leu  Ala Leu Arg Leu Ser  Arg Glu Leu Gln Glu  Lys Glu Lys
```

```
    1565                1570                1575

Val Ile  Glu Val Leu Gln Ala  Lys Leu Asp Ala Arg  Ser Leu Thr
    1580                1585                1590

Pro Ser  Ser Ser His Ala Leu  Ser Asp Ser His Arg  Ser Pro Ser
    1595                1600                1605

Ser Thr  Ser Phe Leu Ser Asp  Glu Leu Glu Ala Cys  Ser Asp Met
    1610                1615                1620

Asp Ile  Val Ser Glu Tyr Thr  His Tyr Glu Glu Lys  Lys Ala Ser
    1625                1630                1635

Pro Ser  His Ser Asp Ser Ile  His His Ser Ser His  Ser Ala Val
    1640                1645                1650

Leu Ser  Ser Lys Pro Ser Ser  Thr Ser Ala Ser Gln  Gly Ala Lys
    1655                1660                1665

Ala Glu  Ser Asn Ser Asn Pro  Ile Ser Leu Pro Thr  Pro Gln Asn
    1670                1675                1680

Thr Pro  Lys Glu Ala Asn Gln  Ala His Ser Gly Phe  His Phe His
    1685                1690                1695

Ser Ile  Pro Lys Leu Ala Ser  Leu Pro Gln Ala Pro  Leu Pro Ser
    1700                1705                1710

Ala Pro  Ser Ser Phe Leu Pro  Phe Ser Pro Thr Gly  Pro Leu Leu
    1715                1720                1725

Leu Gly  Cys Cys Glu Thr Pro  Val Val Ser Leu Ala  Glu Ala Gln
    1730                1735                1740

Gln Glu  Leu Gln Met Leu Gln  Lys Gln Leu Gly Glu  Ser Ala Ser
    1745                1750                1755

Thr Val  Pro Pro Ala Ser Thr  Ala Thr Leu Leu Ser  Asn Asp Leu
    1760                1765                1770

Glu Ala  Asp Ser Ser Tyr Tyr  Leu Asn Ser Ala Gln  Pro His Ser
    1775                1780                1785

Pro Pro  Arg Gly Thr Ile Glu  Leu Gly Arg Ile Leu  Glu Pro Gly
    1790                1795                1800

Tyr Leu  Gly Ser Ser Gly Lys  Trp Asp Val Met Arg  Pro Gln Lys
    1805                1810                1815

Gly Ser  Val Ser Gly Asp Leu  Ser Ser Gly Ser Ser  Val Tyr Gln
    1820                1825                1830

Leu Asn  Ser Lys Pro Thr Gly  Ala Asp Leu Leu Glu  Glu His Leu
    1835                1840                1845

Gly Glu  Ile Arg Asn Leu Arg  Gln Arg Leu Glu Glu  Ser Ile Cys
    1850                1855                1860

Ile Asn  Asp Arg Leu Arg Glu  Gln Leu Glu His Arg  Leu Thr Ser
    1865                1870                1875

Thr Ala  Arg Gly Arg Gly Ser  Thr Ser Asn Phe Tyr  Ser Gln Gly
    1880                1885                1890

Leu Glu  Ser Ile Pro Gln Leu  Cys Asn Glu Asn Arg  Val Leu Arg
    1895                1900                1905

Glu Asp  Asn Arg Arg Leu Gln  Ala Gln Leu Ser His  Val Ser Arg
    1910                1915                1920

Glu His  Ser Gln Glu Thr Glu  Ser Leu Arg Glu Ala  Leu Leu Ser
    1925                1930                1935

Ser Arg  Ser His Leu Gln Glu  Leu Glu Lys Glu Leu  Glu His Gln
    1940                1945                1950

Lys Val  Glu Arg Gln Gln Leu  Leu Glu Asp Leu Arg  Glu Lys Gln
    1955                1960                1965
```

```
Gln Glu  Val Leu His Phe Arg  Glu Glu Arg Leu Ser  Leu Gln Glu
    1970                 1975                 1980

Asn Asp  Ser Arg Leu Gln His  Lys Leu Val Leu Leu  Gln Gln Gln
    1985                 1990                 1995

Cys Glu  Glu Lys Gln Gln Leu  Phe Glu Ser Leu Gln  Ser Glu Leu
    2000                 2005                 2010

Gln Ile  Tyr Glu Ala Leu Tyr  Gly Asn Ser Lys Lys  Gly Leu Lys
    2015                 2020                 2025

Ala Tyr  Ser Leu Asp Ala Cys  His Gln Ile Pro Leu  Ser Ser Asp
    2030                 2035                 2040

Leu Ser  His Leu Val Ala Glu  Val Arg Ala Leu Arg  Gly Gln Leu
    2045                 2050                 2055

Glu Gln  Ser Ile Gln Gly Asn  Asn Cys Leu Arg Leu  Gln Leu Gln
    2060                 2065                 2070

Gln Gln  Leu Glu Ser Gly Ala  Gly Lys Ala Ser Leu  Ser Pro Ser
    2075                 2080                 2085

Ser Ile  Asn Gln Asn Phe Pro  Ala Ser Thr Asp Pro  Gly Asn Lys
    2090                 2095                 2100

Gln Leu  Leu Leu Gln Asp Ser  Ala Val Ser Pro Pro  Val Arg Asp
    2105                 2110                 2115

Val Gly  Met Asn Ser Pro Ala  Leu Val Phe Pro Ser  Ser Ala Ser
    2120                 2125                 2130

Ser Thr  Pro Gly Ser Glu Thr  Pro Ile Ile Asn Arg  Ala Asn Gly
    2135                 2140                 2145

Leu Gly  Leu Asp Thr Ser Pro  Val Met Lys Thr Pro  Pro Lys Leu
    2150                 2155                 2160

Glu Gly  Asp Ala Thr Asp Gly  Ser Phe Ala Asn Lys  His Gly Arg
    2165                 2170                 2175

His Val  Ile Gly His Ile Asp  Asp Tyr Ser Ala Leu  Arg Gln Gln
    2180                 2185                 2190

Ile Ala  Glu Gly Lys Leu Leu  Val Lys Lys Ile Val  Ser Leu Val
    2195                 2200                 2205

Arg Ser  Ala Cys Ser Phe Pro  Gly Leu Glu Ala Gln  Gly Thr Glu
    2210                 2215                 2220

Val Leu  Gly Ser Lys Gly Ile  His Glu Leu Arg Ser  Ser Thr Ser
    2225                 2230                 2235

Ala Leu  His His Ala Leu Glu  Glu Ser Ala Ser Leu  Leu Thr Met
    2240                 2245                 2250

Phe Trp  Arg Ala Ala Leu Pro  Ser Thr His Ile Pro  Val Leu Pro
    2255                 2260                 2265

Gly Lys  Val Gly Glu Ser Thr  Glu Arg Glu Leu Leu  Glu Leu Arg
    2270                 2275                 2280

Thr Lys  Val Ser Lys Gln Glu  Arg Leu Leu Gln Ser  Thr Thr Glu
    2285                 2290                 2295

His Leu  Lys Asn Ala Asn Gln  Gln Lys Glu Ser Met  Glu Gln Phe
    2300                 2305                 2310

Ile Val  Ser Gln Leu Thr Arg  Thr His Asp Val Leu  Lys Lys Ala
    2315                 2320                 2325

Arg Thr  Asn Leu Glu Val Lys  Ser Leu Arg Ala Leu  Pro Cys Thr
    2330                 2335                 2340

Pro Ala  Leu
    2345
```

<210> SEQ ID NO 4
<211> LENGTH: 969
<212> TYPE: PRT
<213> ORGANISM: Homo sapiens

<400> SEQUENCE: 4

```
Met Ser Asn Gly Tyr Arg Thr Leu Ser Gln His Leu Asn Asp Leu Lys
1               5                   10                  15

Lys Glu Asn Phe Ser Leu Lys Leu Arg Ile Tyr Phe Leu Glu Glu Arg
            20                  25                  30

Met Gln Gln Lys Tyr Glu Ala Ser Arg Glu Asp Ile Tyr Lys Arg Asn
        35                  40                  45

Ile Glu Leu Lys Val Glu Val Glu Ser Leu Lys Arg Glu Leu Gln Asp
    50                  55                  60

Lys Lys Gln His Leu Asp Lys Thr Trp Ala Asp Val Glu Asn Leu Asn
65                  70                  75                  80

Ser Gln Asn Glu Ala Glu Leu Arg Arg Gln Phe Glu Glu Arg Gln Gln
                85                  90                  95

Glu Thr Glu His Val Tyr Glu Leu Leu Glu Asn Lys Ile Gln Leu Leu
            100                 105                 110

Gln Glu Glu Ser Arg Leu Ala Lys Asn Glu Ala Ala Arg Met Ala Ala
        115                 120                 125

Leu Val Glu Ala Glu Lys Glu Cys Asn Leu Glu Leu Ser Glu Lys Leu
    130                 135                 140

Lys Gly Val Thr Lys Asn Trp Glu Asp Val Pro Gly Asp Gln Val Lys
145                 150                 155                 160

Pro Asp Gln Tyr Thr Glu Ala Leu Ala Gln Arg Asp Lys Arg Ile Glu
                165                 170                 175

Glu Leu Asn Gln Ser Leu Ala Ala Gln Glu Arg Leu Val Glu Gln Leu
            180                 185                 190

Ser Arg Glu Lys Gln Gln Leu Leu His Leu Leu Glu Glu Pro Thr Ser
        195                 200                 205

Met Glu Val Gln Pro Met Thr Glu Glu Leu Leu Lys Gln Gln Lys Leu
    210                 215                 220

Asn Ser His Glu Thr Thr Ile Thr Gln Gln Ser Val Ser Asp Ser His
225                 230                 235                 240

Leu Ala Glu Leu Gln Glu Lys Ile Gln Gln Thr Glu Ala Thr Asn Lys
                245                 250                 255

Ile Leu Gln Glu Lys Leu Asn Glu Met Ser Tyr Glu Leu Lys Cys Ala
            260                 265                 270

Gln Glu Ser Ser Gln Lys Gln Asp Gly Thr Ile Gln Asn Leu Lys Glu
        275                 280                 285

Thr Leu Lys Ser Arg Glu Arg Glu Thr Glu Glu Leu Tyr Gln Val Ile
    290                 295                 300

Glu Gly Gln Asn Asp Thr Met Ala Lys Leu Arg Glu Met Leu His Gln
305                 310                 315                 320

Ser Gln Leu Gly Gln Leu His Ser Ser Glu Gly Thr Ser Pro Ala Gln
                325                 330                 335

Gln Gln Val Ala Leu Leu Asp Leu Gln Ser Ala Leu Phe Cys Ser Gln
            340                 345                 350

Leu Glu Ile Gln Lys Leu Gln Arg Val Val Arg Gln Lys Glu Arg Gln
        355                 360                 365

Leu Ala Asp Ala Lys Gln Cys Val Gln Phe Val Glu Ala Ala Ala His
    370                 375                 380
```

```
Glu Ser Glu Gln Gln Lys Glu Ala Ser Trp Lys His Asn Gln Glu Leu
385                 390                 395                 400

Arg Lys Ala Leu Gln Gln Leu Gln Glu Glu Leu Gln Asn Lys Ser Gln
                405                 410                 415

Gln Leu Arg Ala Trp Glu Ala Glu Lys Tyr Asn Glu Ile Arg Thr Gln
            420                 425                 430

Glu Gln Asn Ile Gln His Leu Asn His Ser Leu Ser His Lys Glu Gln
        435                 440                 445

Leu Leu Gln Glu Phe Arg Glu Leu Leu Gln Tyr Arg Asp Asn Ser Asp
    450                 455                 460

Lys Thr Leu Glu Ala Asn Glu Met Leu Leu Glu Lys Leu Arg Gln Arg
465                 470                 475                 480

Ile His Asp Lys Ala Val Ala Leu Glu Arg Ala Ile Asp Glu Lys Phe
                485                 490                 495

Ser Ala Leu Glu Glu Lys Glu Lys Glu Leu Arg Gln Leu Arg Leu Ala
            500                 505                 510

Val Arg Glu Arg Asp His Asp Leu Glu Arg Leu Arg Asp Val Leu Ser
        515                 520                 525

Ser Asn Glu Ala Thr Met Gln Ser Met Glu Ser Leu Leu Arg Ala Lys
    530                 535                 540

Gly Leu Glu Val Glu Gln Leu Ser Thr Thr Cys Gln Asn Leu Gln Trp
545                 550                 555                 560

Leu Lys Glu Glu Met Glu Thr Lys Phe Ser Arg Trp Gln Lys Glu Gln
                565                 570                 575

Glu Ser Ile Ile Gln Gln Leu Gln Thr Ser Leu His Asp Arg Asn Lys
            580                 585                 590

Glu Val Glu Asp Leu Ser Ala Thr Leu Leu Cys Lys Leu Gly Pro Gly
        595                 600                 605

Gln Ser Glu Ile Ala Glu Glu Leu Cys Gln Arg Leu Gln Arg Lys Glu
    610                 615                 620

Arg Met Leu Gln Asp Leu Leu Ser Asp Arg Asn Lys Gln Val Leu Glu
625                 630                 635                 640

His Glu Met Glu Ile Gln Gly Leu Leu Gln Ser Val Ser Thr Arg Glu
                645                 650                 655

Gln Glu Ser Gln Ala Ala Ala Glu Lys Leu Val Gln Ala Leu Met Glu
            660                 665                 670

Arg Asn Ser Glu Leu Gln Ala Leu Arg Gln Tyr Leu Gly Gly Arg Asp
        675                 680                 685

Ser Leu Met Ser Gln Ala Pro Ile Ser Asn Gln Gln Ala Glu Val Thr
    690                 695                 700

Pro Thr Gly Cys Leu Gly Lys Gln Thr Asp Gln Gly Ser Met Gln Ile
705                 710                 715                 720

Pro Ser Arg Asp Asp Ser Thr Ser Leu Thr Ala Lys Glu Asp Val Ser
                725                 730                 735

Ile Pro Arg Ser Thr Leu Gly Asp Leu Asp Thr Val Ala Gly Leu Glu
            740                 745                 750

Lys Glu Leu Ser Asn Ala Lys Glu Glu Leu Glu Leu Met Ala Lys Lys
        755                 760                 765

Glu Arg Glu Ser Gln Met Glu Leu Ser Ala Leu Gln Ser Met Met Ala
    770                 775                 780

Val Gln Glu Glu Glu Leu Gln Val Gln Ala Ala Asp Met Glu Ser Leu
785                 790                 795                 800
```

```
Thr Arg Asn Ile Gln Ile Lys Glu Asp Leu Ile Lys Asp Leu Gln Met
                805                 810                 815

Gln Leu Val Asp Pro Glu Asp Ile Pro Ala Met Glu Arg Leu Thr Gln
            820                 825                 830

Glu Val Leu Leu Leu Arg Glu Lys Val Ala Ser Val Glu Ser Gln Gly
        835                 840                 845

Gln Glu Ile Ser Gly Asn Arg Arg Gln Gln Leu Leu Leu Met Leu Glu
    850                 855                 860

Gly Leu Val Asp Glu Arg Ser Arg Leu Asn Glu Ala Leu Gln Ala Glu
865                 870                 875                 880

Arg Gln Leu Tyr Ser Ser Leu Val Lys Phe His Ala His Pro Glu Ser
                885                 890                 895

Ser Glu Arg Asp Arg Thr Leu Gln Val Glu Leu Glu Gly Ala Gln Val
            900                 905                 910

Leu Arg Ser Arg Leu Glu Glu Val Leu Gly Arg Ser Leu Glu Arg Leu
        915                 920                 925

Asn Arg Leu Glu Thr Leu Ala Ala Ile Gly Gly Ala Ala Ala Gly Asp
    930                 935                 940

Asp Thr Glu Asp Thr Ser Thr Glu Phe Thr Asp Ser Ile Glu Glu Glu
945                 950                 955                 960

Ala Ala His His Ser His Gln Gln Leu
                965


<210> SEQ ID NO 5
<211> LENGTH: 310
<212> TYPE: PRT
<213> ORGANISM: Homo sapiens

<400> SEQUENCE: 5

Met Lys Gly Thr Asp Ser Gly Ser Cys Cys Arg Arg Arg Cys Asp Phe
1               5                   10                  15

Gly Cys Cys Cys Arg Ala Ser Arg Arg Ala His Tyr Thr Pro Tyr Arg
            20                  25                  30

Ser Gly Asp Ala Thr Arg Thr Pro Gln Ser Pro Arg Gln Thr Pro Ser
        35                  40                  45

Arg Glu Arg Arg Arg Pro Glu Pro Ala Gly Ser Trp Ala Ala Ala Ala
    50                  55                  60

Glu Glu Glu Glu Ala Ala Ala Ala Ala Thr Pro Trp Met Arg Asp Tyr
65                  70                  75                  80

Phe Ala Glu Asp Asp Gly Glu Met Val Pro Arg Thr Ser His Thr Ala
                85                  90                  95

Ala Phe Leu Ser Asp Thr Lys Asp Arg Gly Pro Pro Val Gln Ser Gln
            100                 105                 110

Ile Trp Arg Ser Gly Glu Lys Val Pro Phe Val Gln Thr Tyr Ser Leu
        115                 120                 125

Arg Ala Phe Glu Lys Pro Pro Gln Val Gln Thr Gln Ala Leu Arg Asp
    130                 135                 140

Phe Glu Lys His Leu Asn Asp Leu Lys Lys Glu Asn Phe Ser Leu Lys
145                 150                 155                 160

Leu Arg Ile Tyr Phe Leu Glu Glu Arg Met Gln Gln Lys Tyr Glu Ala
                165                 170                 175

Ser Arg Glu Asp Ile Tyr Lys Arg Asn Ile Glu Leu Lys Val Glu Val
            180                 185                 190

Glu Ser Leu Lys Arg Glu Leu Gln Asp Lys Lys Gln His Leu Asp Lys
        195                 200                 205
```

```
Thr Trp Ala Asp Val Glu Asn Leu Asn Ser Gln Asn Glu Ala Glu Leu
    210                 215                 220

Arg Arg Gln Phe Glu Glu Arg Gln Gln Glu Thr Glu His Val Tyr Glu
225                 230                 235                 240

Leu Leu Glu Asn Lys Ile Gln Leu Leu Gln Glu Glu Ser Arg Leu Ala
                245                 250                 255

Lys Asn Glu Ala Ala Arg Met Ala Ala Leu Val Glu Ala Glu Lys Glu
            260                 265                 270

Cys Asn Leu Glu Leu Ser Glu Lys Leu Lys Gly Val Thr Lys Asn Trp
        275                 280                 285

Glu Asp Val Pro Gly Asp Gln Val Lys Pro Asp Gln Tyr Thr Glu Ala
    290                 295                 300

Leu Ala Gln Arg Asp Lys
305                 310


<210> SEQ ID NO 6
<211> LENGTH: 173
<212> TYPE: PRT
<213> ORGANISM: Homo sapiens

<400> SEQUENCE: 6

Met Ser Asn Gly Tyr Arg Thr Leu Ser Gln His Leu Asn Asp Leu Lys
1               5                   10                  15

Lys Glu Asn Phe Ser Leu Lys Leu Arg Ile Tyr Phe Leu Glu Glu Arg
            20                  25                  30

Met Gln Gln Lys Tyr Glu Ala Ser Arg Glu Asp Ile Tyr Lys Arg Asn
        35                  40                  45

Ile Glu Leu Lys Val Glu Val Glu Ser Leu Lys Arg Glu Leu Gln Asp
    50                  55                  60

Lys Lys Gln His Leu Asp Lys Thr Trp Ala Asp Val Glu Asn Leu Asn
65                  70                  75                  80

Ser Gln Asn Glu Ala Glu Leu Arg Arg Gln Phe Glu Glu Arg Gln Gln
                85                  90                  95

Glu Thr Glu His Val Tyr Glu Leu Leu Glu Asn Lys Ile Gln Leu Leu
            100                 105                 110

Gln Glu Glu Ser Arg Leu Ala Lys Asn Glu Ala Ala Arg Met Ala Ala
        115                 120                 125

Leu Val Glu Ala Glu Lys Glu Cys Asn Leu Glu Leu Ser Glu Lys Leu
    130                 135                 140

Lys Gly Val Thr Lys Asn Trp Glu Asp Val Pro Gly Asp Gln Val Lys
145                 150                 155                 160

Pro Asp Gln Tyr Thr Glu Ala Leu Ala Gln Arg Asp Lys
                165                 170


<210> SEQ ID NO 7
<211> LENGTH: 1132
<212> TYPE: PRT
<213> ORGANISM: Homo sapiens

<400> SEQUENCE: 7

Met Lys Glu Ile Cys Arg Ile Cys Ala Arg Glu Leu Cys Gly Asn Gln
1               5                   10                  15

Arg Arg Trp Ile Phe His Thr Ala Ser Lys Leu Asn Leu Gln Val Leu
            20                  25                  30

Leu Ser His Val Leu Gly Lys Asp Val Pro Arg Asp Gly Lys Ala Glu
        35                  40                  45
```

```
Phe Ala Cys Ser Lys Cys Ala Phe Met Leu Asp Arg Ile Tyr Arg Phe
    50                  55                  60

Asp Thr Val Ile Ala Arg Ile Glu Ala Leu Ser Ile Glu Arg Leu Gln
65                  70                  75                  80

Lys Leu Leu Leu Glu Lys Asp Arg Leu Lys Phe Cys Ile Ala Ser Met
                85                  90                  95

Tyr Arg Lys Asn Asn Asp Asp Ser Gly Ala Glu Ile Lys Ala Gly Asn
            100                 105                 110

Gly Thr Val Asp Met Ser Val Leu Pro Asp Ala Arg Tyr Ser Ala Leu
        115                 120                 125

Leu Gln Glu Asp Phe Ala Tyr Ser Gly Phe Glu Cys Trp Val Glu Asn
    130                 135                 140

Glu Asp Gln Ile Gln Glu Pro His Ser Cys His Gly Ser Glu Gly Pro
145                 150                 155                 160

Gly Asn Arg Pro Arg Arg Cys Arg Gly Cys Ala Ala Leu Arg Val Ala
                165                 170                 175

Asp Ser Asp Tyr Glu Ala Ile Cys Lys Val Pro Arg Lys Val Ala Arg
            180                 185                 190

Ser Ile Ser Cys Gly Pro Ser Ser Arg Trp Ser Thr Ser Ile Cys Thr
        195                 200                 205

Glu Glu Pro Ala Leu Ser Glu Val Gly Pro Pro Asp Leu Ala Ser Thr
    210                 215                 220

Lys Val Pro Pro Asp Gly Glu Ser Met Glu Glu Glu Thr Pro Gly Ser
225                 230                 235                 240

Ser Val Glu Ser Leu Asp Ala Ser Val Gln Ala Ser Pro Pro Gln Gln
                245                 250                 255

Lys Asp Glu Glu Thr Glu Arg Ser Ala Lys Glu Leu Gly Lys Cys Asp
            260                 265                 270

Cys Cys Ser Asp Asp Gln Ala Pro Gln His Gly Cys Asn His Lys Leu
        275                 280                 285

Glu Leu Ala Leu Ser Met Ile Lys Gly Leu Asp Tyr Lys Pro Ile Gln
    290                 295                 300

Ser Pro Arg Gly Ser Arg Leu Pro Ile Pro Val Lys Ser Ser Leu Pro
305                 310                 315                 320

Gly Ala Lys Pro Gly Pro Ser Met Thr Asp Gly Val Ser Ser Gly Phe
                325                 330                 335

Leu Asn Arg Ser Leu Lys Pro Leu Tyr Lys Thr Pro Val Ser Tyr Pro
            340                 345                 350

Leu Glu Leu Ser Asp Leu Gln Glu Leu Trp Asp Asp Leu Cys Glu Asp
        355                 360                 365

Tyr Leu Pro Leu Arg Val Gln Pro Met Thr Glu Glu Leu Leu Lys Gln
    370                 375                 380

Gln Lys Leu Asn Ser His Glu Thr Thr Ile Thr Gln Gln Ser Val Ser
385                 390                 395                 400

Asp Ser His Leu Ala Glu Leu Gln Glu Lys Ile Gln Gln Thr Glu Ala
                405                 410                 415

Thr Asn Lys Ile Leu Gln Glu Lys Leu Asn Glu Met Ser Tyr Glu Leu
            420                 425                 430

Lys Cys Ala Gln Glu Ser Ser Gln Lys Gln Asp Gly Thr Ile Gln Asn
        435                 440                 445

Leu Lys Glu Thr Leu Lys Ser Arg Glu Arg Glu Thr Glu Glu Leu Tyr
    450                 455                 460
```

```
Gln Val Ile Glu Gly Gln Asn Asp Thr Met Ala Lys Leu Arg Glu Met
465                 470                 475                 480

Leu His Gln Ser Gln Leu Gly Gln Leu His Ser Ser Glu Gly Thr Ser
                485                 490                 495

Pro Ala Gln Gln Gln Val Ala Leu Leu Asp Leu Gln Ser Ala Leu Phe
            500                 505                 510

Cys Ser Gln Leu Glu Ile Gln Lys Leu Gln Arg Val Val Arg Gln Lys
        515                 520                 525

Glu Arg Gln Leu Ala Asp Ala Lys Gln Cys Val Gln Phe Val Glu Ala
    530                 535                 540

Ala Ala His Glu Ser Glu Gln Gln Lys Glu Ala Ser Trp Lys His Asn
545                 550                 555                 560

Gln Glu Leu Arg Lys Ala Leu Gln Gln Leu Gln Glu Glu Leu Gln Asn
                565                 570                 575

Lys Ser Gln Gln Leu Arg Ala Trp Glu Ala Glu Lys Tyr Asn Glu Ile
            580                 585                 590

Arg Thr Gln Glu Gln Asn Ile Gln His Leu Asn His Ser Leu Ser His
        595                 600                 605

Lys Glu Gln Leu Leu Gln Glu Phe Arg Glu Leu Leu Gln Tyr Arg Asp
    610                 615                 620

Asn Ser Asp Lys Thr Leu Glu Ala Asn Glu Met Leu Leu Glu Lys Leu
625                 630                 635                 640

Arg Gln Arg Ile His Asp Lys Ala Val Ala Leu Glu Arg Ala Ile Asp
                645                 650                 655

Glu Lys Phe Ser Ala Leu Glu Glu Lys Glu Lys Glu Leu Arg Gln Leu
            660                 665                 670

Arg Leu Ala Val Arg Glu Arg Asp His Asp Leu Glu Arg Leu Arg Asp
        675                 680                 685

Val Leu Ser Ser Asn Glu Ala Thr Met Gln Ser Met Glu Ser Leu Leu
    690                 695                 700

Arg Ala Lys Gly Leu Glu Val Glu Gln Leu Ser Thr Thr Cys Gln Asn
705                 710                 715                 720

Leu Gln Trp Leu Lys Glu Glu Met Glu Thr Lys Phe Ser Arg Trp Gln
                725                 730                 735

Lys Glu Gln Glu Ser Ile Ile Gln Gln Leu Gln Thr Ser Leu His Asp
            740                 745                 750

Arg Asn Lys Glu Val Glu Asp Leu Ser Ala Thr Leu Leu Cys Lys Leu
        755                 760                 765

Gly Pro Gly Gln Ser Glu Ile Ala Glu Glu Leu Cys Gln Arg Leu Gln
    770                 775                 780

Arg Lys Glu Arg Met Leu Gln Asp Leu Leu Ser Asp Arg Asn Lys Gln
785                 790                 795                 800

Val Leu Glu His Glu Met Glu Ile Gln Gly Leu Leu Gln Ser Val Ser
                805                 810                 815

Thr Arg Glu Gln Glu Ser Gln Ala Ala Ala Glu Lys Leu Val Gln Ala
            820                 825                 830

Leu Met Glu Arg Asn Ser Glu Leu Gln Ala Leu Arg Gln Tyr Leu Gly
        835                 840                 845

Gly Arg Asp Ser Leu Met Ser Gln Ala Pro Ile Ser Asn Gln Gln Ala
    850                 855                 860

Glu Val Thr Pro Thr Gly Cys Leu Gly Lys Gln Thr Asp Gln Gly Ser
865                 870                 875                 880

Met Gln Ile Pro Ser Arg Asp Asp Ser Thr Ser Leu Thr Ala Lys Glu
```

```
                885                 890                 895

Asp Val Ser Ile Pro Arg Ser Thr Leu Gly Asp Leu Asp Thr Val Ala
            900                 905                 910

Gly Leu Glu Lys Glu Leu Ser Asn Ala Lys Glu Glu Leu Glu Leu Met
        915                 920                 925

Ala Lys Lys Glu Arg Glu Ser Gln Met Glu Leu Ser Ala Leu Gln Ser
    930                 935                 940

Met Met Ala Val Gln Glu Glu Glu Leu Gln Val Gln Ala Ala Asp Met
945                 950                 955                 960

Glu Ser Leu Thr Arg Asn Ile Gln Ile Lys Glu Asp Leu Ile Lys Asp
                965                 970                 975

Leu Gln Met Gln Leu Val Asp Pro Glu Asp Ile Pro Ala Met Glu Arg
            980                 985                 990

Leu Thr Gln Glu Val Leu Leu Leu  Arg Glu Lys Val Ala  Ser Val Glu
        995                 1000                1005

Ser Gln  Gly Gln Glu Ile Ser  Gly Asn Arg Arg Gln  Gln Leu Leu
    1010                1015                1020

Leu Met  Leu Glu Gly Leu Val  Asp Glu Arg Ser Arg  Leu Asn Glu
    1025                1030                1035

Ala Leu  Gln Ala Glu Arg Gln  Leu Tyr Ser Ser Leu  Val Lys Phe
    1040                1045                1050

His Ala  His Pro Glu Ser Ser  Glu Arg Asp Arg Thr  Leu Gln Val
    1055                1060                1065

Glu Leu  Glu Gly Ala Gln Val  Leu Arg Ser Arg Leu  Glu Glu Val
    1070                1075                1080

Leu Gly  Arg Ser Leu Glu Arg  Leu Asn Arg Leu Glu  Thr Leu Ala
    1085                1090                1095

Ala Ile  Gly Gly Ala Ala Ala  Gly Asp Asp Thr Glu  Asp Thr Ser
    1100                1105                1110

Thr Glu  Phe Thr Asp Ser Ile  Glu Glu Glu Ala Ala  His His Ser
    1115                1120                1125

His Gln  Gln Leu
    1130


<210> SEQ ID NO 8
<211> LENGTH: 141
<212> TYPE: PRT
<213> ORGANISM: Homo sapiens

<400> SEQUENCE: 8

Met Gln Gln Lys Tyr Glu Ala Ser Arg Glu Asp Ile Tyr Lys Arg Asn
1               5                   10                  15

Ile Glu Leu Lys Val Glu Val Glu Ser Leu Lys Arg Glu Leu Gln Asp
            20                  25                  30

Lys Lys Gln His Leu Asp Lys Thr Trp Ala Asp Val Glu Asn Leu Asn
        35                  40                  45

Ser Gln Asn Glu Ala Glu Leu Arg Arg Gln Phe Glu Glu Arg Gln Gln
    50                  55                  60

Glu Thr Glu His Val Tyr Glu Leu Leu Glu Asn Lys Ile Gln Leu Leu
65                  70                  75                  80

Gln Glu Glu Ser Arg Leu Ala Lys Asn Glu Ala Ala Arg Met Ala Ala
                85                  90                  95

Leu Val Glu Ala Glu Lys Glu Cys Asn Leu Glu Leu Ser Glu Lys Leu
            100                 105                 110
```

```
Lys Gly Val Thr Lys Asn Trp Glu Asp Val Pro Gly Asp Gln Val Lys
        115                 120                 125

Pro Asp Gln Tyr Thr Glu Ala Leu Ala Gln Arg Asp Lys
    130                 135                 140


<210> SEQ ID NO 9
<211> LENGTH: 176
<212> TYPE: PRT
<213> ORGANISM: Homo sapiens

<400> SEQUENCE: 9

Met Phe Leu Cys Gln Gly Phe Arg Lys Tyr Leu Pro Glu His Leu Asn
1               5                   10                  15

Asp Leu Lys Lys Glu Asn Phe Ser Leu Lys Leu Arg Ile Tyr Phe Leu
            20                  25                  30

Glu Glu Arg Met Gln Gln Lys Tyr Glu Ala Ser Arg Glu Asp Ile Tyr
        35                  40                  45

Lys Arg Asn Ile Glu Leu Lys Val Glu Val Glu Ser Leu Lys Arg Glu
    50                  55                  60

Leu Gln Asp Lys Lys Gln His Leu Asp Lys Thr Trp Ala Asp Val Glu
65                  70                  75                  80

Asn Leu Asn Ser Gln Asn Glu Ala Glu Leu Arg Arg Gln Phe Glu Glu
                85                  90                  95

Arg Gln Gln Glu Thr Glu His Val Tyr Glu Leu Leu Glu Asn Lys Ile
            100                 105                 110

Gln Leu Leu Gln Glu Glu Ser Arg Leu Ala Lys Asn Glu Ala Ala Arg
        115                 120                 125

Met Ala Ala Leu Val Glu Ala Glu Lys Glu Cys Asn Leu Glu Leu Ser
    130                 135                 140

Glu Lys Leu Lys Gly Val Thr Lys Asn Trp Glu Asp Val Pro Gly Asp
145                 150                 155                 160

Gln Val Lys Pro Asp Gln Tyr Thr Glu Ala Leu Ala Gln Arg Asp Lys
                165                 170                 175


<210> SEQ ID NO 10
<211> LENGTH: 2240
<212> TYPE: PRT
<213> ORGANISM: Homo sapiens

<400> SEQUENCE: 10

Met Glu Gln Thr Trp Thr Arg Asp Tyr Phe Ala Glu Asp Asp Gly Glu
1               5                   10                  15

Met Val Pro Arg Thr Ser His Thr Ala Ala Phe Leu Ser Asp Thr Lys
            20                  25                  30

Asp Arg Gly Pro Pro Val Gln Ser Gln Ile Trp Arg Ser Gly Glu Lys
        35                  40                  45

Val Pro Phe Val Gln Thr Tyr Ser Leu Arg Ala Phe Glu Lys Pro Pro
    50                  55                  60

Gln Val Gln Thr Gln Ala Leu Arg Asp Phe Glu Lys His Leu Asn Asp
65                  70                  75                  80

Leu Lys Lys Glu Asn Phe Ser Leu Lys Leu Arg Ile Tyr Phe Leu Glu
                85                  90                  95

Glu Arg Met Gln Gln Lys Tyr Glu Ala Ser Arg Glu Asp Ile Tyr Lys
            100                 105                 110

Arg Asn Ile Glu Leu Lys Val Glu Val Glu Ser Leu Lys Arg Glu Leu
        115                 120                 125
```

```
Gln Asp Lys Lys Gln His Leu Asp Lys Thr Trp Ala Asp Val Glu Asn
    130                 135                 140

Leu Asn Ser Gln Asn Glu Ala Glu Leu Arg Arg Gln Phe Glu Glu Arg
145                 150                 155                 160

Gln Gln Glu Thr Glu His Val Tyr Glu Leu Leu Glu Asn Lys Ile Gln
                165                 170                 175

Leu Leu Gln Glu Glu Ser Arg Leu Ala Lys Asn Glu Ala Ala Arg Met
            180                 185                 190

Ala Ala Leu Val Glu Ala Glu Lys Glu Cys Asn Leu Glu Leu Ser Glu
        195                 200                 205

Lys Leu Lys Gly Val Thr Lys Asn Trp Glu Asp Val Pro Gly Asp Gln
    210                 215                 220

Val Lys Pro Asp Gln Tyr Thr Glu Ala Leu Ala Gln Arg Asp Lys Arg
225                 230                 235                 240

Ile Glu Glu Leu Asn Gln Ser Leu Ala Ala Gln Glu Arg Leu Val Glu
                245                 250                 255

Gln Leu Ser Arg Glu Lys Gln Gln Leu Leu His Leu Leu Glu Glu Pro
            260                 265                 270

Thr Ser Met Glu Val Gln Pro Met Thr Glu Glu Leu Leu Lys Gln Gln
        275                 280                 285

Lys Leu Asn Ser His Glu Thr Thr Ile Thr Gln Gln Ser Val Ser Asp
    290                 295                 300

Ser His Leu Ala Glu Leu Gln Glu Lys Ile Gln Gln Thr Glu Ala Thr
305                 310                 315                 320

Asn Lys Ile Leu Gln Glu Lys Leu Asn Glu Met Ser Tyr Glu Leu Lys
                325                 330                 335

Cys Ala Gln Glu Ser Ser Gln Lys Gln Asp Gly Thr Ile Gln Asn Leu
            340                 345                 350

Lys Glu Thr Leu Lys Ser Arg Glu Arg Glu Thr Glu Glu Leu Tyr Gln
        355                 360                 365

Val Ile Glu Gly Gln Asn Asp Thr Met Ala Lys Leu Arg Glu Met Leu
    370                 375                 380

His Gln Ser Gln Leu Gly Gln Leu His Ser Ser Glu Gly Thr Ser Pro
385                 390                 395                 400

Ala Gln Gln Gln Val Ala Leu Leu Asp Leu Gln Ser Ala Leu Phe Cys
                405                 410                 415

Ser Gln Leu Glu Ile Gln Lys Leu Gln Arg Val Val Arg Gln Lys Glu
            420                 425                 430

Arg Gln Leu Ala Asp Ala Lys Gln Cys Val Gln Phe Val Glu Ala Ala
        435                 440                 445

Ala His Glu Ser Glu Gln Gln Lys Glu Ala Ser Trp Lys His Asn Gln
    450                 455                 460

Glu Leu Arg Lys Ala Leu Gln Gln Leu Gln Glu Glu Leu Gln Asn Lys
465                 470                 475                 480

Ser Gln Gln Leu Arg Ala Trp Glu Ala Glu Lys Tyr Asn Glu Ile Arg
                485                 490                 495

Thr Gln Glu Gln Asn Ile Gln His Leu Asn His Ser Leu Ser His Lys
            500                 505                 510

Glu Gln Leu Leu Gln Glu Phe Arg Glu Leu Leu Gln Tyr Arg Asp Asn
        515                 520                 525

Ser Asp Lys Thr Leu Glu Ala Asn Glu Met Leu Leu Glu Lys Leu Arg
    530                 535                 540

Gln Arg Ile His Asp Lys Ala Val Ala Leu Glu Arg Ala Ile Asp Glu
```

-continued

```
545                 550                 555                 560

Lys Phe Ser Ala Leu Glu Glu Lys Glu Lys Glu Leu Arg Gln Leu Arg
                565                 570                 575

Leu Ala Val Arg Glu Arg Asp His Asp Leu Glu Arg Leu Arg Asp Val
            580                 585                 590

Leu Ser Ser Asn Glu Ala Thr Met Gln Ser Met Glu Ser Leu Leu Arg
        595                 600                 605

Ala Lys Gly Leu Glu Val Glu Gln Leu Ser Thr Thr Cys Gln Asn Leu
    610                 615                 620

Gln Trp Leu Lys Glu Glu Met Glu Thr Lys Phe Ser Arg Trp Gln Lys
625                 630                 635                 640

Glu Gln Glu Ser Ile Ile Gln Gln Leu Gln Thr Ser Leu His Asp Arg
                645                 650                 655

Asn Lys Glu Val Glu Asp Leu Ser Ala Thr Leu Leu Cys Lys Leu Gly
            660                 665                 670

Pro Gly Gln Ser Glu Ile Ala Glu Glu Leu Cys Gln Arg Leu Gln Arg
        675                 680                 685

Lys Glu Arg Met Leu Gln Asp Leu Leu Ser Asp Arg Asn Lys Gln Val
    690                 695                 700

Leu Glu His Glu Met Glu Ile Gln Gly Leu Leu Gln Ser Val Ser Thr
705                 710                 715                 720

Arg Glu Gln Glu Ser Gln Ala Ala Ala Glu Lys Leu Val Gln Ala Leu
                725                 730                 735

Met Glu Arg Asn Ser Glu Leu Gln Ala Leu Arg Gln Tyr Leu Gly Gly
            740                 745                 750

Arg Asp Ser Leu Met Ser Gln Ala Pro Ile Ser Asn Gln Gln Ala Glu
        755                 760                 765

Val Thr Pro Thr Gly Cys Leu Gly Lys Gln Thr Asp Gln Gly Ser Met
    770                 775                 780

Gln Ile Pro Ser Arg Asp Asp Ser Thr Ser Leu Thr Ala Lys Glu Asp
785                 790                 795                 800

Val Ser Ile Pro Arg Ser Thr Leu Gly Asp Leu Asp Thr Val Ala Gly
                805                 810                 815

Leu Glu Lys Glu Leu Ser Asn Ala Lys Glu Glu Leu Glu Leu Met Ala
            820                 825                 830

Lys Lys Glu Arg Glu Ser Gln Met Glu Leu Ser Ala Leu Gln Ser Met
        835                 840                 845

Met Ala Val Gln Glu Glu Glu Leu Gln Val Gln Ala Ala Asp Met Glu
    850                 855                 860

Ser Leu Thr Arg Asn Ile Gln Ile Lys Glu Asp Leu Ile Lys Asp Leu
865                 870                 875                 880

Gln Met Gln Leu Val Asp Pro Glu Asp Ile Pro Ala Met Glu Arg Leu
                885                 890                 895

Thr Gln Glu Val Leu Leu Leu Arg Glu Lys Val Ala Ser Val Glu Ser
            900                 905                 910

Gln Gly Gln Glu Ile Ser Gly Asn Arg Arg Gln Gln Leu Leu Leu Met
        915                 920                 925

Leu Glu Gly Leu Val Asp Glu Arg Ser Arg Leu Asn Glu Ala Leu Gln
    930                 935                 940

Ala Glu Arg Gln Leu Tyr Ser Ser Leu Val Lys Phe His Ala His Pro
945                 950                 955                 960

Glu Ser Ser Glu Arg Asp Arg Thr Leu Gln Val Glu Leu Glu Gly Ala
                965                 970                 975
```

```
Gln Val Leu Arg Ser Arg Leu Glu Glu Val Leu Gly Arg Ser Leu Glu
            980                 985                 990

Arg Leu Asn Arg Leu Glu Thr Leu  Ala Ala Ile Gly Gly  Ala Ala Ala
        995                 1000                1005

Gly Asp  Asp Thr Glu Asp Thr  Ser Thr Glu Phe Thr  Asp Ser Ile
    1010                 1015                 1020

Glu Glu  Glu Ala Ala His His  Ser His Gln Gln Leu  Val Lys Val
    1025                 1030                 1035

Ala Leu  Glu Lys Ser Leu Ala  Thr Val Glu Thr Gln  Asn Pro Ser
    1040                 1045                 1050

Phe Ser  Pro Pro Ser Pro Met  Gly Gly Asp Ser Asn  Arg Cys Leu
    1055                 1060                 1065

Gln Glu  Glu Met Leu His Leu  Arg Ala Glu Phe His  Gln His Leu
    1070                 1075                 1080

Glu Glu  Lys Arg Lys Ala Glu  Glu Glu Leu Lys Glu  Leu Lys Ala
    1085                 1090                 1095

Gln Ile  Glu Glu Ala Gly Phe  Ser Ser Val Ser His  Ile Arg Asn
    1100                 1105                 1110

Thr Met  Leu Ser Leu Cys Leu  Glu Asn Ala Glu Leu  Lys Glu Gln
    1115                 1120                 1125

Met Gly  Glu Ala Met Ser Asp  Gly Trp Glu Ile Glu  Glu Asp Lys
    1130                 1135                 1140

Glu Lys  Gly Glu Leu Asp Asn  Gln Ser Gln Pro Arg  Asp Pro Gly
    1145                 1150                 1155

Pro Gln  Ser Ala Phe Ser Leu  Pro Gly Ser Thr Gln  His Leu Arg
    1160                 1165                 1170

Ser Gln  Leu Ser Gln Cys Lys  Gln Arg Tyr Gln Asp  Leu Gln Glu
    1175                 1180                 1185

Lys Leu  Leu Leu Ser Glu Ala  Thr Val Phe Ala Gln  Ala Asn Glu
    1190                 1195                 1200

Leu Glu  Lys Tyr Arg Val Met  Leu Thr Gly Glu Ser  Leu Val Lys
    1205                 1210                 1215

Gln Asp  Ser Lys Gln Ile Gln  Val Asp Leu Gln Asp  Leu Gly Tyr
    1220                 1225                 1230

Glu Thr  Cys Gly Arg Ser Glu  Asn Glu Ala Glu Arg  Glu Glu Thr
    1235                 1240                 1245

Thr Ser  Pro Glu Cys Glu Glu  His Asn Ser Leu Lys  Glu Met Val
    1250                 1255                 1260

Leu Met  Glu Gly Leu Cys Ser  Glu Gln Gly Arg Arg  Gly Ser Thr
    1265                 1270                 1275

Leu Ala  Ser Ser Ser Glu Arg  Lys Pro Leu Glu Asn  Gln Leu Gly
    1280                 1285                 1290

Lys Gln  Glu Glu Phe Arg Val  Tyr Gly Lys Ser Glu  Asn Ile Leu
    1295                 1300                 1305

Val Leu  Arg Lys Asp Ile Lys  Asp Leu Lys Ala Gln  Leu Gln Asn
    1310                 1315                 1320

Ala Asn  Lys Val Ile Gln Asn  Leu Lys Ser Arg Val  Arg Ser Leu
    1325                 1330                 1335

Ser Val  Thr Ser Asp Tyr Ser  Ser Ser Leu Glu Arg  Pro Trp Lys
    1340                 1345                 1350

Leu Arg  Ala Val Gly Thr Leu  Glu Gly Ser Ser Pro  His Ser Val
    1355                 1360                 1365
```

```
Pro Asp  Glu Asp Glu Gly Trp  Leu Ser Asp Gly Thr  Gly Ala Phe
    1370                 1375                 1380

Tyr Ser  Pro Gly Leu Gln Ala  Lys Lys Asp Leu Glu  Ser Leu Ile
    1385                 1390                 1395

Gln Arg  Val Ser Gln Leu Glu  Ala Gln Leu Pro Lys  Asn Gly Leu
    1400                 1405                 1410

Glu Glu  Lys Leu Ala Glu Glu  Leu Arg Ser Ala Ser  Trp Pro Gly
    1415                 1420                 1425

Lys Tyr  Asp Ser Leu Ile Gln  Asp Gln Ala Arg Glu  Leu Ser Tyr
    1430                 1435                 1440

Leu Arg  Gln Lys Ile Arg Glu  Gly Arg Gly Ile Cys  Tyr Leu Ile
    1445                 1450                 1455

Thr Arg  His Ala Lys Asp Thr  Val Lys Ser Phe Glu  Asp Leu Leu
    1460                 1465                 1470

Arg Ser  Asn Asp Ile Asp Tyr  Tyr Leu Gly Gln Ser  Phe Arg Glu
    1475                 1480                 1485

Gln Leu  Ala Gln Gly Ser Gln  Leu Thr Glu Arg Leu  Thr Ser Lys
    1490                 1495                 1500

Leu Ser  Thr Lys Asp His Lys  Ser Glu Lys Asp Gln  Ala Gly Leu
    1505                 1510                 1515

Glu Pro  Leu Ala Leu Arg Leu  Ser Arg Glu Leu Gln  Glu Lys Glu
    1520                 1525                 1530

Lys Val  Ile Glu Val Leu Gln  Ala Lys Leu Asp Ala  Arg Ser Leu
    1535                 1540                 1545

Thr Pro  Ser Ser Ser His Ala  Leu Ser Asp Ser His  Arg Ser Pro
    1550                 1555                 1560

Ser Ser  Thr Ser Phe Leu Ser  Asp Glu Leu Glu Ala  Cys Ser Asp
    1565                 1570                 1575

Met Asp  Ile Val Ser Glu Tyr  Thr His Tyr Glu Glu  Lys Lys Ala
    1580                 1585                 1590

Ser Pro  Ser His Ser Asp Ser  Ile His His Ser Ser  His Ser Ala
    1595                 1600                 1605

Val Leu  Ser Ser Lys Pro Ser  Ser Thr Ser Ala Ser  Gln Gly Ala
    1610                 1615                 1620

Lys Ala  Glu Ser Asn Ser Asn  Pro Ile Ser Leu Pro  Thr Pro Gln
    1625                 1630                 1635

Asn Thr  Pro Lys Glu Ala Asn  Gln Ala His Ser Gly  Ala Ser Thr
    1640                 1645                 1650

Val Pro  Pro Ala Ser Thr Ala  Thr Leu Leu Ser Asn  Asp Leu Glu
    1655                 1660                 1665

Ala Asp  Ser Ser Tyr Tyr Leu  Asn Ser Ala Gln Pro  His Ser Pro
    1670                 1675                 1680

Pro Arg  Gly Thr Ile Glu Leu  Gly Arg Ile Leu Glu  Pro Gly Tyr
    1685                 1690                 1695

Leu Gly  Ser Ser Gly Lys Trp  Asp Val Met Arg Pro  Gln Lys Gly
    1700                 1705                 1710

Ser Val  Ser Gly Asp Leu Ser  Ser Gly Ser Ser Val  Tyr Gln Leu
    1715                 1720                 1725

Asn Ser  Lys Pro Thr Gly Ala  Asp Leu Leu Glu Glu  His Leu Gly
    1730                 1735                 1740

Glu Ile  Arg Asn Leu Arg Gln  Arg Leu Glu Glu Ser  Ile Cys Ile
    1745                 1750                 1755

Asn Asp  Arg Leu Arg Glu Gln  Leu Glu His Arg Leu  Thr Ser Thr
```

```
    1760                1765                1770

Ala Arg  Gly Arg Gly Ser Thr  Ser Asn Phe Tyr Ser  Gln Gly Leu
    1775                1780                1785

Glu Ser  Ile Pro Gln Leu Cys  Asn Glu Asn Arg Val  Leu Arg Glu
    1790                1795                1800

Asp Asn  Arg Arg Leu Gln Ala  Gln Leu Ser His Val  Ser Arg Glu
    1805                1810                1815

His Ser  Gln Glu Thr Glu Ser  Leu Arg Glu Ala Leu  Leu Ser Ser
    1820                1825                1830

Arg Ser  His Leu Gln Glu Leu  Glu Lys Glu Leu Glu  His Gln Lys
    1835                1840                1845

Val Glu  Arg Gln Gln Leu Leu  Glu Asp Leu Arg Glu  Lys Gln Gln
    1850                1855                1860

Glu Val  Leu His Phe Arg Glu  Glu Arg Leu Ser Leu  Gln Glu Asn
    1865                1870                1875

Asp Ser  Arg Leu Gln His Lys  Leu Val Leu Leu Gln  Gln Gln Cys
    1880                1885                1890

Glu Glu  Lys Gln Gln Leu Phe  Glu Ser Leu Gln Ser  Glu Leu Gln
    1895                1900                1905

Ile Tyr  Glu Ala Leu Tyr Gly  Asn Ser Lys Lys Gly  Leu Lys Ala
    1910                1915                1920

Tyr Ser  Leu Asp Ala Cys His  Gln Ile Pro Leu Ser  Ser Asp Leu
    1925                1930                1935

Ser His  Leu Val Ala Glu Val  Arg Ala Leu Arg Gly  Gln Leu Glu
    1940                1945                1950

Gln Ser  Ile Gln Gly Asn Asn  Cys Leu Arg Leu Gln  Leu Gln Gln
    1955                1960                1965

Gln Leu  Glu Ser Gly Ala Gly  Lys Ala Ser Leu Ser  Pro Ser Ser
    1970                1975                1980

Ile Asn  Gln Asn Phe Pro Ala  Ser Thr Asp Pro Gly  Asn Lys Gln
    1985                1990                1995

Leu Leu  Leu Gln Asp Ser Ala  Val Ser Pro Pro Val  Arg Asp Val
    2000                2005                2010

Gly Met  Asn Ser Pro Ala Leu  Val Phe Pro Ser Ser  Ala Ser Ser
    2015                2020                2025

Thr Pro  Gly Ser Glu Thr Pro  Ile Ile Asn Arg Ala  Asn Gly Leu
    2030                2035                2040

Gly Leu  Asp Thr Ser Pro Val  Met Lys Thr Pro Pro  Lys Leu Glu
    2045                2050                2055

Gly Asp  Ala Thr Asp Gly Ser  Phe Ala Asn Lys His  Gly Arg His
    2060                2065                2070

Val Ile  Gly His Ile Asp Asp  Tyr Ser Ala Leu Arg  Gln Gln Ile
    2075                2080                2085

Ala Glu  Gly Lys Leu Leu Val  Lys Lys Ile Val Ser  Leu Val Arg
    2090                2095                2100

Ser Ala  Cys Ser Phe Pro Gly  Leu Glu Ala Gln Gly  Thr Glu Val
    2105                2110                2115

Leu Gly  Ser Lys Gly Ile His  Glu Leu Arg Ser Ser  Thr Ser Ala
    2120                2125                2130

Leu His  His Ala Leu Glu Glu  Ser Ala Ser Leu Leu  Thr Met Phe
    2135                2140                2145

Trp Arg  Ala Ala Leu Pro Ser  Thr His Ile Pro Val  Leu Pro Gly
    2150                2155                2160
```

```
Lys Val  Gly Glu Ser Thr Glu  Arg Glu Leu Leu Glu  Leu Arg Thr
    2165                 2170                 2175

Lys Val  Ser Lys Gln Glu Arg  Leu Leu Gln Ser Thr  Thr Glu His
    2180                 2185                 2190

Leu Lys  Asn Ala Asn Gln Gln  Lys Glu Ser Met Glu  Gln Phe Ile
    2195                 2200                 2205

Val Ser  Gln Leu Thr Arg Thr  His Asp Val Leu Lys  Lys Ala Arg
    2210                 2215                 2220

Thr Asn  Leu Glu Val Lys Ser  Leu Arg Ala Leu Pro  Cys Thr Pro
    2225                 2230                 2235

Ala Leu
    2240


<210> SEQ ID NO 11
<211> LENGTH: 2362
<212> TYPE: PRT
<213> ORGANISM: Homo sapiens

<400> SEQUENCE: 11

Met Ser Asn Gly Tyr Arg Thr Leu Ser Gln His Leu Asn Asp Leu Lys
1               5                   10                  15

Lys Glu Asn Phe Ser Leu Lys Leu Arg Ile Tyr Phe Leu Glu Glu Arg
            20                  25                  30

Met Gln Gln Lys Tyr Glu Ala Ser Arg Glu Asp Ile Tyr Lys Arg Asn
        35                  40                  45

Ile Glu Leu Lys Val Glu Val Glu Ser Leu Lys Arg Glu Leu Gln Asp
    50                  55                  60

Lys Lys Gln His Leu Asp Lys Thr Trp Ala Asp Val Glu Asn Leu Asn
65                  70                  75                  80

Ser Gln Asn Glu Ala Glu Leu Arg Arg Gln Phe Glu Glu Arg Gln Gln
                85                  90                  95

Glu Thr Glu His Val Tyr Glu Leu Leu Glu Asn Lys Ile Gln Leu Leu
            100                 105                 110

Gln Glu Glu Ser Arg Leu Ala Lys Asn Glu Ala Ala Arg Met Ala Ala
        115                 120                 125

Leu Val Glu Ala Glu Lys Glu Cys Asn Leu Glu Leu Ser Glu Lys Leu
    130                 135                 140

Lys Gly Val Thr Lys Asn Trp Glu Asp Val Pro Gly Asp Gln Val Lys
145                 150                 155                 160

Pro Asp Gln Tyr Thr Glu Ala Leu Ala Gln Arg Asp Lys Arg Ile Glu
                165                 170                 175

Glu Leu Asn Gln Ser Leu Ala Ala Gln Glu Arg Leu Val Glu Gln Leu
            180                 185                 190

Ser Arg Glu Lys Gln Gln Leu Leu His Leu Leu Glu Glu Pro Thr Ser
        195                 200                 205

Met Glu Val Gln Pro Met Thr Glu Glu Leu Leu Lys Gln Gln Lys Leu
    210                 215                 220

Asn Ser His Glu Thr Thr Ile Thr Gln Gln Ser Val Ser Asp Ser His
225                 230                 235                 240

Leu Ala Glu Leu Gln Glu Lys Ile Gln Gln Thr Glu Ala Thr Asn Lys
                245                 250                 255

Ile Leu Gln Glu Lys Leu Asn Glu Met Ser Tyr Glu Leu Lys Cys Ala
            260                 265                 270

Gln Glu Ser Ser Gln Lys Gln Asp Gly Thr Ile Gln Asn Leu Lys Glu
```

```
        275                 280                 285

Thr Leu Lys Ser Arg Glu Arg Glu Thr Glu Glu Leu Tyr Gln Val Ile
    290                 295                 300

Glu Gly Gln Asn Asp Thr Met Ala Lys Leu Arg Glu Met Leu His Gln
305                 310                 315                 320

Ser Gln Leu Gly Gln Leu His Ser Ser Glu Gly Thr Ser Pro Ala Gln
                325                 330                 335

Gln Gln Val Ala Leu Leu Asp Leu Gln Ser Ala Leu Phe Cys Ser Gln
            340                 345                 350

Leu Glu Ile Gln Lys Leu Gln Arg Val Val Arg Gln Lys Glu Arg Gln
        355                 360                 365

Leu Ala Asp Ala Lys Gln Cys Val Gln Phe Val Glu Ala Ala Ala His
    370                 375                 380

Glu Ser Glu Gln Gln Lys Glu Ala Ser Trp Lys His Asn Gln Glu Leu
385                 390                 395                 400

Arg Lys Ala Leu Gln Gln Leu Gln Glu Glu Leu Gln Asn Lys Ser Gln
                405                 410                 415

Gln Leu Arg Ala Trp Glu Ala Glu Lys Tyr Asn Glu Ile Arg Thr Gln
            420                 425                 430

Glu Gln Asn Ile Gln His Leu Asn His Ser Leu Ser His Lys Glu Gln
        435                 440                 445

Leu Leu Gln Glu Phe Arg Glu Leu Leu Gln Tyr Arg Asp Asn Ser Asp
    450                 455                 460

Lys Thr Leu Glu Ala Asn Glu Met Leu Leu Glu Lys Leu Arg Gln Arg
465                 470                 475                 480

Ile His Asp Lys Ala Val Ala Leu Glu Arg Ala Ile Asp Glu Lys Phe
                485                 490                 495

Ser Ala Leu Glu Glu Lys Glu Lys Glu Leu Arg Gln Leu Arg Leu Ala
            500                 505                 510

Val Arg Glu Arg Asp His Asp Leu Glu Arg Leu Arg Asp Val Leu Ser
        515                 520                 525

Ser Asn Glu Ala Thr Met Gln Ser Met Glu Ser Leu Leu Arg Ala Lys
    530                 535                 540

Gly Leu Glu Val Glu Gln Leu Ser Thr Thr Cys Gln Asn Leu Gln Trp
545                 550                 555                 560

Leu Lys Glu Glu Met Glu Thr Lys Phe Ser Arg Trp Gln Lys Glu Gln
                565                 570                 575

Glu Ser Ile Ile Gln Gln Leu Gln Thr Ser Leu His Asp Arg Asn Lys
            580                 585                 590

Glu Val Glu Asp Leu Ser Ala Thr Leu Leu Cys Lys Leu Gly Pro Gly
        595                 600                 605

Gln Ser Glu Ile Ala Glu Glu Leu Cys Gln Arg Leu Gln Arg Lys Glu
    610                 615                 620

Arg Met Leu Gln Asp Leu Leu Ser Asp Arg Asn Lys Gln Val Leu Glu
625                 630                 635                 640

His Glu Met Glu Ile Gln Gly Leu Leu Gln Ser Val Ser Thr Arg Glu
                645                 650                 655

Gln Glu Ser Gln Ala Ala Ala Glu Lys Leu Val Gln Ala Leu Met Glu
            660                 665                 670

Arg Asn Ser Glu Leu Gln Ala Leu Arg Gln Tyr Leu Gly Gly Arg Asp
        675                 680                 685

Ser Leu Met Ser Gln Ala Pro Ile Ser Asn Gln Gln Ala Glu Val Thr
    690                 695                 700
```

-continued

```
Pro Thr Gly Cys Leu Gly Lys Gln Thr Asp Gln Gly Ser Met Gln Ile
705                 710                 715                 720

Pro Ser Arg Asp Asp Ser Thr Ser Leu Thr Ala Lys Glu Asp Val Ser
                725                 730                 735

Ile Pro Arg Ser Thr Leu Gly Asp Leu Asp Thr Val Ala Gly Leu Glu
            740                 745                 750

Lys Glu Leu Ser Asn Ala Lys Glu Glu Leu Glu Leu Met Ala Lys Lys
        755                 760                 765

Glu Arg Glu Ser Gln Met Glu Leu Ser Ala Leu Gln Ser Met Met Ala
    770                 775                 780

Val Gln Glu Glu Glu Leu Gln Val Gln Ala Ala Asp Met Glu Ser Leu
785                 790                 795                 800

Thr Arg Asn Ile Gln Ile Lys Glu Asp Leu Ile Lys Asp Leu Gln Met
                805                 810                 815

Gln Leu Val Asp Pro Glu Asp Ile Pro Ala Met Glu Arg Leu Thr Gln
            820                 825                 830

Glu Val Leu Leu Leu Arg Glu Lys Val Ala Ser Val Glu Ser Gln Gly
        835                 840                 845

Gln Glu Ile Ser Gly Asn Arg Arg Gln Gln Leu Leu Leu Met Leu Glu
    850                 855                 860

Gly Leu Val Asp Glu Arg Ser Arg Leu Asn Glu Ala Leu Gln Ala Glu
865                 870                 875                 880

Arg Gln Leu Tyr Ser Ser Leu Val Lys Phe His Ala His Pro Glu Ser
                885                 890                 895

Ser Glu Arg Asp Arg Thr Leu Gln Val Glu Leu Glu Gly Ala Gln Val
            900                 905                 910

Leu Arg Ser Arg Leu Glu Glu Val Leu Gly Arg Ser Leu Glu Arg Leu
        915                 920                 925

Asn Arg Leu Glu Thr Leu Ala Ala Ile Gly Gly Ala Ala Ala Gly Asp
    930                 935                 940

Asp Thr Glu Asp Thr Ser Thr Glu Phe Thr Asp Ser Ile Glu Glu Glu
945                 950                 955                 960

Ala Ala His His Ser His Gln Gln Leu Val Lys Val Ala Leu Glu Lys
                965                 970                 975

Ser Leu Ala Thr Val Glu Thr Gln Asn Pro Ser Phe Ser Pro Pro Ser
            980                 985                 990

Pro Met Gly Gly Asp Ser Asn Arg  Cys Leu Gln Glu Glu  Met Leu His
        995                 1000                1005

Leu Arg  Ala Glu Phe His Gln  His Leu Glu Glu Lys  Arg Lys Ala
    1010                1015                1020

Glu Glu  Glu Leu Lys Glu Leu  Lys Ala Gln Ile Glu  Glu Ala Gly
    1025                1030                1035

Phe Ser  Ser Val Ser His Ile  Arg Asn Thr Met Leu  Ser Leu Cys
    1040                1045                1050

Leu Glu  Asn Ala Glu Leu Lys  Glu Gln Met Gly Glu  Ala Met Ser
    1055                1060                1065

Asp Gly  Trp Glu Ile Glu Glu  Asp Lys Glu Lys Gly  Glu Val Met
    1070                1075                1080

Val Glu  Thr Val Val Thr Lys  Glu Gly Leu Ser Glu  Ser Ser Leu
    1085                1090                1095

Gln Ala  Glu Phe Arg Lys Leu  Gln Gly Lys Leu Lys  Asn Ala His
    1100                1105                1110
```

```
Asn Ile  Ile Asn Leu Leu Lys  Glu Gln Leu Val Leu  Ser Ser Lys
    1115                 1120                 1125

Glu Gly  Asn Ser Lys Leu Thr  Pro Glu Leu Leu Val  His Leu Thr
    1130                 1135                 1140

Ser Thr  Ile Glu Arg Ile Asn  Thr Glu Leu Val Gly  Ser Pro Gly
    1145                 1150                 1155

Lys His  Gln His Gln Glu Glu  Gly Asn Val Thr Val  Arg Pro Phe
    1160                 1165                 1170

Pro Arg  Pro Gln Ser Leu Asp  Leu Gly Ala Thr Phe  Thr Val Asp
    1175                 1180                 1185

Ala His  Gln Leu Asp Asn Gln  Ser Gln Pro Arg Asp  Pro Gly Pro
    1190                 1195                 1200

Gln Ser  Ala Phe Ser Leu Pro  Gly Ser Thr Gln His  Leu Arg Ser
    1205                 1210                 1215

Gln Leu  Ser Gln Cys Lys Gln  Arg Tyr Gln Asp Leu  Gln Glu Lys
    1220                 1225                 1230

Leu Leu  Leu Ser Glu Ala Thr  Val Phe Ala Gln Ala  Asn Glu Leu
    1235                 1240                 1245

Glu Lys  Tyr Arg Val Met Leu  Thr Gly Glu Ser Leu  Val Lys Gln
    1250                 1255                 1260

Asp Ser  Lys Gln Ile Gln Val  Asp Leu Gln Asp Leu  Gly Tyr Glu
    1265                 1270                 1275

Thr Cys  Gly Arg Ser Glu Asn  Glu Ala Glu Arg Glu  Glu Thr Thr
    1280                 1285                 1290

Ser Pro  Glu Cys Glu Glu His  Asn Ser Leu Lys Glu  Met Val Leu
    1295                 1300                 1305

Met Glu  Gly Leu Cys Ser Glu  Gln Gly Arg Arg Gly  Ser Thr Leu
    1310                 1315                 1320

Ala Ser  Ser Ser Glu Arg Lys  Pro Leu Glu Asn Gln  Leu Gly Lys
    1325                 1330                 1335

Gln Glu  Glu Phe Arg Val Tyr  Gly Lys Ser Glu Asn  Ile Leu Val
    1340                 1345                 1350

Leu Arg  Lys Asp Ile Lys Asp  Leu Lys Ala Gln Leu  Gln Asn Ala
    1355                 1360                 1365

Asn Lys  Val Ile Gln Asn Leu  Lys Ser Arg Val Arg  Ser Leu Ser
    1370                 1375                 1380

Val Thr  Ser Asp Tyr Ser Ser  Ser Leu Glu Arg Pro  Trp Lys Leu
    1385                 1390                 1395

Arg Ala  Val Gly Thr Leu Glu  Gly Ser Ser Pro His  Ser Val Pro
    1400                 1405                 1410

Asp Glu  Asp Glu Gly Trp Leu  Ser Asp Gly Thr Gly  Ala Phe Tyr
    1415                 1420                 1425

Ser Pro  Gly Leu Gln Ala Lys  Lys Asp Leu Glu Ser  Leu Ile Gln
    1430                 1435                 1440

Arg Val  Ser Gln Leu Glu Ala  Gln Leu Pro Lys Asn  Gly Leu Glu
    1445                 1450                 1455

Glu Lys  Leu Ala Glu Glu Leu  Arg Ser Ala Ser Trp  Pro Gly Lys
    1460                 1465                 1470

Tyr Asp  Ser Leu Ile Gln Asp  Gln Ala Arg Glu Leu  Ser Tyr Leu
    1475                 1480                 1485

Arg Gln  Lys Ile Arg Glu Gly  Arg Gly Ile Cys Tyr  Leu Ile Thr
    1490                 1495                 1500

Arg His  Ala Lys Asp Thr Val  Lys Ser Phe Glu Asp  Leu Leu Arg
```

```
    1505                1510                1515

Ser Asn  Asp Ile Asp Tyr Tyr  Leu Gly Gln Ser Phe  Arg Glu Gln
    1520                1525                1530

Leu Ala  Gln Gly Ser Gln Leu  Thr Glu Arg Leu Thr  Ser Lys Leu
    1535                1540                1545

Ser Thr  Lys Asp His Lys Ser  Glu Lys Asp Gln Ala  Gly Leu Glu
    1550                1555                1560

Pro Leu  Ala Leu Arg Leu Ser  Arg Glu Leu Gln Glu  Lys Glu Lys
    1565                1570                1575

Val Ile  Glu Val Leu Gln Ala  Lys Leu Asp Ala Arg  Ser Leu Thr
    1580                1585                1590

Pro Ser  Ser Ser His Ala Leu  Ser Asp Ser His Arg  Ser Pro Ser
    1595                1600                1605

Ser Thr  Ser Phe Leu Ser Asp  Glu Leu Glu Ala Cys  Ser Asp Met
    1610                1615                1620

Asp Ile  Val Ser Glu Tyr Thr  His Tyr Glu Glu Lys  Lys Ala Ser
    1625                1630                1635

Pro Ser  His Ser Asp Ser Ile  His His Ser Ser His  Ser Ala Val
    1640                1645                1650

Leu Ser  Ser Lys Pro Ser Ser  Thr Ser Ala Ser Gln  Gly Ala Lys
    1655                1660                1665

Ala Glu  Ser Asn Ser Asn Pro  Ile Ser Leu Pro Thr  Pro Gln Asn
    1670                1675                1680

Thr Pro  Lys Glu Ala Asn Gln  Ala His Ser Gly Phe  His Phe His
    1685                1690                1695

Ser Ile  Pro Lys Leu Ala Ser  Leu Pro Gln Ala Pro  Leu Pro Ser
    1700                1705                1710

Ala Pro  Ser Ser Phe Leu Pro  Phe Ser Pro Thr Gly  Pro Leu Leu
    1715                1720                1725

Leu Gly  Cys Cys Glu Thr Pro  Val Val Ser Leu Ala  Glu Ala Gln
    1730                1735                1740

Gln Glu  Leu Gln Met Leu Gln  Lys Gln Leu Gly Glu  Ser Ala Ser
    1745                1750                1755

Thr Val  Pro Pro Ala Ser Thr  Ala Thr Leu Leu Ser  Asn Asp Leu
    1760                1765                1770

Glu Ala  Asp Ser Ser Tyr Tyr  Leu Asn Ser Ala Gln  Pro His Ser
    1775                1780                1785

Pro Pro  Arg Gly Thr Ile Glu  Leu Gly Arg Ile Leu  Glu Pro Gly
    1790                1795                1800

Tyr Leu  Gly Ser Ser Gly Lys  Trp Asp Val Met Arg  Pro Gln Lys
    1805                1810                1815

Gly Ser  Val Ser Gly Asp Leu  Ser Ser Gly Ser Ser  Val Tyr Gln
    1820                1825                1830

Leu Asn  Ser Lys Pro Thr Gly  Ala Asp Leu Leu Glu  Glu His Leu
    1835                1840                1845

Gly Glu  Ile Arg Asn Leu Arg  Gln Arg Leu Glu Glu  Ser Ile Cys
    1850                1855                1860

Ile Asn  Asp Arg Leu Arg Glu  Gln Leu Glu His Arg  Leu Thr Ser
    1865                1870                1875

Thr Ala  Arg Gly Arg Gly Ser  Thr Ser Asn Phe Tyr  Ser Gln Gly
    1880                1885                1890

Leu Glu  Ser Ile Pro Gln Leu  Cys Asn Glu Asn Arg  Val Leu Arg
    1895                1900                1905
```

```
Glu Asp  Asn Arg Arg Leu Gln  Ala Gln Leu Ser His  Val Ser Arg
    1910                 1915                 1920

Glu His  Ser Gln Glu Thr Glu  Ser Leu Arg Glu Ala  Leu Leu Ser
    1925                 1930                 1935

Ser Arg  Ser His Leu Gln Glu  Leu Glu Lys Glu Leu  Glu His Gln
    1940                 1945                 1950

Lys Val  Glu Arg Gln Gln Leu  Leu Glu Asp Leu Arg  Glu Lys Gln
    1955                 1960                 1965

Gln Glu  Val Leu His Phe Arg  Glu Glu Arg Leu Ser  Leu Gln Glu
    1970                 1975                 1980

Asn Asp  Ser Arg Leu Gln His  Lys Leu Val Leu Leu  Gln Gln Gln
    1985                 1990                 1995

Cys Glu  Glu Lys Gln Gln Leu  Phe Glu Ser Leu Gln  Ser Glu Leu
    2000                 2005                 2010

Gln Ile  Tyr Glu Ala Leu Tyr  Gly Asn Ser Lys Lys  Gly Leu Lys
    2015                 2020                 2025

Ala Tyr  Ser Leu Asp Ala Cys  His Gln Ile Pro Leu  Ser Ser Asp
    2030                 2035                 2040

Leu Ser  His Leu Val Ala Glu  Val Arg Ala Leu Arg  Gly Gln Leu
    2045                 2050                 2055

Glu Gln  Ser Ile Gln Gly Asn  Asn Cys Leu Arg Leu  Gln Leu Gln
    2060                 2065                 2070

Gln Gln  Leu Glu Ser Gly Ala  Gly Lys Ala Ser Leu  Ser Pro Ser
    2075                 2080                 2085

Ser Ile  Asn Gln Asn Phe Pro  Ala Ser Thr Asp Pro  Gly Asn Lys
    2090                 2095                 2100

Gln Leu  Leu Leu Gln Asp Ser  Ala Val Ser Pro Pro  Val Arg Asp
    2105                 2110                 2115

Val Gly  Met Asn Ser Pro Ala  Leu Val Phe Pro Ser  Ser Ala Ser
    2120                 2125                 2130

Ser Thr  Pro Gly Ser Glu Thr  Pro Ile Ile Asn Arg  Ala Asn Gly
    2135                 2140                 2145

Leu Gly  Leu Asp Thr Ser Pro  Val Met Lys Thr Pro  Pro Lys Leu
    2150                 2155                 2160

Glu Gly  Asp Ala Thr Asp Gly  Ser Phe Ala Asn Lys  His Gly Arg
    2165                 2170                 2175

His Val  Ile Gly His Ile Asp  Asp Tyr Ser Ala Leu  Arg Gln Gln
    2180                 2185                 2190

Ile Ala  Glu Gly Lys Leu Leu  Val Lys Lys Ile Val  Ser Leu Val
    2195                 2200                 2205

Arg Ser  Ala Cys Ser Phe Pro  Gly Leu Glu Ala Gln  Gly Thr Glu
    2210                 2215                 2220

Val Leu  Gly Ser Lys Gly Ile  His Glu Leu Arg Ser  Ser Thr Ser
    2225                 2230                 2235

Ala Leu  His His Ala Leu Glu  Glu Ser Ala Ser Leu  Leu Thr Met
    2240                 2245                 2250

Phe Trp  Arg Ala Ala Leu Pro  Ser Thr His Ile Pro  Val Leu Pro
    2255                 2260                 2265

Gly Lys  Val Gly Glu Ser Thr  Glu Arg Glu Leu Leu  Glu Leu Arg
    2270                 2275                 2280

Thr Lys  Val Ser Lys Gln Glu  Arg Leu Leu Gln Ser  Thr Thr Glu
    2285                 2290                 2295
```

```
His Leu  Lys Asn Ala Asn Gln  Gln Lys Glu Ser Met  Glu Gln Phe
    2300                 2305                 2310

Ile Val  Ser Gln Leu Thr Arg  Thr His Asp Val Leu  Lys Lys Ala
    2315                 2320                 2325

Arg Thr  Asn Leu Glu Glu Pro  Cys Lys Lys Arg Ser  His Gln Lys
    2330                 2335                 2340

Ser Leu  Lys Gln Gln Glu Arg  Trp Ala Cys Pro Pro  Phe Val Gln
    2345                 2350                 2355

Leu Pro  Ile Cys
    2360


<210> SEQ ID NO 12
<211> LENGTH: 1113
<212> TYPE: PRT
<213> ORGANISM: Pongo abelii

<400> SEQUENCE: 12

Met Lys Glu Ile Cys Arg Ile Cys Ala Arg Glu Leu Cys Gly Asn Gln
1               5                   10                  15

Arg Arg Trp Ile Phe His Thr Ala Ser Lys Leu Asn Leu Gln Val Leu
            20                  25                  30

Leu Ser His Val Leu Gly Lys Asp Val Pro Arg Asp Gly Lys Ala Glu
        35                  40                  45

Phe Ala Cys Ser Lys Cys Ala Phe Met Leu Asp Arg Ile Tyr Arg Phe
    50                  55                  60

Asp Thr Val Ile Ala Arg Ile Glu Ala Leu Ser Ile Glu Arg Leu Gln
65                  70                  75                  80

Lys Leu Leu Leu Glu Lys Asp Arg Leu Lys Phe Cys Ile Ala Ser Met
                85                  90                  95

Tyr Arg Lys Asn Asn Asp Asp Ser Gly Ala Glu Ile Lys Ala Gly Asn
            100                 105                 110

Gly Thr Val Asp Met Ser Val Leu Pro Asp Ala Arg Tyr Ser Ala Leu
        115                 120                 125

Leu Gln Glu Asp Phe Ala Tyr Ser Gly Phe Glu Cys Trp Met Glu Asn
    130                 135                 140

Glu Asp Gln Ile Gln Glu Pro His Ser Cys His Gly Ser Glu Gly Pro
145                 150                 155                 160

Gly Asn Arg Pro Arg Arg Cys Arg Gly Cys Ala Ala Leu Arg Val Ala
                165                 170                 175

Asp Ser Asp Tyr Glu Ala Ile Cys Lys Val Pro Arg Lys Val Ala Arg
            180                 185                 190

Ser Ile Ser Cys Gly Pro Ser Ser Arg Trp Ser Thr Ser Ile Cys Thr
        195                 200                 205

Glu Glu Pro Ala Leu Ser Glu Val Gly Pro Pro Asp Leu Ala Ser Thr
    210                 215                 220

Lys Val Pro Pro Asp Gly Glu Ser Met Glu Glu Glu Thr Pro Gly Ser
225                 230                 235                 240

Ser Val Glu Ser Leu Asp Ala Ser Val Gln Ala Ser Pro Pro Gln Gln
                245                 250                 255

Lys Asp Glu Glu Thr Glu Arg Ser Ala Lys Glu Leu Gly Lys Cys Asp
            260                 265                 270

Cys Cys Ser Asp Asp Gln Ala Pro Gln His Gly Trp Leu Glu Leu Ala
        275                 280                 285

Leu Ser Met Ile Lys Gly Leu Asp Tyr Lys Pro Ile Gln Ser Pro Arg
    290                 295                 300
```

```
Gly Ser Arg Leu Pro Ile Pro Val Lys Ser Ser Pro Pro Gly Ala Lys
305                 310                 315                 320

Pro Gly Pro Ser Met Thr Asp Gly Val Ser Ser Gly Phe Leu Asn Arg
                325                 330                 335

Ser Leu Lys Pro Leu Tyr Lys Thr Pro Val Ser Tyr Pro Leu Glu Leu
            340                 345                 350

Ser Asp Leu Gln Glu Leu Trp Asp Asp Leu Cys Glu Asp Tyr Leu Pro
        355                 360                 365

Leu Arg Val Gln Pro Met Thr Glu Glu Leu Leu Lys Gln Gln Lys Leu
    370                 375                 380

Asn Ser His Glu Thr Thr Ile Thr Gln Gln Ser Val Ser Asp Ser His
385                 390                 395                 400

Leu Ala Glu Leu Gln Glu Asn Ile Gln Gln Thr Glu Ala Thr Asn Lys
                405                 410                 415

Ile Leu Gln Glu Lys Leu Asn Glu Met Ser Tyr Glu Leu Lys Cys Ala
            420                 425                 430

Gln Glu Ser Ser Gln Lys Gln Asp Gly Thr Ile Gln Asn Leu Lys Glu
        435                 440                 445

Thr Leu Lys Ser Arg Glu Arg Glu Thr Glu Glu Leu Tyr Gln Val Ile
    450                 455                 460

Glu Gly Gln Asn Asp Thr Met Ala Lys Leu Arg Glu Met Leu His Gln
465                 470                 475                 480

Ser Gln Leu Gly Gln Leu His Ser Ser Glu Asp Ala Ser Pro Ala Gln
                485                 490                 495

Gln Gln Val Ala Leu Leu Asp Leu Gln Ser Ala Leu Phe Cys Cys Gln
            500                 505                 510

Leu Glu Ile Gln Lys Leu Gln Arg Val Val Arg Gln Lys Glu Arg Gln
        515                 520                 525

Leu Ala Asp Ala Lys Gln Cys Val Gln Phe Val Glu Ala Ala Ala His
    530                 535                 540

Glu Ser Glu Gln Gln Lys Glu Ala Ser Trp Lys His Asn Gln Glu Leu
545                 550                 555                 560

Arg Lys Ala Leu Gln Gln Leu Gln Glu Glu Leu Gln Asn Lys Ser Gln
                565                 570                 575

Gln Leu Arg Ala Arg Glu Ala Glu Lys Tyr Asn Glu Ile Arg Thr Gln
            580                 585                 590

Glu Gln Asn Ile Gln His Leu Asn His Ser Leu Ser His Lys Glu Gln
        595                 600                 605

Leu Leu Gln Glu Phe Arg Glu Leu Leu Gln Tyr Arg Asp Asn Ser Asp
    610                 615                 620

Lys Thr Leu Glu Ala Asn Glu Met Leu Leu Glu Lys Leu Arg Gln Arg
625                 630                 635                 640

Ile His Asp Lys Ala Val Ala Leu Glu Arg Ala Ile Asp Glu Lys Phe
                645                 650                 655

Ser Ala Leu Glu Glu Lys Glu Lys Glu Leu Arg Gln Leu Arg Leu Ala
            660                 665                 670

Val Arg Glu Arg Asp His Asp Leu Glu Arg Leu Arg Gly Val Leu Ser
        675                 680                 685

Ser Asn Glu Ala Thr Met Gln Ser Met Glu Ser Leu Leu Arg Ala Lys
    690                 695                 700

Gly Leu Glu Val Glu Gln Leu Ser Thr Thr Cys Gln Asn Leu Gln Trp
705                 710                 715                 720
```

```
Leu Lys Glu Glu Met Glu Thr Lys Phe Ser His Trp Gln Lys Glu Gln
                725                 730                 735

Glu Ser Ile Ile Gln Gln Leu Gln Thr Ser Leu His Asp Arg Asn Lys
            740                 745                 750

Glu Val Glu Asp Leu Ser Ala Thr Leu Leu Cys Lys Leu Gly Pro Gly
        755                 760                 765

Gln Ser Glu Ile Ala Glu Glu Leu Cys Gln Arg Leu Gln Arg Lys Glu
    770                 775                 780

Arg Met Leu Gln Asp Leu Leu Ser Asp Arg Asn Lys Gln Val Val Glu
785                 790                 795                 800

His Glu Met Glu Ile Gln Gly Leu Leu Gln Ser Met Ser Thr Arg Glu
                805                 810                 815

Gln Glu Ser Gln Ala Ala Ala Glu Lys Met Val Gln Ala Leu Met Glu
            820                 825                 830

Arg Asn Ser Glu Leu Gln Ala Leu Arg Gln Tyr Phe Gly Gly Arg Asp
        835                 840                 845

Ser Leu Met Ser Gln Thr Pro Ile Ser Asn Gln Gln Ala Glu Val Thr
    850                 855                 860

Pro Thr Gly Arg Leu Gly Glu Gln Thr Asp Gln Gly Ser Met Gln Ile
865                 870                 875                 880

Pro Ser Arg Asp Asp Ser Thr Ser Leu Thr Ala Lys Glu Asp Ala Ser
                885                 890                 895

Ile Pro Arg Ser Thr Leu Gly Asp Leu Asp Thr Val Ala Gly Leu Glu
            900                 905                 910

Lys Glu Leu Ser Asn Ala Lys Glu Glu Leu Glu Leu Met Ala Lys Lys
        915                 920                 925

Glu Arg Glu Ser Gln Met Glu Leu Ser Ala Leu Gln Ser Met Met Ala
    930                 935                 940

Val Gln Glu Glu Glu Leu Gln Val Gln Ala Ala Asp Met Glu Ser Leu
945                 950                 955                 960

Ser Arg Asn Ile Gln Ile Lys Glu Asp Leu Ile Lys Asp Leu Gln Met
                965                 970                 975

Gln Leu Val Asp Pro Glu Asp Ile Pro Ala Met Glu Arg Leu Thr Gln
            980                 985                 990

Glu Val Leu Leu Leu Arg Glu Lys  Val Ala Ser Ile Glu  Ser Gln Gly
        995                 1000                1005

Gln Glu  Ile Ser Gly Asn Arg  Arg Gln Gln Leu Leu  Leu Met Leu
    1010                1015                1020

Glu Gly  Leu Val Asp Glu Arg  Ser Arg Leu Asn Glu  Ala Leu Gln
    1025                1030                1035

Ala Glu  Arg Gln Leu Tyr Ser  Ser Leu Val Lys Phe  His Ala His
    1040                1045                1050

Pro Glu  Ser Ser Glu Arg Asp  Arg Thr Leu Gln Val  Glu Leu Glu
    1055                1060                1065

Gly Ala  Gln Val Leu Arg Ser  Arg Leu Glu Glu Val  Leu Gly Arg
    1070                1075                1080

Ser Leu  Glu Arg Leu Asn Arg  Leu Glu Thr Leu Ala  Ala Ile Gly
    1085                1090                1095

Gly Gly  Glu Leu Glu Ser Val  Arg Ile His His Lys  His Ala Tyr
    1100                1105                1110
```

<210> SEQ ID NO 13
<211> LENGTH: 1118
<212> TYPE: PRT

<213> ORGANISM: Mus Musculus

<400> SEQUENCE: 13

```
Met Lys Glu Ile Cys Arg Ile Cys Ala Arg Glu Leu Cys Gly Asn Gln
1               5                   10                  15

Arg Arg Trp Ile Phe His Thr Ala Ser Lys Leu Asn Leu Gln Val Leu
            20                  25                  30

Leu Ser His Val Leu Gly Lys Asp Val Ser Arg Asp Gly Lys Ala Glu
        35                  40                  45

Phe Ala Cys Ser Lys Cys Ala Phe Met Leu Asp Arg Ile Tyr Arg Phe
    50                  55                  60

Asp Thr Val Ile Ala Arg Ile Glu Ala Leu Ser Leu Glu Arg Leu Gln
65                  70                  75                  80

Lys Leu Leu Leu Glu Lys Asp Arg Leu Lys Phe Cys Ile Ala Ser Met
                85                  90                  95

Tyr Arg Lys Asn Asn Asp Asp Ser Gly Glu Glu Asn Lys Ala Gly Ser
            100                 105                 110

Gly Thr Val Asp Ile Ser Gly Leu Pro Asp Met Arg Tyr Ala Ala Leu
        115                 120                 125

Leu Gln Glu Asp Phe Ala Tyr Ser Gly Phe Glu Cys Trp Val Glu Asn
    130                 135                 140

Glu Asp Gln Ile Asn Asp Ser His Ser Cys His Ala Ser Glu Gly Pro
145                 150                 155                 160

Gly Asn Arg Pro Arg Arg Cys Arg Gly Cys Ala Ala Leu Arg Val Ala
                165                 170                 175

Asp Ser Asp Tyr Glu Ala Ile Cys Lys Val Pro Arg Lys Val Ala Arg
            180                 185                 190

Ser Ile Ser Tyr Ala Pro Ser Ser Arg Trp Ser Thr Ser Ile Cys Thr
        195                 200                 205

Glu Glu Pro Ala Leu Ser Glu Val Gly Pro Pro Asp Leu Ala Ser Thr
    210                 215                 220

Lys Val Pro Pro Asp Gly Glu Ser Met Glu Glu Gly Thr Pro Gly Ser
225                 230                 235                 240

Ser Val Glu Ser Leu Asp Ala Ser Val Gln Ala Ser Pro Pro Gln Gln
                245                 250                 255

Lys Asp Glu Glu Thr Glu Arg Ser Ala Lys Glu Leu Val Lys Cys Asp
            260                 265                 270

Tyr Cys Ser Asp Glu Gln Ala Pro Gln His Leu Cys Asn His Lys Leu
        275                 280                 285

Glu Leu Ala Leu Ser Met Ile Lys Gly Leu Asp Tyr Lys Pro Ile Gln
    290                 295                 300

Ser Pro Arg Gly Ser Lys Leu Pro Ile Pro Val Lys Ser Ile Leu Pro
305                 310                 315                 320

Gly Ala Lys Pro Gly His Ile Leu Thr Asn Gly Val Ser Ser Ser Phe
                325                 330                 335

Leu Asn Arg Pro Leu Lys Pro Leu Tyr Arg Thr Pro Val Ser Tyr Pro
            340                 345                 350

Trp Glu Ile Ser Asp Gly Gln Glu Leu Trp Asp Asp Leu Cys Asp Glu
        355                 360                 365

Tyr Leu Pro Ile Gly Phe Gln Pro Val Pro Lys Gly Leu Pro Thr Gln
    370                 375                 380

Gln Lys Pro Asp Leu His Glu Thr Pro Thr Thr Gln Pro Pro Val Ser
385                 390                 395                 400
```

```
Glu Ser His Leu Ala Glu Leu Gln Asp Lys Ile Gln Gln Thr Glu Ala
                405                 410                 415

Thr Asn Lys Ile Leu Gln Glu Lys Leu Asn Asp Leu Ser Cys Glu Leu
            420                 425                 430

Lys Ser Ala Gln Glu Ser Ser Gln Lys Gln Asp Thr Thr Ile Gln Ser
        435                 440                 445

Leu Lys Glu Met Leu Lys Ser Arg Glu Ser Glu Thr Glu Glu Leu Tyr
    450                 455                 460

Gln Val Ile Glu Gly Gln Asn Asp Thr Met Ala Lys Leu Arg Glu Met
465                 470                 475                 480

Leu His Gln Ser Gln Leu Gly Gln Leu His Ser Ser Glu Gly Ile Ala
                485                 490                 495

Pro Ala Gln Gln Gln Val Ala Leu Leu Asp Leu Gln Ser Ala Leu Phe
            500                 505                 510

Cys Ser Gln Leu Glu Ile Gln Arg Leu Gln Arg Leu Val Arg Gln Lys
        515                 520                 525

Glu Arg Gln Leu Ala Asp Gly Lys Arg Cys Val Gln Leu Val Glu Ala
    530                 535                 540

Ala Ala Gln Glu Arg Glu His Gln Lys Glu Ala Ala Trp Lys His Asn
545                 550                 555                 560

Gln Glu Leu Arg Lys Ala Leu Gln His Leu Gln Gly Glu Leu His Ser
                565                 570                 575

Lys Ser Gln Gln Leu His Val Leu Glu Ala Glu Lys Tyr Asn Glu Ile
            580                 585                 590

Arg Thr Gln Gly Gln Asn Ile Gln His Leu Ser His Ser Leu Ser His
        595                 600                 605

Lys Glu Gln Leu Ile Gln Glu Leu Gln Glu Leu Leu Gln Tyr Arg Asp
    610                 615                 620

Asn Ala Asp Lys Thr Leu Asp Thr Asn Glu Val Phe Leu Glu Lys Leu
625                 630                 635                 640

Arg Gln Arg Ile Gln Asp Arg Ala Val Ala Leu Glu Arg Val Ile Asp
                645                 650                 655

Glu Lys Phe Ser Ala Leu Glu Glu Lys Asp Lys Glu Leu Arg Gln Leu
            660                 665                 670

Arg Leu Ala Val Arg Asp Arg Asp His Asp Leu Glu Arg Leu Arg Cys
        675                 680                 685

Val Leu Ser Ala Asn Glu Ala Thr Met Gln Ser Met Glu Ser Leu Leu
    690                 695                 700

Arg Ala Arg Gly Leu Glu Val Glu Gln Leu Thr Ala Thr Cys Gln Asn
705                 710                 715                 720

Leu Gln Trp Leu Lys Glu Glu Leu Glu Thr Lys Phe Gly His Trp Gln
                725                 730                 735

Lys Glu Gln Glu Ser Ile Ile Gln Gln Leu Gln Thr Ser Leu His Asp
            740                 745                 750

Arg Asn Lys Glu Val Glu Asp Leu Ser Ala Thr Leu Leu Cys Lys Leu
        755                 760                 765

Gly Pro Gly Gln Ser Glu Val Ala Glu Glu Leu Cys Gln Arg Leu Gln
    770                 775                 780

Arg Lys Glu Arg Met Leu Gln Asp Leu Leu Ser Asp Arg Asn Lys Gln
785                 790                 795                 800

Ala Val Glu His Glu Met Glu Ile Gln Gly Leu Leu Gln Ser Met Gly
                805                 810                 815

Thr Arg Glu Gln Glu Arg Gln Ala Ala Ala Glu Lys Met Val Gln Ala
```

```
            820                 825                 830

Phe Met Glu Arg Asn Ser Glu Leu Gln Ala Leu Arg Gln Tyr Leu Gly
        835                 840                 845

Gly Lys Glu Leu Met Thr Ser Ser Gln Ala Phe Ile Ser Asn Gln Pro
    850                 855                 860

Ala Gly Val Thr Ser Ile Gly Pro His His Gly Glu Gln Thr Asp Gln
865                 870                 875                 880

Gly Ser Met Gln Met Pro Ser Arg Asp Asp Ser Thr Ser Leu Thr Ala
                885                 890                 895

Arg Glu Glu Ala Ser Ile Pro Arg Ser Thr Leu Gly Asp Ser Asp Thr
            900                 905                 910

Val Ala Gly Leu Glu Lys Glu Leu Ser Asn Ala Lys Glu Glu Leu Glu
        915                 920                 925

Leu Met Ala Lys Lys Glu Arg Glu Ser Gln Met Glu Leu Ser Ala Leu
    930                 935                 940

Gln Ser Met Met Ala Val Gln Glu Glu Glu Leu Gln Val Gln Ala Ala
945                 950                 955                 960

Asp Leu Glu Ser Leu Thr Arg Asn Val Gln Ile Lys Glu Asp Leu Ile
                965                 970                 975

Lys Asp Leu Gln Met Gln Leu Val Asp Pro Glu Asp Ile Pro Ala Met
            980                 985                 990

Glu Arg Leu Thr Gln Glu Val Leu  Leu Leu Arg Glu Lys  Val Ala Ser
        995                 1000                1005

Val Glu  Pro Gln Gly Gln Glu  Val Ser Gly Asn Lys  Arg Gln Gln
    1010                1015                1020

Leu Leu  Leu Met Leu Glu Gly  Leu Val Asp Glu Arg  Ser Arg Leu
    1025                1030                1035

Asn Glu  Ala Leu Gln Ala Glu  Arg Gln Leu Tyr Ser  Ser Leu Val
    1040                1045                1050

Lys Phe  His Ala Gln Pro Glu  Asn Ser Glu Arg Asp  Arg Thr Leu
    1055                1060                1065

Gln Val  Glu Leu Glu Gly Ala  Gln Val Leu Arg Thr  Arg Leu Glu
    1070                1075                1080

Glu Val  Leu Gly Arg Ser Leu  Glu Arg Leu Ser Arg  Leu Glu Ser
    1085                1090                1095

Leu Ala  Ala Ile Gly Gly Gly  Glu Leu Glu Ser Val  Gln Ala Arg
    1100                1105                1110

His Lys  His Ala Phe
    1115


<210> SEQ ID NO 14
<211> LENGTH: 1394
<212> TYPE: PRT
<213> ORGANISM: Gallus gallus

<400> SEQUENCE: 14

Met Asn Ile Arg Ser Gln Leu Gln Phe Cys Ile Ala Ser Met Tyr Arg
1               5                   10                  15

Arg Asn Asn Glu Glu Pro Gly Thr Asp Glu Arg Ala Gly Asp Gly Thr
            20                  25                  30

Val Asp Leu Ser Asn Leu Pro Asp Ala Arg Tyr Ala Ala Leu Leu Gln
        35                  40                  45

Glu Asp Phe Ala Tyr Ser Gly Tyr Glu Tyr Trp Thr Asp Gln Asp Glu
    50                  55                  60
```

```
His Ser Leu Glu Pro His Ser Cys His Ala Ser Glu Gly Ala Ala Ser
65                  70                  75                  80

Arg Pro Arg Arg Cys Arg Gly Cys Ala Ala Leu Arg Val Ala Asp Ala
                85                  90                  95

Asp Tyr Glu Ala Ile Cys Lys Val Pro Arg Lys Val Ala Arg Ser Ile
            100                 105                 110

Ser Cys Gly Leu Ser Ser Arg Trp Ser Val Ser Met Gly Asn Glu Glu
        115                 120                 125

Ser Ser Val Cys Asp Pro Ala Glu Pro Ala Gly Ala Arg Gly Pro Val
    130                 135                 140

Asp Gly Glu Ser Met Glu Glu Gly Thr Pro Ala Ser Ser Val Glu Ser
145                 150                 155                 160

Leu Asp Thr Thr Val Glu Ala Ser Ala Pro Gln Gln Lys Asp Glu Asp
                165                 170                 175

Val Asp Lys Gly Val Lys Gly Asn Gly Lys Cys Asp Asp Phe Ala Glu
            180                 185                 190

Asp Arg Met Thr Pro Ser Ser Ser Leu Ser Gly Asn Arg Leu Glu Leu
        195                 200                 205

Ala Leu Ser Leu Ile Lys Gly Leu Asp Tyr Lys Pro Ile Gln Ser Pro
    210                 215                 220

Arg Gly Ser Arg Leu Pro Ile Pro Val Lys Ser Ser Leu Pro Pro Pro
225                 230                 235                 240

Lys Leu Ser Arg Asp Leu Ala Asp Gly Ser Ala Ser Ala Gly Leu Ala
                245                 250                 255

Tyr Ala Gly Ser Gly Phe Leu Asn Ala Asp Arg Lys Ser Phe Ser Arg
            260                 265                 270

Ala Pro Leu Gly Leu Pro Leu Glu Ile Pro Glu Leu Gln Glu Leu Trp
        275                 280                 285

Asp Asp Phe Cys Glu Asp Tyr Met Pro Leu Arg Val Gln Pro Arg Val
    290                 295                 300

Ala Glu Pro Arg Ala Lys Asn Ser Gln Leu Asn Glu His Gln Lys Pro
305                 310                 315                 320

Ala Pro Gly Asp Ser Ala Ser Arg Glu Cys Thr Ala Asp Leu Cys Ala
                325                 330                 335

Thr Glu Pro Gln Gly Lys Ile Gln Gln Phe Glu Asp Thr Asn Gln Leu
            340                 345                 350

Leu Gln Glu Lys Leu Asn Glu Leu Asn Phe Glu Leu Lys Ser Ala Arg
        355                 360                 365

Glu Thr Ser Gln Arg Gln Asp Leu Thr Ile Gln Ser Leu Asn Glu Ala
    370                 375                 380

Leu Lys Ser Lys Glu Ser Glu Thr Glu Glu Leu Tyr His Val Ile Glu
385                 390                 395                 400

Gly Gln Asn Glu Thr Met Ala Lys Leu Gln Asp Met Leu His Arg Ser
                405                 410                 415

Gln Leu Gly Gln Leu Gln Met Ser Glu Ser Ala Pro Ser Ser Gln Glu
            420                 425                 430

Gln Gln Val Ala Leu Leu Asp Leu Gln Asn Thr Leu Phe Ser Thr Gln
        435                 440                 445

Leu Glu Val Gln Lys Leu Lys Arg Ala Gln Arg Gln Lys Glu His Gln
    450                 455                 460

Leu Val Glu Ala Lys Arg Ala Ala Gln Leu Leu Glu Thr Thr Val His
465                 470                 475                 480

Glu Glu Glu Gln Gln Lys Glu Ala Thr Trp Lys His Asn Gln Glu Leu
```

```
                485                 490                 495

Arg Ala Val Val Gln Gln Leu Gln Val Glu Leu Gln Asp Lys Ala Gln
            500                 505                 510

Gln Ile Gln Ala Met Glu Trp Glu Lys Cys Arg Glu Leu Gln Ala Gln
        515                 520                 525

Glu Gln Arg Val Gln Cys Leu Ser Gln His Leu Ala Arg Lys Glu Gln
    530                 535                 540

Leu Leu Gln Glu Ser Arg Glu Leu Leu Gln Cys Gln Gln Ser Leu Gly
545                 550                 555                 560

Arg Ser Ser Ala Ala Met Asp Ala Met Leu Glu Lys Leu Gln Gln Arg
                565                 570                 575

Val Ser Asp Arg Asp Ala Ala Leu Glu Arg Ala Val Asp Glu Lys Phe
            580                 585                 590

Cys Ala Leu Glu Glu Lys Glu Gln Glu Leu Gln Gln Leu Arg Leu Ser
        595                 600                 605

Ile Lys Glu Arg Gly Gly Asp Leu Glu Arg Leu Arg Asn Val Leu Ser
    610                 615                 620

Ser Asn Glu Ala Thr Ile His Ser Leu Glu Ser Leu Leu Lys Ala Lys
625                 630                 635                 640

Thr Leu Glu Leu Glu Gln Met Ser Ala Thr Cys Glu Asn Leu Arg Trp
                645                 650                 655

Leu Lys Glu Glu Ile Glu Ala Lys Ser Cys Ser Arg Gln Lys Glu Gln
            660                 665                 670

Glu Gly Ile Ile Gln Gln Leu Gln Thr Cys Leu His Asp Arg Asn Lys
        675                 680                 685

Glu Val Glu Glu Leu Thr Ala Thr Leu Leu Cys Lys Leu Gly Pro Gly
    690                 695                 700

Gln Ser Glu Val Ala Glu Glu Leu Cys Leu Arg Leu Gln Arg Lys Glu
705                 710                 715                 720

Lys Met Leu Gln Glu Leu Leu Ser Asp Arg Asn Arg Gln Ala Met Glu
                725                 730                 735

His Asp Ala Glu Ile Arg Glu Leu Leu Gln Ala Met Ser Thr Lys Glu
            740                 745                 750

Gln Trp Ser Lys Ala Thr Thr Glu Lys Met Val His Ala Leu Ala Glu
        755                 760                 765

Arg Asn Cys Glu Leu Gln Leu Leu Arg Gln His Val Leu Arg Lys Lys
    770                 775                 780

Pro Val Gly Ile Gln Ala Thr Gly Thr Ser Leu Leu Lys Gln Asp Lys
785                 790                 795                 800

Gln Gln Pro Val Gln Glu Ile Leu Gln Arg Ala Cys Gly Ala Ala Ala
                805                 810                 815

Leu Ala Gly Pro Gln Gln Glu Asp Asn Ser Cys Leu Thr Glu Gly Glu
            820                 825                 830

Gly Phe Cys Leu Ile Ser Gln Ser Glu Gly Ala Asp Asp Thr Trp Asp
        835                 840                 845

Gly Phe Pro Lys Asp Leu Gln Ser Ala Thr Trp Pro Gly Lys Tyr Asn
    850                 855                 860

Ser Leu Ile Gln Ala Gln Ala Arg Glu Leu Ser His Leu Arg Gln Thr
865                 870                 875                 880

Leu Arg Glu Ser Arg Gly Val Ser Arg Ser Leu Ala Gln His Leu Arg
                885                 890                 895

Asp Ala Leu Arg Ser Phe Glu Glu Leu Leu Arg Gly Thr Asp Ile Asp
            900                 905                 910
```

```
Tyr Tyr Leu Gly Gln Gly Phe Arg Glu Gln Leu Ala Gln Gly Arg His
        915                 920                 925

Leu Ala Glu Arg Leu Ser Asp Lys Leu Gly Thr Trp Asp Arg Gln Asp
    930                 935                 940

Gly Glu Asp Lys Ser Ser His Glu Leu Leu Ala Leu Arg Leu Ser Arg
945                 950                 955                 960

Glu Leu Gln Glu Lys Glu Lys Val Ile Glu Ser Leu Glu Ala Lys Leu
                965                 970                 975

Gln Glu Arg Cys Glu Ser Pro Gly Ser Ser Arg Pro Pro Ser Glu Ser
            980                 985                 990

Ser Arg Ser Ala Thr Ser Thr Ser  Phe Val Ser Asp Val  Leu Glu Pro
        995                 1000                1005

Cys Ser  Asp Gly Glu Ala Ala  Ser Glu Cys Ser Gln  Cys Pro Glu
    1010                1015                1020

Glu Pro  Thr Arg Leu Pro Gly  Leu His Phe Asp Thr  Leu Ser Lys
    1025                1030                1035

Pro Asn  Ser Val Pro Leu Pro  Ala Leu Ala Pro Thr  His Ser Phe
    1040                1045                1050

Leu Pro  Thr Gly Leu Pro Val  Pro Leu Asp Cys Cys  Gly Thr Arg
    1055                1060                1065

Ala Cys  Ser Leu Ala Glu Ala  Gln Gln Glu Leu Gln  Val Leu Gln
    1070                1075                1080

Arg Gln  Leu Gly Glu Ser Val  Thr Leu Pro Thr Ala  Lys Pro Thr
    1085                1090                1095

Ala Ser  Leu Gly Pro Phe Gly  Glu Gly Ser Lys Pro  Ala Ala Ser
    1100                1105                1110

Leu Cys  Gln His Gly Ala Leu  Gln Thr Leu Ser Lys  Pro Pro Ala
    1115                1120                1125

Leu Trp  Asp Val Pro Ala Ala  Gly Arg Leu Tyr Gly  Thr Leu Pro
    1130                1135                1140

Ser Gly  Cys Pro Ser Ser Gln  Lys Leu Thr Gly Ala  Asp Leu Leu
    1145                1150                1155

Glu Glu  His Leu Val Glu Ile  Arg Ser Leu Arg Gln  Arg Leu Glu
    1160                1165                1170

Glu Ser  Ile Cys Thr Asn Asp  Arg Leu Arg Glu Gln  Leu Glu Arg
    1175                1180                1185

Arg Leu  Ala Ser Thr Ala Lys  Ala Leu Arg Met Glu  Leu His Val
    1190                1195                1200

Tyr Glu  Ser Pro Leu Leu Thr  Pro Thr Glu Pro Arg  Ala Glu Pro
    1205                1210                1215

Cys Arg  Ala Ser Pro Pro Glu  Lys Lys Ser Lys Gly  Pro Ala Gly
    1220                1225                1230

Ala His  Val Val Gly His Leu  Asp Thr Tyr Arg Ser  Leu Glu Gln
    1235                1240                1245

Arg Ile  Leu Glu Gly Lys Ala  Leu Ala His Glu Leu  Thr Cys Leu
    1250                1255                1260

Thr Arg  Pro Ala Leu Gly Leu  Ser Ser Thr Gly Lys  Glu Val Pro
    1265                1270                1275

Gly Cys  Ile Gly Ala Gly His  Leu Trp Gly Ser Ala  Ser Thr Leu
    1280                1285                1290

His Arg  Val Leu Glu Glu Cys  Ala Ser Leu Leu Thr  Thr Phe Trp
    1295                1300                1305
```

```
Ser Thr  Val Leu Pro Val Gly  Pro Ala Gln His Gln  Gly Lys Glu
    1310                 1315                 1320

Gln Ala  Leu Gln Ser Glu Ile  Thr Ala Leu Arg Ala  Gln Leu Ser
    1325                 1330                 1335

Lys Arg  Glu Asp Ala Leu His  Asn Thr Ala Lys Gln  Leu His Ser
    1340                 1345                 1350

Met Ala  Gln Leu Lys Asp Ser  Met Glu Gln Phe Ile  Val Ser Gln
    1355                 1360                 1365

Leu Thr  Arg Thr His Asn Val  Leu His Lys Ala Arg  Thr Asn Leu
    1370                 1375                 1380

Glu Val  Lys Ala Gln Gln Ala  Leu Pro Val Ala
    1385                 1390


<210> SEQ ID NO 15
<211> LENGTH: 1106
<212> TYPE: PRT
<213> ORGANISM: Xenopus tropicalis

<400> SEQUENCE: 15

Met Lys Glu Ser Cys Arg Ile Cys Gly Arg Glu Leu Cys Gly Asn Gln
1               5                   10                  15

Arg Arg Trp Ile Phe His Thr Ala Ser Lys Leu Asn Leu Gln Val Leu
            20                  25                  30

Leu Cys His Val Leu Gly Arg Glu Val Pro Arg Asp Gly Arg Ala Glu
        35                  40                  45

Phe Ala Cys Ser Lys Cys Ala Phe Met Leu Glu Arg Met Cys Arg Phe
    50                  55                  60

Asp Thr Val Ile Ala Arg Ile Glu Ala Leu Ser Ile Glu Arg Leu His
65                  70                  75                  80

Lys Leu Ile Ser Glu Lys Glu Arg Leu Lys His Cys Leu Ala Gly Leu
                85                  90                  95

Tyr Arg Lys His Asn Ser Glu Glu Asp Gly Pro Asp Thr Gly Pro Asp
            100                 105                 110

Thr Gly Pro Asp Ser Arg Pro Ala Ala Glu Gly Gly Thr Val Asp Ile
        115                 120                 125

Ser Glu Leu Pro Asp Val Arg Tyr Ser Ala Leu Leu Gln Glu Asp Phe
    130                 135                 140

Ala Tyr Ser Gly Tyr Glu Tyr Trp Ala Glu Leu Asp Gln Gln Ser Gln
145                 150                 155                 160

Glu Pro Gln His Cys Gln His Thr Asp Thr Gly Gly Val Arg Pro Arg
                165                 170                 175

Arg Cys Arg Gly Cys Ser Gly Leu Arg Val Ala Asp Ser Asp Tyr Glu
            180                 185                 190

Ala Val Cys Lys Val Pro Arg Lys Val Ala Arg Ser Pro Ser Cys Gly
        195                 200                 205

Pro Ser Thr Lys Gly Ser Ala Ser Phe Cys Thr Glu Glu Thr Met Val
    210                 215                 220

Thr Gln Pro Pro Pro Gln Pro Leu Pro Glu Ala Lys Ala Pro Pro Glu
225                 230                 235                 240

Gly Asp Gly Leu Arg Leu Ser Ser Gly Ser Ser Ala Glu Ser Leu Ala
                245                 250                 255

Thr His Met Asp Ala Ala Ala Thr Pro Ser His Lys Glu Glu Glu Pro
            260                 265                 270

Cys Lys Pro Pro Gly Asp Asp Ala Lys Cys Asp Tyr Cys Ser Ile Asn
        275                 280                 285
```

```
His Val Ala His Ser Pro Val Asn Gly Ser Arg Ser Glu Phe Ala Phe
    290                 295                 300

Leu Leu Ala Lys Val Phe Asn Tyr Lys Pro Val Gln Ile Pro Arg Gly
305                 310                 315                 320

Cys Arg Ile Pro Val Lys Ser Arg Leu His Asp Phe Lys Pro Asn Ile
                325                 330                 335

Met Val Ala Ser Gly Leu Ser Ala Thr Pro Ser Pro Gly Leu Gly Phe
            340                 345                 350

Leu Gly Ile Ile Ala Glu Ser Pro Pro Ser Asn Ala Gln Asp Phe Val
        355                 360                 365

Pro Glu Leu Tyr Asp Val Gln Asp Leu Trp Gln Asp Val Tyr Glu Glu
    370                 375                 380

Tyr Ile Pro Leu His Thr Gln Asn Leu Leu Glu Lys Gln His Gln Asn
385                 390                 395                 400

Val Ser Gln Tyr Glu Ala Leu Ser Ala Gln His Val Ser Asp Leu Gln
                405                 410                 415

Thr Leu Gln Gly Arg Leu Gln Glu Thr Glu Ala Ser Asn Lys Met Leu
            420                 425                 430

Gln Glu Ser Leu His Gln Val Thr Ala Glu Leu Asn Ser Ala Arg Glu
        435                 440                 445

Leu Ser Cys Asn Gln Glu Arg Ile Ile Gln Ser Leu Arg Glu Thr Leu
    450                 455                 460

Gln Ser Arg Asp Ser Glu Val Ala Asp Leu Tyr His Ile Val Glu Gly
465                 470                 475                 480

His Asn Asp Thr Ile Val Lys Leu Gln Asn Met Leu Gln Lys Ser Gln
                485                 490                 495

Thr Glu Gln Leu Gln Ala Ser Gln Val Thr Pro Ser Gln Gln Gln Leu
            500                 505                 510

Gln Leu Leu Asp Leu Gln Asn Thr Leu Phe Cys Thr Gln Arg Glu Leu
        515                 520                 525

Gln Lys Gln Gln Arg Thr Leu Arg Gln Lys Glu Arg Gln Leu Thr Asp
    530                 535                 540

Leu Glu Gln Ser Gln Arg Leu Leu Glu Ala Asp Leu Leu Glu Gly Gln
545                 550                 555                 560

Gln Gln Lys Glu Thr Thr Trp Lys His Asn Gln Glu Leu His Gly Val
                565                 570                 575

Leu His Lys Leu Gln Thr Glu Leu Gln Glu Lys Ser Gln Leu Leu Gln
            580                 585                 590

Asn Ser Glu Glu Glu Lys Cys Thr Lys Leu Arg Ala Gln Glu Asn Cys
        595                 600                 605

Ile Gln Lys Leu Gln Gln Thr Leu Ala Gln Lys Glu Gln Leu Gln Gln
    610                 615                 620

Glu Tyr Met Asp Leu Leu Lys Tyr Gln Gln Ser Leu Gly Lys His Pro
625                 630                 635                 640

Gly Gly Ser Glu His Met Leu Asp Lys Leu Arg Gln Arg Ile Lys Asp
                645                 650                 655

Arg Asp Ala Ala Leu Glu Gln Ala Val Asp Asp Lys Phe Cys Ala Leu
            660                 665                 670

Glu Glu Lys Glu Lys Glu Ile Gln Gln Leu Lys Met Ile Ile Arg Glu
        675                 680                 685

Lys Gln Arg Asp Leu Glu Arg Leu Gln Ser Val Leu Ser Gly Asn Glu
    690                 695                 700
```

```
Glu Thr Ile Asn Ser Leu Asp Asn Leu Met Lys Ser Lys Asp Leu Glu
705                 710                 715                 720

Leu Glu His Ile Ser Ala Ala Tyr Lys Asn Leu Glu Trp Leu Lys Gln
                725                 730                 735

Glu Met Glu Glu Lys Asn Gln Arg Ser Leu Lys Glu Arg Asp Ser Ile
            740                 745                 750

Ile Gln Gln Leu Gln Gln Ala Leu Gln Asp Arg Ser Lys Glu Ile Gln
        755                 760                 765

Asp Met Met Ala Thr Phe Leu Gln Lys Ser Glu Met Gly Ser Phe Asp
    770                 775                 780

Leu Ile Gln Glu Leu Gln Ala Cys Leu Glu Cys Lys Glu Lys Met Leu
785                 790                 795                 800

Gln Glu Ala Leu His Asn Arg Ser Gln Gln Ala Asp Glu His Met Arg
                805                 810                 815

Glu Leu Glu Glu Leu Leu Thr Ser Met Ala Ser Glu Lys Met Gly Gln
            820                 825                 830

Gly Phe Val Cys Lys Ser Cys Ala Leu Lys Glu Lys Gln Asn Ser Glu
        835                 840                 845

Met Asp Gln Ser Pro Ala Cys Gln Lys Thr Val Lys Gln Leu Ala Lys
    850                 855                 860

Ala Lys Pro Leu Ser Asp His Pro Ile Ser Val Cys Val Thr Ser Leu
865                 870                 875                 880

Ser Ala Asp Leu Lys Asp Pro Val Ala Gln Ser Asn Gln Thr Glu Ala
                885                 890                 895

Leu Glu Ser Glu Leu Ala Lys Ala Lys Asp Asp Leu Gln Leu Val Leu
            900                 905                 910

Arg Lys Glu Arg Glu Asn Gln Ile Glu Val Ser Ala Leu Gln Ser Val
        915                 920                 925

Ile Arg Glu Gln Ser Glu Gln Leu Gln Glu Gln Ala Ala Asp Met Asp
    930                 935                 940

Ala Leu Asn Arg Ser Ile Gln Ile Lys Glu Asp Leu Ile Lys Asp Leu
945                 950                 955                 960

Gln Met Gln Leu Val Asp Pro Glu Glu Val Pro Thr Val Glu His Leu
                965                 970                 975

Thr Gln Glu Val Leu Ser Leu Lys Glu Lys Leu Ala Ile Ser Gly Val
            980                 985                 990

Pro Glu Pro Glu His Gly Ile Asp  His Tyr Gln Lys Leu  Ser Lys Leu
        995                 1000                1005

Leu Glu  Glu Leu Val Ala Asp  Arg Ser Arg Leu Asn  Asp Ala Leu
    1010                1015                1020

His Ala  Glu Lys Gln Leu Tyr  Ser Ser Leu Val Gln  Phe His Ser
    1025                1030                1035

Asp Pro  Asp Ser Ile Lys Arg  Thr Ser Ala Leu Gln  Glu Glu Leu
    1040                1045                1050

Leu Thr  Ala Gln Thr Leu Thr  Cys Gln Leu Glu Asp  Thr Leu Glu
    1055                1060                1065

Met Ala  Thr Glu Arg Leu Arg  Gln Leu Asp Ser Glu  Arg Gly Leu
    1070                1075                1080

Thr Ala  Ile Thr Phe Gly Gly  Gly Glu Trp Gly Ser  Leu Ser Val
    1085                1090                1095

Pro His  Met His Thr His Ala  Phe
    1100                1105
```

```
<210> SEQ ID NO 16
<211> LENGTH: 2431
<212> TYPE: PRT
<213> ORGANISM: Danio rerio

<400> SEQUENCE: 16

Met Phe Asn Gly Tyr Arg Thr Ile Ser Gln His Leu Asn Asp Leu Lys
1               5                   10                  15

Lys Glu Asn Phe Ser Leu Lys Leu Arg Ile Tyr Phe Leu Glu Glu Arg
            20                  25                  30

Phe Gln Gln Thr Phe Glu Asp Ser Ser Ser Glu Asp Val His Arg Arg
        35                  40                  45

Asn Ile Glu Leu Lys Val Glu Val Glu Ser Leu Lys Gln Asp Leu Lys
    50                  55                  60

Glu Arg Gln Glu Gln Phe Asp Lys Ala Leu Thr Thr Ala Glu Ser Leu
65                  70                  75                  80

Ser Ser Gln Asn Glu Val Glu Val Gln Arg Arg Cys Glu Glu Arg Gln
                85                  90                  95

Gln Glu Thr Gly His Ile Gln Glu Ile Leu Gln Thr Lys Ile Gln Leu
            100                 105                 110

Leu Gln Glu Glu Ala Arg Leu Ala Arg Asp Glu Ala Glu Lys Met Ala
        115                 120                 125

Ser Met Ala Glu Ser Glu Ser Gln Arg Cys Leu Asp Leu Glu Asn Arg
    130                 135                 140

Met Met Thr Val Met Gln Asp Gly Asn Glu Ser Leu Pro Val Met Ala
145                 150                 155                 160

Gln Tyr Glu Glu Met Ala Lys Lys Asp Arg Leu Ile Glu Glu Leu Asn
                165                 170                 175

Glu Thr Val Cys Arg Lys Glu Arg Glu Ala Ala Asp Leu Ser Ser Gln
            180                 185                 190

Arg Asp Val Leu Thr Val Lys Leu Thr Gln Leu Glu Glu Gln Val Gln
        195                 200                 205

Ser Leu Gln Gln Lys Glu Lys His Thr Gln Met Leu Asp Ser Lys Ser
    210                 215                 220

Lys Asp Val Cys Arg Ile Cys Ala Arg Glu Leu Tyr Gly Asn Gln Arg
225                 230                 235                 240

Arg Trp Ile Phe His Pro Thr Ala Lys Leu Ser Leu Gln Val Leu Leu
                245                 250                 255

Ser Tyr Ala Leu Gly Arg Glu Met Thr Arg Asp Gly Arg Gly Glu Phe
            260                 265                 270

Ala Cys Ser Lys Cys Ala Phe Met Leu Asp Arg Met Tyr Arg Phe Asp
        275                 280                 285

Thr Val Ile Ala Arg Val Glu Ala Leu Ser Leu Glu Arg Met Gln Lys
    290                 295                 300

Leu Leu Leu Glu Lys Asp Arg Leu Arg Gln Cys Ile Ser Gly Leu Tyr
305                 310                 315                 320

Arg Lys Asn Asn Thr Asp Glu Leu Gly Val Asp Gly Gly Ala Thr Asp
                325                 330                 335

Ala Thr Val Val Asp Phe Ala Arg Leu Ala Glu Ala Glu Tyr Ser Ala
            340                 345                 350

Leu Leu Gln Glu Asp Leu Thr Tyr Ser Val Tyr Glu Ser Trp Ala Glu
        355                 360                 365

Gln Cys Pro Gln Glu Gln Ile Gln Asp His Gln Cys Pro Leu His His
    370                 375                 380
```

```
Ala Asp Ala Ala Ser Gly Pro Arg Pro Arg Lys Cys Lys Gly Cys Ala
385                 390                 395                 400

Ala Leu Arg Val Thr Asp Ser Asp Tyr Glu Ala Val Cys Lys Val Pro
                405                 410                 415

Arg Lys Val Gly Arg Ser Thr Ser Cys Gly Pro Ser Thr Arg Tyr Ser
            420                 425                 430

Gly Ser Val Gln Asp Asn Thr Glu Glu Thr Val Pro Ser Ala Pro Pro
        435                 440                 445

Pro Glu Pro Ile Glu Asn Asn Gln Ser Cys Glu Leu Lys Pro Val Gly
    450                 455                 460

Val Ser Pro Ala Ser Ser Val Glu Ser Leu Asp Thr Ala Val Asp Val
465                 470                 475                 480

Thr Gln Glu Ser Tyr Leu Lys Leu Pro Leu Leu Glu Ser Glu Glu Glu
                485                 490                 495

Gln Ser Val Val Arg Arg Pro Glu Ser Lys Pro Gly Ser Val Cys Gly
            500                 505                 510

Leu Asp Val Ala Leu Ser Leu Leu Lys Ser Cys Glu Tyr His Pro Leu
        515                 520                 525

Gln Ser Gln Arg Gly Ser Arg Ile Pro Val Leu Leu Lys Thr Asn Thr
    530                 535                 540

Thr Pro Met Glu Ser Pro Tyr Pro Leu Leu Gln Val Pro His Ile Glu
545                 550                 555                 560

Met Glu Cys Pro Leu Phe Pro Gln Leu Pro Asp Val Pro Ser Ser Ile
                565                 570                 575

Gln Gln Glu Leu Gln Leu Glu Leu Ala Glu Met Glu Asp Gln Trp Leu
            580                 585                 590

Asp Asp Tyr Val Gln Cys Lys Pro Ser Gly Leu Pro Lys Arg Leu Ile
        595                 600                 605

Glu Glu Gln Gln Cys His Leu Ala Glu Tyr Glu Asn Ala Ala Gly Gln
    610                 615                 620

Cys Val Asn Glu Leu Gln Lys Ala Gln Gln Gln Val Gln Ser Leu Gln
625                 630                 635                 640

Thr Lys Ile Arg Asp Ser Glu Ala Ser Asn Lys Lys Leu Gln Gln Lys
                645                 650                 655

Leu Arg Asp Met Glu Asn Glu Leu Arg Ser Val Arg Glu Ala Ala Cys
            660                 665                 670

Gly Gln Glu Thr Thr Ile Gln Thr Leu Gly Asp Ser Leu Ser Thr Lys
        675                 680                 685

Asp Tyr Glu Arg Val Ile Glu Glu Gln Lys Glu Leu Leu Cys Ser Leu
    690                 695                 700

Lys Gln Gln Asn Asn His Tyr Gln Leu Gln Gln Gln Gln Val Ser Gly
705                 710                 715                 720

Val Thr Pro Ser His Leu Gln Ala Asp Leu Leu Asp Leu Gln Gly Ser
                725                 730                 735

Leu Phe Ser Ala Gln Leu Glu Leu Gln Gly Leu Gln Arg Thr Gln Gln
            740                 745                 750

Gln Ser Gln Arg Arg Glu Asp Asp Leu Thr Arg Ala Asn Gln Arg Leu
        755                 760                 765

Gln Thr Asp Leu Gln Gly Ala Val Gln Arg His Arg Glu Ala Glu Lys
    770                 775                 780

His Asn Gln Asp Leu Leu Thr Ala Leu Glu Ser Ala Arg Ala Lys Leu
785                 790                 795                 800

Leu Gln Thr Glu Glu Lys Trp Arg Asp Glu Gly Arg Gln Arg Glu Asn
```

```
                805                 810                 815

Glu Val Glu Glu Arg Glu Lys Thr Ile Arg Glu Leu Lys Thr Ser Leu
            820                 825                 830

Glu His Lys Glu Arg Leu Val Gln Asp Tyr Ser Glu Leu Val Asp Gly
        835                 840                 845

Gln Lys Glu Pro Ala Gly Asn Arg Asp Asn Leu Ile Gln Lys Leu Lys
    850                 855                 860

Gln Arg Ile Gln Glu Arg Asp Arg Ala Leu Glu Arg Ala Val Asp Glu
865                 870                 875                 880

Lys Phe Thr Cys Met Glu Gln Lys Glu Asp Glu Met Arg Lys Leu Gln
                885                 890                 895

Leu Leu Leu Arg Glu Lys Glu Arg Asp Leu Glu Lys Leu Arg Cys Val
            900                 905                 910

Leu Ser Asn Asn Glu Glu Thr Ile Met Ser Leu Glu Met Leu Leu Arg
        915                 920                 925

Gly Lys Gly Leu Glu Leu Glu Gln Val Cys Glu Ala Trp Arg Ser Ala
    930                 935                 940

Gln Gly Val His Ser Glu Arg Glu Glu Ser Tyr Met Arg Ser Leu Arg
945                 950                 955                 960

Glu Arg Asp Ala Leu Ile Ser Gln Leu Gln Thr Ser Leu His Thr Arg
                965                 970                 975

Thr Lys Glu Ala Glu Glu Met Thr Ala Val Leu Leu Ser Lys Val Ser
            980                 985                 990

Val Gly Ala Gly Glu Val Ala Glu  Glu Leu Lys Ser Arg  Leu Gln Leu
        995                 1000                1005

Lys Glu  Arg Leu Phe Gln Glu  Leu Leu Ser Asp Arg  Ser Arg Gln
    1010                1015                1020

Thr Gln  Glu His His Ser Gln  Val Gln Asp Leu Leu  Asn Thr Ile
    1025                1030                1035

Ser Ser  Arg Glu His Tyr Ile  Lys Asp Ser Ala Gly  Arg Val Gly
    1040                1045                1050

Gln Val  Met Ala Glu Gln Thr  Ala Arg Leu Gln Glu  Leu Arg Lys
    1055                1060                1065

Gln Leu  Gly Ser Ala Asn Pro  Glu Leu Thr Gln Glu  Asp Thr Gln
    1070                1075                1080

Ala Leu  Met Asp Glu Leu Gln  Met Thr Leu Arg Arg  Glu Arg Glu
    1085                1090                1095

Ala Gln  Thr Gln Leu Ser Ile  Leu Arg Ala Thr Leu  Ala Ser Tyr
    1100                1105                1110

Gln Asp  Gln Leu Gln Thr Gln  Thr Ser Asp Leu Asp  Ala Leu Ser
    1115                1120                1125

Arg Thr  Ala Ser Val Lys Glu  Glu Ile Ile Lys Asp  Leu Gln Met
    1130                1135                1140

Gln Leu  Val Glu Pro Ser Asp  Leu Pro Leu Val Glu  Arg Leu Thr
    1145                1150                1155

Gln Glu  Leu Gln Leu Leu Arg  Glu Lys Val Glu Ser  Gln Glu Ala
    1160                1165                1170

Ser Cys  Asn Asn His Lys Ala  Leu Leu Asp Pro Leu  Val Ser Met
    1175                1180                1185

Glu Thr  Gly Gln Ala Val Gln  Pro His Ala Asp Phe  Gly Gly Phe
    1190                1195                1200

Thr Ser  Asp Asp Gly Glu Glu  Glu Glu Asp Glu Glu  Asp Cys Asn
    1205                1210                1215
```

```
Ser Glu  Phe Ala Gly Ser Gly  Glu Asp Glu Lys Arg  Ser Lys Arg
    1220                 1225                 1230

Thr Ala  Gln Ser Leu Val Ser  Leu Gln Ser Cys Asp  Gln His Gln
    1235                 1240                 1245

Gly Leu  Arg Gly Cys Gln Asp  Ala Val Ala Glu Gly  Pro Gly Leu
    1250                 1255                 1260

Ala Glu  Val Lys Gln Leu Val  Glu Gln Lys Arg Ala  Val Glu Arg
    1265                 1270                 1275

Glu Leu  Met Glu Leu Lys Ser  Gln Leu Glu Lys Ala  Gly Phe Ser
    1280                 1285                 1290

Ser Leu  Ser Gln Met Arg Lys  Ala Phe Phe Thr Leu  Arg Ser Gln
    1295                 1300                 1305

Asn Glu  Glu Leu Lys Gly Leu  Met Asn Leu Gln Asn  Val Gly Gln
    1310                 1315                 1320

Lys Ser  Thr Ser Cys Gly Gln  Leu Val Asp Thr Val  Gly Ala Lys
    1325                 1330                 1335

Gly Lys  Glu Arg Glu Ser Ala  Arg Glu Gln Thr Val  Gln Leu Lys
    1340                 1345                 1350

Ser Asp  Leu Ala Gln Val Gln  Gln Glu Ser Arg Glu  Leu Gln Glu
    1355                 1360                 1365

Arg Leu  Met Val Ser Glu Ala  Thr Val Gln Ala Gln  Ala Glu Gln
    1370                 1375                 1380

Leu Lys  Asp Tyr Arg Glu Leu  Leu Thr Glu Thr Ser  Val Gln Gln
    1385                 1390                 1395

Asp Ser  Lys Gln Val Gln Val  Asp Ile Gln Asp Leu  Gly Tyr Glu
    1400                 1405                 1410

Thr Cys  Gly Arg Ser Glu Asn  Glu Ala Glu Arg Glu  Asp Thr Ser
    1415                 1420                 1425

Ser Pro  Glu Phe Asp Asp Leu  Glu Leu Cys Thr Ser  Leu Ser Tyr
    1430                 1435                 1440

Arg Asp  Ala Gly Ser Gln Trp  Trp Ala Gly Pro Ala  Thr His Asn
    1445                 1450                 1455

Ser Gly  Lys Pro Glu His Asp  Val Thr Tyr Leu Gln  Gln Leu Val
    1460                 1465                 1470

Glu Asp  Leu Arg Gly Gln Leu  Ser Arg Ser Gln Ala  Leu Ile Arg
    1475                 1480                 1485

Ser Leu  Gln Ala Gln Met Arg  Asp Cys Thr Pro Val  Gly Thr Pro
    1490                 1495                 1500

Arg Lys  Val Asn Trp Gly Leu  Asp Asn Ser Glu Thr  Gln Ser Thr
    1505                 1510                 1515

Ala Glu  Glu Asp Glu Gly Trp  Gln Ser Ser Asp Gly  Phe Gly Ser
    1520                 1525                 1530

Leu Pro  Arg Gln Pro Lys Gln  Asp Arg Glu Leu Gln  Glu Leu Val
    1535                 1540                 1545

Ser Arg  Val Thr Ser Leu Glu  Glu Gln Leu Arg Lys  Gly Lys Gly
    1550                 1555                 1560

His Ala  Asp Asp Gly Lys Asn  Gly Asn Trp Pro Gly  Lys Phe Asp
    1565                 1570                 1575

Thr Leu  Ile Gln Ala Gln Ala  Arg Glu Leu Ser His  Leu Arg Gln
    1580                 1585                 1590

Lys Met  Arg Glu Gly Arg Gly  Met Cys His Ile Leu  Thr Gln His
    1595                 1600                 1605
```

```
Leu Gly  Asp Thr Thr Lys Thr  Phe Glu Glu Leu Leu  Arg Ser Asn
    1610                 1615                 1620

Asp Ile  Asp Tyr Tyr Met Gly  Gln Ser Phe Arg Asp  Gln Leu Ser
    1625                 1630                 1635

Gln Ser  Ile Ser Leu Ala Gln  Arg Val Ser Thr Lys  Ile Ser Gly
    1640                 1645                 1650

Arg Lys  Ser Gln Thr Tyr Ile  Ser Gln Phe Ser Tyr  Lys Asn Ile
    1655                 1660                 1665

Ala Leu  Asn Tyr Phe Ile Leu  Ala Gly Asp His Ser  Glu Val Pro
    1670                 1675                 1680

Asp Asp  Lys Ser Gly His Glu  Leu Leu Ala Ile Arg  Leu Ser Lys
    1685                 1690                 1695

Glu Leu  Gln Gln Lys Asp Lys  Leu Ile Glu Ser Leu  Arg Ser Lys
    1700                 1705                 1710

Leu Asp  Gln Gln Gln Pro Arg  Ser Asp Thr Pro Thr  Ser Ser His
    1715                 1720                 1725

Ala Phe  Ser Val Ala Thr Asp  Gln Ser Asp Arg Thr  Ser Phe Val
    1730                 1735                 1740

Ser Asp  Asp His Gly Ser Thr  Asn Glu Asp Leu Glu  Leu Cys Ser
    1745                 1750                 1755

Glu Leu  Asp Ala Ala Ser Glu  Tyr Gly Gln Glu Glu  Ala Ala Arg
    1760                 1765                 1770

Ser Ala  Thr Asp Pro Arg Asn  Asn Arg Gly Ser Val  Leu Ser His
    1775                 1780                 1785

Pro Ser  Asn Pro Pro Ser Ile  Thr Ser Ser His Ser  His Lys Ser
    1790                 1795                 1800

Thr Asn  Thr Cys Pro Ser Ile  His Cys Thr Pro Arg  Arg Pro Leu
    1805                 1810                 1815

Glu Thr  Gln Glu Gln Thr Val  Asn Ile Pro Asn Glu  Val Asn Ser
    1820                 1825                 1830

Arg Glu  Ser Val Ala Leu Ser  Leu Cys Ala Leu Pro  Ser Gly Leu
    1835                 1840                 1845

Thr Thr  Val Pro Leu Ser Asn  Ser Ile Pro Phe Ser  Ala Ser Leu
    1850                 1855                 1860

His Cys  Pro Gln Met Cys Ser  Gln Pro Val Phe Asp  Pro His Val
    1865                 1870                 1875

His Pro  Leu Arg Thr Arg His  Pro Tyr Gly Gly Gly  Phe Ser Leu
    1880                 1885                 1890

Ala Glu  Val His Gln Glu Leu  Gln Met Leu Gln Arg  Gln Leu Gly
    1895                 1900                 1905

Asn Ser  Tyr His Gly Pro Gln  Met Lys Pro Leu Pro  Ala Phe Pro
    1910                 1915                 1920

Leu Gly  Pro His Ala Gln Pro  Asp His Ser Ser Leu  His Pro Leu
    1925                 1930                 1935

Ser His  His Ala Phe Glu Gln  Ser Pro Leu Asn Ser  Gln His Thr
    1940                 1945                 1950

Ser Pro  Ala Met Lys Ser Gly  Ser Ser Leu Leu Glu  Ser Ser Ala
    1955                 1960                 1965

Met Trp  Asp Met Met Tyr Ser  Pro Arg Pro Leu Arg  Pro Gly Pro
    1970                 1975                 1980

Tyr Gly  Asp Val Ser Ser Gly  Ser Ser Gly Tyr Gln  Ser Gly His
    1985                 1990                 1995

Thr Gly  Thr Asp Leu Met Glu  Glu His Leu Arg Glu  Ile Arg Thr
```

```
    2000                2005                2010

Leu Arg  Arg Arg Leu Glu Asp  Ser Ile Gln Thr Asn  Asp Arg Leu
    2015                2020                2025

Arg Gln  Gln Leu Glu Glu Arg  Leu Ala Ala Ser Ala  Arg Asn Gly
    2030                2035                2040

Gly Ala  Ala Pro Thr Asn Ile  Tyr Ile Gln Gly Leu  Asp Ser Val
    2045                2050                2055

Ser Gln  Leu Ser Asn Glu Ile  Arg Val Leu Lys Glu  Glu Asn His
    2060                2065                2070

Thr Leu  Gln Asn Gln Leu Gln  Gln Ala Arg Thr Asp  Gly Ser Lys
    2075                2080                2085

Glu Met  Glu Arg Leu Arg Glu  Ala Val Leu Ser Val  Arg Gly Gln
    2090                2095                2100

Leu Lys  Gln Ala Glu Leu Glu  Ala Asp Lys Trp Ala  Asp Gln Cys
    2105                2110                2115

Arg Arg  Met Gln Ala Gln Ile  Arg Asp Gln Thr Gln  Thr Val Leu
    2120                2125                2130

Gln Leu  Lys Glu Glu Lys Gln  Asn Ser Leu Asp Asn  Ser Thr Arg
    2135                2140                2145

Leu Gln  Gln Glu Val Asn Val  Leu Gln Gln Gln Leu  Ser Glu Cys
    2150                2155                2160

Gln Cys  Leu Val His Thr Leu  Gln Cys Glu Leu Gln  Val Tyr Lys
    2165                2170                2175

Arg Val  Cys Gly Thr Ala Glu  Ser Asn Ala Gly Ser  Gly Leu Thr
    2180                2185                2190

Leu Thr  Leu Asp Leu Arg Glu  Arg Glu Ser Asn Ile  Gln Leu Leu
    2195                2200                2205

Glu Gln  Gln Leu Arg Glu Arg  Leu Asp Leu Cys Met  Pro His Pro
    2210                2215                2220

Ser Ala  Arg Lys Gln Leu Phe  His Val Asp Gln Ser  Pro Ser Pro
    2225                2230                2235

Pro Val  Arg Asp Thr Gly Phe  Ser Ser Pro Ala Ser  Pro Ala Ile
    2240                2245                2250

Lys Gln  His Asp Pro Lys Pro  Tyr Lys Tyr Ser Gly  Ala Glu Gly
    2255                2260                2265

Leu Glu  Gly Glu Ala Pro Asp  Gly Ser Phe Ala Cys  Arg Thr Gly
    2270                2275                2280

Arg His  Met Ile Ser His Val  Asp Asp Phe Ser Val  Leu Gln Gln
    2285                2290                2295

Gln Leu  Leu Glu Gly Lys Ala  Val Ile Arg Lys Met  Glu Ala Ala
    2300                2305                2310

Leu Gln  Ala Ser Thr Glu Ser  His Asp Leu Pro Glu  Gly Tyr Val
    2315                2320                2325

Arg Asn  Leu Gln Val Ser Thr  Lys Thr Leu Lys Gln  Ile Leu Glu
    2330                2335                2340

Glu Thr  Ser Ser Leu Leu Arg  Met Phe Trp Arg Ala  Ala Leu Pro
    2345                2350                2355

Ser Thr  Glu Thr Ser Ala Gln  Gln Leu Lys Lys Glu  Gln Ser Leu
    2360                2365                2370

Arg Lys  Glu Val Ile Ala Leu  Arg Cys Lys Leu Ser  Glu Gln Glu
    2375                2380                2385

Gln Leu  Leu Arg Asp Thr Met  Glu Asn Leu Arg Ala  Ser Ser Gln
    2390                2395                2400
```

```
Thr Lys  Asp Ser Met Glu Gln  Phe Ile Val Asn Gln  Leu Ser Arg
    2405                 2410                 2415

Thr Arg  Asp Val Leu Lys Gln  Ala Arg Ser Asn Leu  Glu
    2420                 2425                 2430


<210> SEQ ID NO 17
<211> LENGTH: 1208
<212> TYPE: PRT
<213> ORGANISM: Danio rerio

<400> SEQUENCE: 17

Met Tyr Ser Val Val Gly Glu Asp Gln Thr Leu Pro Phe Asp Ile Asn
1               5                   10                  15

Leu Ser Ile Ser Lys Leu Pro Asp Ser Leu Asn Gly Ser Asn Phe Ser
            20                  25                  30

Met Asp Asn Ile Ser Ala Pro Leu Phe Pro Gly Gln Arg Met Ser Pro
        35                  40                  45

Ala Lys Ala Leu Thr Met Lys Asp Tyr Glu Asn Gln Ile Thr Ala Leu
    50                  55                  60

Lys Lys Glu Asn Phe Asn Leu Lys Leu Arg Ile Tyr Phe Leu Glu Glu
65                  70                  75                  80

Arg Val Gln Gln Lys Cys Asp Asp Ser Thr Glu Asp Ile Tyr Lys Thr
                85                  90                  95

Asn Ile Glu Leu Lys Val Glu Val Glu Ser Met Lys Arg Asp Leu Ala
            100                 105                 110

Glu Lys Gln Glu Leu Leu Val Ser Ala Ser Lys Ala Leu Glu Ser Leu
        115                 120                 125

Ala Ser Arg Gly Val Asp Asp Gly Arg Glu Lys Ile Gln Arg Asp Met
    130                 135                 140

Asp Ser Leu Arg Glu Ala Phe Arg Ala Arg Ile Gln Glu Leu Glu Glu
145                 150                 155                 160

Ser Leu Gln Ala Ala Arg Glu Glu Leu Glu Ser Met Ala Thr Ile Ala
                165                 170                 175

Glu Gln Glu Lys Leu Lys Asn Leu Gly Leu Glu Arg Glu Leu Gln Ala
            180                 185                 190

Ala Asn Gln Ser Gly Pro Ser Thr Asp Ser Ser Ser Ala Pro Gln Gln
        195                 200                 205

Val Arg Glu Leu Gln Gln Ala Leu Gln Glu Ser Glu Arg Ala Ile Glu
    210                 215                 220

Gln Leu Gln Ala Ser Leu Arg Asp Gln Asp Gly Val Ile Gly Glu Leu
225                 230                 235                 240

Gln Lys Asn Gly Ser Asn Gln Pro Val Thr Glu Gln Val Met His Leu
                245                 250                 255

Asn Ser Val Ile Val Gln Lys Asp Cys Gln Leu Gln Ala Leu Arg Glu
            260                 265                 270

Glu Leu Asp Gln Gly Lys Glu Asn Ala Glu Arg Asp Lys Gln Ile Ile
        275                 280                 285

Val Asp Arg Gln Asn Glu Leu Ser Arg Leu Glu Gln Lys Thr Arg Gln
    290                 295                 300

Leu Thr Glu Glu Leu Asn Thr Ala Lys Asn Asn Gly Gln Thr Leu Lys
305                 310                 315                 320

Asp Ala Leu Asp Glu Met Glu Lys Glu Lys Lys Ala Leu Ser Asp Glu
                325                 330                 335

Leu Gln Lys Arg Glu Ile Glu Leu Ser Thr Glu Lys Lys Asn Ser Leu
```

-continued

```
            340                 345                 350

Lys Arg Asp Lys Ala Ile Gln Gly Leu Thr Leu Phe Leu Lys Glu Lys
        355                 360                 365

Glu Lys Glu Ile Glu Asp Leu Ser Gly Asp Leu Glu Glu Lys Asp Gln
    370                 375                 380

Ala Leu Ala Lys Ala Arg Glu Ala Leu His Lys Ala Lys Leu Gln Lys
385                 390                 395                 400

Tyr His Gly Ala Glu Asp Gln Gln Ser Leu Leu Leu Glu Gln Gln Ala
                405                 410                 415

Glu Leu Ser Arg Leu Gln Ala Glu Ala His Ser Ser Leu Leu Glu Ala
            420                 425                 430

Gln Arg Leu Gln Arg Val Leu Gly Ser Arg Asp Ser Glu Leu Ser Leu
        435                 440                 445

Leu Gln Gln Ala Lys Leu Gln Leu Glu Gln Glu Leu Glu Gln Leu Gln
    450                 455                 460

Gln Gln Lys Lys Lys Gly Asp Lys Thr Ile Asn Asp Leu Gln Asn Gln
465                 470                 475                 480

Leu Lys Lys Leu Asn Gly Thr Leu Ala Asp Arg Glu Asn Ala Leu Asp
                485                 490                 495

Gln Gln Arg Leu Glu Gln Gln Glu Gln Ile Arg Ala Ser Glu Gln Lys
            500                 505                 510

Met Gln Asn Ala Met Glu Arg Leu Thr Ala Ser Leu Asn His Lys Asp
        515                 520                 525

Gln Gln Leu Gln Asp Tyr Met Asn Met Val Arg Asp Leu Glu Lys Asn
    530                 535                 540

Arg Ser Gln Glu Glu Gly Asp Pro Met Leu Ala Lys Leu Arg Ala Arg
545                 550                 555                 560

Leu Lys Glu Lys Glu Lys Ala Leu Glu Lys Ala Leu Asp Glu Lys Phe
                565                 570                 575

Ala Ala Val Glu Glu Lys Glu Asn Glu Ile His Leu Leu Gln Leu Ser
            580                 585                 590

Leu Arg Glu Lys Glu Arg Asp Val Glu Arg Leu Asn Asn Leu Leu Ser
        595                 600                 605

His Asn Glu Glu Thr Ile Asn Ser Phe Asp Ala Val Ile Lys Glu Arg
    610                 615                 620

Asp Leu Glu Leu Gln Gln Leu Leu Asn Ser Leu Lys Asn Leu Gln Arg
625                 630                 635                 640

Asn Lys Asp Glu Thr Glu Glu Asn Leu Gln Arg Ala Leu Arg Glu Lys
                645                 650                 655

Asp Ala Ile Ile Gln His Leu Gln Gln Ala Leu Asp Asn Lys Thr Lys
            660                 665                 670

Asp Met Glu Glu Met Ala Asn Arg Val Leu Asn Gln Ser Glu Ser Gln
        675                 680                 685

Gly Arg Asp Leu Ala Glu Gln Met Ser Gln Arg Leu Lys Val Thr Glu
    690                 695                 700

Thr Met Leu Ser Glu Ala Val Lys Asp Arg Glu Arg Leu Val Thr Glu
705                 710                 715                 720

Asn Gln Thr Ala Val Glu Asn Leu Leu Ala Thr Ile Arg Ser Lys Asp
                725                 730                 735

Gln Leu Leu Lys Glu Ser Met Glu Arg His Thr His Thr Leu Ser Asp
            740                 745                 750

Arg Ser Ala Glu Met Leu Asp Leu Arg Lys Gln Leu Ser Asp Thr Gln
        755                 760                 765
```

```
Gln Gln Leu Arg Asn Ala Gln Arg Leu Asn Ala Ala Ala Thr Gln Asp
    770                 775                 780

Gly His Leu Glu Ile Ala Glu Leu Arg Ala Met Leu Ser Glu Lys Asp
785                 790                 795                 800

Ala Leu Ile Asn Lys Leu Leu Glu Arg Gly Gln Glu Lys Asp Arg Ile
                805                 810                 815

Leu Phe Glu Met Lys Ser Gly Glu Ala Pro Pro Pro Gln Val Leu Glu
            820                 825                 830

Leu Arg Gln Thr Ile Glu Leu Leu Gln Glu Lys Leu Glu Glu Arg Glu
        835                 840                 845

Ala Glu Leu Ser Arg Arg Asn Ser Glu Glu Met Leu Asp Val Ala Ala
    850                 855                 860

Val Thr Lys Lys Ser Ala Val Leu Leu Lys Arg Glu Leu Leu Gln Lys
865                 870                 875                 880

Thr Asp Ala Leu Asn Ala Ala Leu Lys Arg Glu Asn Gln Leu Lys Ile
                885                 890                 895

Ser Leu Ala Glu Leu Gln Ser Ser Leu Ser Glu Leu Glu Ala Arg Leu
            900                 905                 910

Glu Gly Gln Thr Ala Asn Ile Glu Ser Leu Thr Ser Thr Leu Asp Thr
        915                 920                 925

Lys Glu Glu Ile Ile Thr Glu Leu His His Arg Leu Ser Gln Arg Gly
    930                 935                 940

Asp Ser Arg Val Pro Leu Thr Arg Asp Gln Ala Ser Gln Leu Gly Glu
945                 950                 955                 960

Ser Glu Tyr Ser Pro Ser Ser Leu Pro Gln Arg Glu Thr Thr Ile Ile
                965                 970                 975

Gly Gly Asp Arg Gln Gln Leu Asp Val Ala Ser Leu Ser Asp Leu Arg
            980                 985                 990

Ser Glu Gln Ala Glu Leu Asn Arg  Ala Leu Arg Ala Glu  Gln His Leu
        995                 1000                1005

Tyr Ser  Asp Leu Ile Arg Ala  Val Lys Glu Arg Asp  Ser Val Glu
    1010                1015                1020

Arg Leu  Gln Ala Leu Gln Leu  Glu Leu Thr Ala Val  Ala Leu Leu
    1025                1030                1035

Arg Gln  Gln Leu Glu Ser Gly  Val Gln Met Asn Ser  Glu Leu Arg
    1040                1045                1050

Asp Gln  Leu Gln Thr Glu Ile  His Arg Thr Lys Gln  Arg Glu Gly
    1055                1060                1065

Ser Asn  Pro Ser Glu Leu Gln  Thr Leu Arg Asp Ala  Leu Glu Glu
    1070                1075                1080

Ala Gln  Arg Trp Asn Val Ser  Leu Gln Ala Arg Leu  Gly Gln Ile
    1085                1090                1095

Gln Asp  Arg Gly Gly Gly Val  Gly Gln Ala Asn Asp  Ser Val Asp
    1100                1105                1110

Thr Leu  Ser Met Ile Gly Asp  Gln Thr Ser Tyr Met  Ser Ile Cys
    1115                1120                1125

Val Gly  Glu Gly Pro Glu Glu  Glu Leu Leu His Met  Thr Val Asp
    1130                1135                1140

Gln Leu  Arg Leu Lys Val Leu  Glu Leu Glu Ala Val  Asn Ala Glu
    1145                1150                1155

Leu Gln  Lys Lys Leu Val Leu  Leu Glu Lys Asp Thr  Val Gly Asn
    1160                1165                1170
```

```
Ala Pro  Ile Gly Ser His Ser  Gln Lys Glu Pro Asp  Leu Ile Asp
    1175                 1180                 1185

Leu Ser  Thr Pro Thr Lys Val  Leu Gln Phe Thr Ser  Ser Gly Ala
    1190                 1195                 1200

Cys Phe  Arg Phe His
    1205


<210> SEQ ID NO 18
<211> LENGTH: 1148
<212> TYPE: PRT
<213> ORGANISM: Homo sapiens

<400> SEQUENCE: 18

Pro Pro Pro Pro Pro Pro Arg Glu Ala Cys His Pro Leu Gly Gly Lys
1               5                   10                  15

Met Lys Glu Ile Cys Arg Ile Cys Ala Arg Glu Leu Cys Gly Asn Gln
            20                  25                  30

Arg Arg Trp Ile Phe His Thr Ala Ser Lys Leu Asn Leu Gln Val Leu
        35                  40                  45

Leu Ser His Val Leu Gly Lys Asp Val Pro Arg Asp Gly Lys Ala Glu
    50                  55                  60

Phe Ala Cys Ser Lys Cys Ala Phe Met Leu Asp Arg Ile Tyr Arg Phe
65                  70                  75                  80

Asp Thr Val Ile Ala Arg Ile Glu Ala Leu Ser Ile Glu Arg Leu Gln
                85                  90                  95

Lys Leu Leu Leu Glu Lys Asp Arg Leu Lys Phe Cys Ile Ala Ser Met
            100                 105                 110

Tyr Arg Lys Asn Asn Asp Asp Ser Gly Ala Glu Ile Lys Ala Gly Asn
        115                 120                 125

Gly Thr Val Asp Met Ser Val Leu Pro Asp Ala Arg Tyr Ser Ala Leu
    130                 135                 140

Leu Gln Glu Asp Phe Ala Tyr Ser Gly Phe Glu Cys Trp Val Glu Asn
145                 150                 155                 160

Glu Asp Gln Ile Gln Glu Pro His Ser Cys His Gly Ser Glu Gly Pro
                165                 170                 175

Gly Asn Arg Pro Arg Arg Cys Arg Gly Cys Ala Ala Leu Arg Val Ala
            180                 185                 190

Asp Ser Asp Tyr Glu Ala Ile Cys Lys Val Pro Arg Lys Val Ala Arg
        195                 200                 205

Ser Ile Ser Cys Gly Pro Ser Ser Arg Trp Ser Thr Ser Ile Cys Thr
    210                 215                 220

Glu Glu Pro Ala Leu Ser Glu Val Gly Pro Pro Asp Leu Ala Ser Thr
225                 230                 235                 240

Lys Val Pro Pro Asp Gly Glu Ser Met Glu Glu Glu Thr Pro Gly Ser
                245                 250                 255

Ser Val Glu Ser Leu Asp Ala Ser Val Gln Ala Ser Pro Pro Gln Gln
            260                 265                 270

Lys Asp Glu Glu Thr Glu Arg Ser Ala Lys Glu Leu Gly Lys Cys Asp
        275                 280                 285

Cys Cys Ser Asp Asp Gln Ala Pro Gln His Gly Cys Asn His Lys Leu
    290                 295                 300

Glu Leu Ala Leu Ser Met Ile Lys Gly Leu Asp Tyr Lys Pro Ile Gln
305                 310                 315                 320

Ser Pro Arg Gly Ser Arg Leu Pro Ile Pro Val Lys Ser Ser Leu Pro
                325                 330                 335
```

```
Gly Ala Lys Pro Gly Pro Ser Met Thr Asp Gly Val Ser Ser Gly Phe
            340                 345                 350

Leu Asn Arg Ser Leu Lys Pro Leu Tyr Lys Thr Pro Val Ser Tyr Pro
        355                 360                 365

Leu Glu Leu Ser Asp Leu Gln Glu Leu Trp Asp Asp Leu Cys Glu Asp
    370                 375                 380

Tyr Leu Pro Leu Arg Val Gln Pro Met Thr Glu Glu Leu Leu Lys Gln
385                 390                 395                 400

Gln Lys Leu Asn Ser His Glu Thr Thr Ile Thr Gln Gln Ser Val Ser
                405                 410                 415

Asp Ser His Leu Ala Glu Leu Gln Glu Lys Ile Gln Gln Thr Glu Ala
            420                 425                 430

Thr Asn Lys Ile Leu Gln Glu Lys Leu Asn Glu Met Ser Tyr Glu Leu
        435                 440                 445

Lys Cys Ala Gln Glu Ser Ser Gln Lys Gln Asp Gly Thr Ile Gln Asn
    450                 455                 460

Leu Lys Glu Thr Leu Lys Ser Arg Glu Arg Glu Thr Glu Glu Leu Tyr
465                 470                 475                 480

Gln Val Ile Glu Gly Gln Asn Asp Thr Met Ala Lys Leu Arg Glu Met
                485                 490                 495

Leu His Gln Ser Gln Leu Gly Gln Leu His Ser Ser Glu Gly Thr Ser
            500                 505                 510

Pro Ala Gln Gln Gln Val Ala Leu Leu Asp Leu Gln Ser Ala Leu Phe
        515                 520                 525

Cys Ser Gln Leu Glu Ile Gln Lys Leu Gln Arg Val Val Arg Gln Lys
    530                 535                 540

Glu Arg Gln Leu Ala Asp Ala Lys Gln Cys Val Gln Phe Val Glu Ala
545                 550                 555                 560

Ala Ala His Glu Ser Glu Gln Gln Lys Glu Ala Ser Trp Lys His Asn
                565                 570                 575

Gln Glu Leu Arg Lys Ala Leu Gln Gln Leu Gln Glu Glu Leu Gln Asn
            580                 585                 590

Lys Ser Gln Gln Leu Arg Ala Trp Glu Ala Glu Lys Tyr Asn Glu Ile
        595                 600                 605

Arg Thr Gln Glu Gln Asn Ile Gln His Leu Asn His Ser Leu Ser His
    610                 615                 620

Lys Glu Gln Leu Leu Gln Glu Phe Arg Glu Leu Leu Gln Tyr Arg Asp
625                 630                 635                 640

Asn Ser Asp Lys Thr Leu Glu Ala Asn Glu Met Leu Leu Glu Lys Leu
                645                 650                 655

Arg Gln Arg Ile His Asp Lys Ala Val Ala Leu Glu Arg Ala Ile Asp
            660                 665                 670

Glu Lys Phe Ser Ala Leu Glu Glu Lys Glu Lys Glu Leu Arg Gln Leu
        675                 680                 685

Arg Leu Ala Val Arg Glu Arg Asp His Asp Leu Glu Arg Leu Arg Asp
    690                 695                 700

Val Leu Ser Ser Asn Glu Ala Thr Met Gln Ser Met Glu Ser Leu Leu
705                 710                 715                 720

Arg Ala Lys Gly Leu Glu Val Glu Gln Leu Ser Thr Thr Cys Gln Asn
                725                 730                 735

Leu Gln Trp Leu Lys Glu Glu Met Glu Thr Lys Phe Ser Arg Trp Gln
            740                 745                 750
```

```
Lys Glu Gln Glu Ser Ile Ile Gln Gln Leu Gln Thr Ser Leu His Asp
        755                 760                 765

Arg Asn Lys Glu Val Glu Asp Leu Ser Ala Thr Leu Leu Cys Lys Leu
    770                 775                 780

Gly Pro Gly Gln Ser Glu Ile Ala Glu Glu Leu Cys Gln Arg Leu Gln
785                 790                 795                 800

Arg Lys Glu Arg Met Leu Gln Asp Leu Leu Ser Asp Arg Asn Lys Gln
                805                 810                 815

Val Leu Glu His Glu Met Glu Ile Gln Gly Leu Leu Gln Ser Val Ser
            820                 825                 830

Thr Arg Glu Gln Glu Ser Gln Ala Ala Ala Glu Lys Leu Val Gln Ala
        835                 840                 845

Leu Met Glu Arg Asn Ser Glu Leu Gln Ala Leu Arg Gln Tyr Leu Gly
    850                 855                 860

Gly Arg Asp Ser Leu Met Ser Gln Ala Pro Ile Ser Asn Gln Gln Ala
865                 870                 875                 880

Glu Val Thr Pro Thr Gly Arg Leu Gly Lys Gln Thr Asp Gln Gly Ser
                885                 890                 895

Met Gln Ile Pro Ser Arg Asp Asp Ser Thr Ser Leu Thr Ala Lys Glu
            900                 905                 910

Asp Val Ser Ile Pro Arg Ser Thr Leu Gly Asp Leu Asp Thr Val Ala
        915                 920                 925

Gly Leu Glu Lys Glu Leu Ser Asn Ala Lys Glu Glu Leu Glu Leu Met
    930                 935                 940

Ala Lys Lys Glu Arg Glu Ser Gln Met Glu Leu Ser Ala Leu Gln Ser
945                 950                 955                 960

Met Met Ala Val Gln Glu Glu Glu Leu Gln Val Gln Ala Ala Asp Met
                965                 970                 975

Glu Ser Leu Thr Arg Asn Ile Gln Ile Lys Glu Asp Leu Ile Lys Asp
            980                 985                 990

Leu Gln Met Gln Leu Val Asp Pro  Glu Asp Ile Pro Ala  Met Glu Arg
        995                 1000                1005

Leu Thr  Gln Glu Val Leu Leu  Leu Arg Glu Lys Val  Ala Ser Val
    1010                 1015                 1020

Glu Ser  Gln Gly Gln Glu Ile  Ser Gly Asn Arg Arg  Gln Gln Leu
    1025                 1030                 1035

Leu Leu  Met Leu Glu Gly Leu  Val Asp Glu Arg Ser  Arg Leu Asn
    1040                 1045                 1050

Glu Ala  Leu Gln Ala Glu Arg  Gln Leu Tyr Ser Ser  Leu Val Lys
    1055                 1060                 1065

Phe His  Ala His Pro Glu Ser  Ser Glu Arg Asp Arg  Thr Leu Gln
    1070                 1075                 1080

Val Glu  Leu Glu Gly Ala Gln  Val Leu Arg Ser Arg  Leu Glu Glu
    1085                 1090                 1095

Val Leu  Gly Arg Ser Leu Glu  Arg Leu Asn Arg Leu  Glu Thr Leu
    1100                 1105                 1110

Ala Ala  Ile Gly Gly Ala Ala  Ala Gly Asp Asp Thr  Glu Asp Thr
    1115                 1120                 1125

Ser Thr  Glu Phe Thr Asp Ser  Ile Glu Glu Glu Ala  Ala His His
    1130                 1135                 1140

Ser His  Gln Gln Leu
    1145
```

<210> SEQ ID NO 19
<211> LENGTH: 9
<212> TYPE: PRT
<213> ORGANISM: Artificial sequence
<220> FEATURE:
<223> OTHER INFORMATION: linker sequence

<400> SEQUENCE: 19

Gly Gly Gly Gly Gly Cys Pro Pro Cys
1               5

<210> SEQ ID NO 20
<211> LENGTH: 7
<212> TYPE: PRT
<213> ORGANISM: Artificial sequence
<220> FEATURE:
<223> OTHER INFORMATION: linker sequence

<400> SEQUENCE: 20

Gly Gly Gly Gly Ser Ser Ser
1               5

<210> SEQ ID NO 21
<211> LENGTH: 13
<212> TYPE: PRT
<213> ORGANISM: Artificial sequence
<220> FEATURE:
<223> OTHER INFORMATION: linker sequence

<400> SEQUENCE: 21

Ser Cys Val Pro Leu Met Arg Cys Gly Gly Cys Cys Asn
1               5                   10

<210> SEQ ID NO 22
<211> LENGTH: 14
<212> TYPE: PRT
<213> ORGANISM: Artificial sequence
<220> FEATURE:
<223> OTHER INFORMATION: linker sequence

<400> SEQUENCE: 22

Pro Ser Cys Val Pro Leu Met Arg Cys Gly Gly Cys Cys Asn
1               5                   10

<210> SEQ ID NO 23
<211> LENGTH: 9
<212> TYPE: PRT
<213> ORGANISM: Artificial sequence
<220> FEATURE:
<223> OTHER INFORMATION: linker sequence

<400> SEQUENCE: 23

Gly Asp Leu Ile Tyr Arg Asn Gln Lys
1               5

<210> SEQ ID NO 24
<211> LENGTH: 23
<212> TYPE: PRT
<213> ORGANISM: Artificial sequence
<220> FEATURE:
<223> OTHER INFORMATION: linker sequence

<400> SEQUENCE: 24

Gly Gly Gly Gly Gly Gly Gly Gly Gly Pro Ser Cys Val Pro Leu Met
1               5                   10                  15

Arg Cys Gly Gly Cys Cys Asn
            20

<210> SEQ ID NO 25
<211> LENGTH: 21
<212> TYPE: RNA
<213> ORGANISM: Artificial sequence
<220> FEATURE:
<223> OTHER INFORMATION: siRNA

<400> SEQUENCE: 25
aaccuccagu ggcugaaaga a 21

<210> SEQ ID NO 26
<211> LENGTH: 21
<212> TYPE: RNA
<213> ORGANISM: Artificial sequence
<220> FEATURE:
<223> OTHER INFORMATION: siRNA

<400> SEQUENCE: 26
aagcagagag acagcucuau a 21

<210> SEQ ID NO 27
<211> LENGTH: 8
<212> TYPE: PRT
<213> ORGANISM: Homo sapiens

<400> SEQUENCE: 27

Ile Glu Ala Leu Ser Ile Glu Arg
1 5

<210> SEQ ID NO 28
<211> LENGTH: 9
<212> TYPE: PRT
<213> ORGANISM: Homo sapiens

<400> SEQUENCE: 28

Ile Gln Gln Thr Glu Ala Thr Asn Lys
1 5

<210> SEQ ID NO 29
<211> LENGTH: 9
<212> TYPE: PRT
<213> ORGANISM: Homo sapiens

<400> SEQUENCE: 29

Gln Asp Gly Thr Ile Gln Asn Leu Lys
1 5

<210> SEQ ID NO 30
<211> LENGTH: 12
<212> TYPE: PRT
<213> ORGANISM: Homo sapiens

<400> SEQUENCE: 30

Ala Leu Gln Gln Leu Gln Glu Glu Leu Gln Asn Lys
1 5 10

<210> SEQ ID NO 31
<211> LENGTH: 14
<212> TYPE: PRT
<213> ORGANISM: Homo sapiens

<400> SEQUENCE: 31

Glu Gln Leu Leu Gln Glu Phe Arg Glu Leu Leu Gln Tyr Arg
1 5 10

<210> SEQ ID NO 32
<211> LENGTH: 16
<212> TYPE: PRT
<213> ORGANISM: Homo sapiens

<400> SEQUENCE: 32

Glu Gln Glu Ser Ile Ile Gln Gln Leu Gln Thr Ser Leu His Asp Arg
1 5 10 15

<210> SEQ ID NO 33
<211> LENGTH: 8
<212> TYPE: PRT
<213> ORGANISM: Homo sapiens

<400> SEQUENCE: 33

Asn Ser Glu Leu Gln Ala Leu Arg
1 5

<210> SEQ ID NO 34
<211> LENGTH: 12
<212> TYPE: PRT
<213> ORGANISM: Homo sapiens

<400> SEQUENCE: 34

Gln Thr Asp Gln Gly Ser Met Gln Ile Pro Ser Arg
1 5 10

<210> SEQ ID NO 35
<211> LENGTH: 14
<212> TYPE: PRT
<213> ORGANISM: Homo sapiens

<400> SEQUENCE: 35

Ser Thr Leu Gly Asp Leu Asp Thr Val Ala Gly Leu Glu Lys
1 5 10

<210> SEQ ID NO 36
<211> LENGTH: 9
<212> TYPE: PRT
<213> ORGANISM: Homo sapiens

<400> SEQUENCE: 36

Leu Thr Gln Glu Val Leu Leu Leu Arg
1 5

<210> SEQ ID NO 37
<211> LENGTH: 9
<212> TYPE: PRT
<213> ORGANISM: Homo sapiens

<400> SEQUENCE: 37

Leu Asn Glu Ala Leu Gln Ala Glu Arg
1 5

<210> SEQ ID NO 38
<211> LENGTH: 13
<212> TYPE: PRT
<213> ORGANISM: Homo sapiens

<400> SEQUENCE: 38

Thr Leu Gln Val Glu Leu Glu Gly Ala Gln Val Leu Arg
1 5 10

-continued

```
<210> SEQ ID NO 39
<211> LENGTH: 16
<212> TYPE: PRT
<213> ORGANISM: Homo sapiens

<400> SEQUENCE: 39

Leu Glu Thr Leu Ala Ala Ile Gly Gly Gly Glu Leu Glu Ser Val Arg
1               5                   10                  15
```

MYOMEGALIN VARIANT 8

CROSS-REFERENCE TO RELATED APPLICATION

This application is the U.S. national stage application of International Patent Application No. PCT/CN2011/001907, filed Nov. 15, 2011, which claims the benefit of U.S. Provisional Patent Application No. 61/344,927, filed Nov. 19, 2010, the disclosures of each of which are hereby incorporated by reference in their entirety.

BACKGROUND OF THE INVENTION

The Golgi apparatus is a membranous organelle that plays a pivotal role in protein post-translational modification, sorting, and transport. In interphase animal cells, the Golgi apparatus manifests a crescent moon shaped, ribbon-like morphology in the perinuclear region, normally situated closely with centrosomes.

Microtubule cytoskeleton plays an essential role in the organization, positioning, and function of the Golgi apparatus (Rios and Bornens, *Curr. Opin. Cell Biol.* 15:60-66 (2003); Sutterlin and Colanzi, *J. Cell Biol.* 188:621-628 (2010); Lippincott-Schwartz, *Curr. Opin. Cell Biol.* 10:52-59 (1998)). Microtubule depolymerization causes severe Golgi defects, such as endoplasmic reticulum (ER)-to-Golgi transport blockage and Golgi fragmentation (Cole et al., *Mol. Biol. Cell.* 7:631-650 (1996); Miller et al., *Nat. Cell Biol.* 11:1069-1080 (2009)). The Golgi apparatus undergoes disassembly and reassembly during mitosis. During reassembly, microtubules derived from the Golgi apparatus and centrosomes facilitate the Golgi apparatus to form into a continuous ribbon structure with the central cellular positioning from Golgi ministacks (Miller et al., *Nat. Cell Biol.* 11:1069-1080 (2009)).

The Golgi apparatus serves as a major microtubule-organizing center (Chabin-Brion et al., *Mol. Biol. Cell.* 12:2047-2060 (2001); Efimov et al., *Dev. Cell.* 12:917-930 (2007); Miller et al., *Nat. Cell Biol.* 11:1069-1080 (2009); Rivero et al., *EMBO J.* 28:1016-1028 (2009)). In humans, almost half of cellular microtubules originate from the Golgi apparatus as observed in retinal pigment epithelial cells RPE1 (Efimov et al., *Dev. Cell.* 12:917-930 (2007)). Golgi-associated microtubules are also required for Golgi ribbon assembly, directional trafficking, and cell motility (Miller et al., *Nat. Cell Biol.* 11:1069-1080 (2009); Rivero et al., *EMBO J.* 28:1016-1028 (2009)). Microtubule nucleation at the Golgi apparatus does not require centrosomes; rather, it depends on γ-tubulin (Efimov et al., *Dev. Cell.* 12:917-930 (2007)), the principal microtubule nucleator that exists as γ-tubulin complexes (γTuCs). γTuCs associate with two cis-Golgi proteins, GMAP-210 and AKAP450 (AKAP450 is also known as AKAP350, CG-NAP, and hyperion) (Rios et al., Cell 118:323-335 (2004); Rivero et al., *EMBO J.* 28:1016-1028 (2009); Takahashi et al., *Mol. Biol. Cell* 13:3235-3245 (2002)). It is reported that silencing AKAP450 expression blocks the Golgi-associated microtubule nucleation (Rivero et al., *EMBO J.* 28:1016-1028 (2009)).

Golgi-nucleated microtubules are required for post-Golgi secretion and directional cell migration. In the secretory pathway, protein transport from the ER to the Golgi apparatus is initiated by cargo packaging into COPII-coated vesicles at ER exit sites, followed by the formation of vesicular-tubular clusters or the ER-Golgi intermediate compartment that move along microtubules towards the Golgi apparatus. Defects of protein secretion can cause a number of diseases, including neuronal disorders and diabetes. In addition, as microtubules are involved in cell migration, suppression of microtubule nucleation may be used to inhibit tumor metastasis.

EB1 is the prototypic member of EB proteins, which are localized to microtubules and track growing microtubule plus-ends (Akhmanova and Steinmetz, *Nat. Rev. Mol. Cell Biol.* 9:309-322 (2008); Vaughan, *J. Cell Biol.* 171:197-200 (2005)). Among the EB proteins, EB1 and EB3 display similar tip-tracking properties, whereas EB2 appears to be distinct from the other two, exhibiting a considerably weaker tip-tracking activity (Komarova et al., *J. Cell Biol.* 184:691-706 (2009)).

EB1 is found on all growing microtubule tips, where it acts as a key component of plus-end protein complexes through its interaction with various plus-end tracking proteins (+TIPs). Many +TIPs contain the SxIP motif surrounded by basic and serine-rich sequences for interaction with the EBH domain of EB1 (Honnappa et al., *Cell* 138:366-376 (2009)). This SxIP-EB1 interaction relieves EB1 autoinhibition, and is required for EB1 in its action for promoting microtubule polymerization (Honnappa et al., *EMBO J.* 24:261-269 (2005); Honnappa et al., *Cell* 138:366-376 (2009); Slep et al., *J. Cell Biol.* 168:587-598 (2005)). +TIPs in association with EB1 at the microtubule plus-ends have diverse functions, including regulation of microtubule dynamics and microtubule attachment to subcellular targets (Akhmanova and Steinmetz, *Nat. Rev. Mol. Cell Biol.* 9:309-322 (2008)).

In a yeast two-hybrid screen, myomegalin (MMG) isoform 1 (Genbank accession: NP_055459) was cloned to interact with cyclic nucleotide phosphodiesterase 4D, and was identified as a phosphodiesterase 4D-interacting protein (Verde et al., *J. Biol. Chem.* 276:11189-11198 (2001)). The MMG1 nucleotide sequence encodes a ~230 kDa protein that is highly expressed in heart and skeletal muscles. In gene databases, MMG1 is the only known human homolog of CDK5RAP2 (CDK5 regulatory subunit-associated protein 2), a human microcephaly-related protein involved in microtubule organization in centrosomes as well as microtubule regulation at the growing tips (Fong et al., *Mol. Biol. Cell.* 19:115-125 (2008); Fong et al., *Mol. Biol. Cell.* 20:3660-3670 (2009)). MMG isoform 1 displays centrosome and Golgi-localizing patterns similar to CDK5RAP2 (Verde et al., *J. Biol. Chem.* 276:11189-11198 (2001); Wang et al., *J. Biol. Chem.* 285:22658-22665 (2010)).

Despite the apparent importance of the Golgi apparatus in various cellular activities such as protein modification and trafficking, microtubule organization, and cell migration, the precise mechanisms of how the Golgi apparatus exerts these functions have not been fully elucidated. Specifically, it remains unclear how γTuCs are targeted to the Golgi apparatus. In addition, it remains unclear whether EB1 and other EB members are present at the Golgi apparatus to exert their functions. As will be clear from the disclosures that follow, these and other benefits are provided by the present invention.

SUMMARY OF THE INVENTION

The present invention provides novel myomegalin (MMG) isoforms, nucleic acid molecules encoding the myomegalin isoforms, fusion constructs comprising the myomegalin isoforms, and antibodies that bind specifically to the myomegalin isoforms. The myomegalin isoforms regulate microtubule organization and nucleation at the Golgi apparatus; protein modification, secretion, and transport; and cell proliferation.

In one embodiment, the present invention provides a myomegalin isoform, myomegalin variant 8 (MMG8), comprising SEQ ID NO:2. The present invention also provides MMG8 variants. In one embodiment, the MMG8 variant comprises amino acids 1-389 of SEQ ID NO:2. In some embodiments, the MMG8 variant comprises a polypeptide comprising amino acids 1-389 of SEQ ID NO:2, wherein the carboxy-terminus comprises amino acids 1098-1116 of SEQ ID NO:2 or a contiguous fragment of amino acids 1098-1116 of SEQ ID NO:2.

In one embodiment, the present invention provides a nucleic acid molecule encoding MMG8 comprising SEQ ID NO:2, or a fragment thereof, or any complement thereof. In an embodiment, the nucleic acid molecule comprises SEQ ID NO:1. Also provided are vectors, expression constructs, and host cells comprising the nucleic acid molecules of the invention.

In one embodiment, the present invention provides fusion proteins comprising MMG8 or an MMG8 variant, or a fragment thereof, a second protein, and optionally, a linker sequence that links the MMG8, MMG8 variant or fragment thereof to the second protein.

In one embodiment, the present invention provides antibodies that bind specifically to MMG8 comprising SEQ ID NO:2. In a specific embodiment, the antibody of the present invention binds specifically to an epitope comprising 926-1116 of SEQ ID NO:2, or an epitope comprising a fragment of 926-1116 of SEQ ID NO:2. In a preferred embodiment, the anti-MMG8 antibody is a humanized antibody.

The present invention also provides uses of the myomegalin isoform as a diagnostic biomarker and as a target for screening for therapeutic agents for lysosomal storage diseases, diabetes, and cancer. Also provided are methods for treating diseases associated with myomegalin by modulating the expression or activity of the myomegalin isoform of the invention.

BRIEF DESCRIPTION OF THE SEQUENCES

Figure 1:
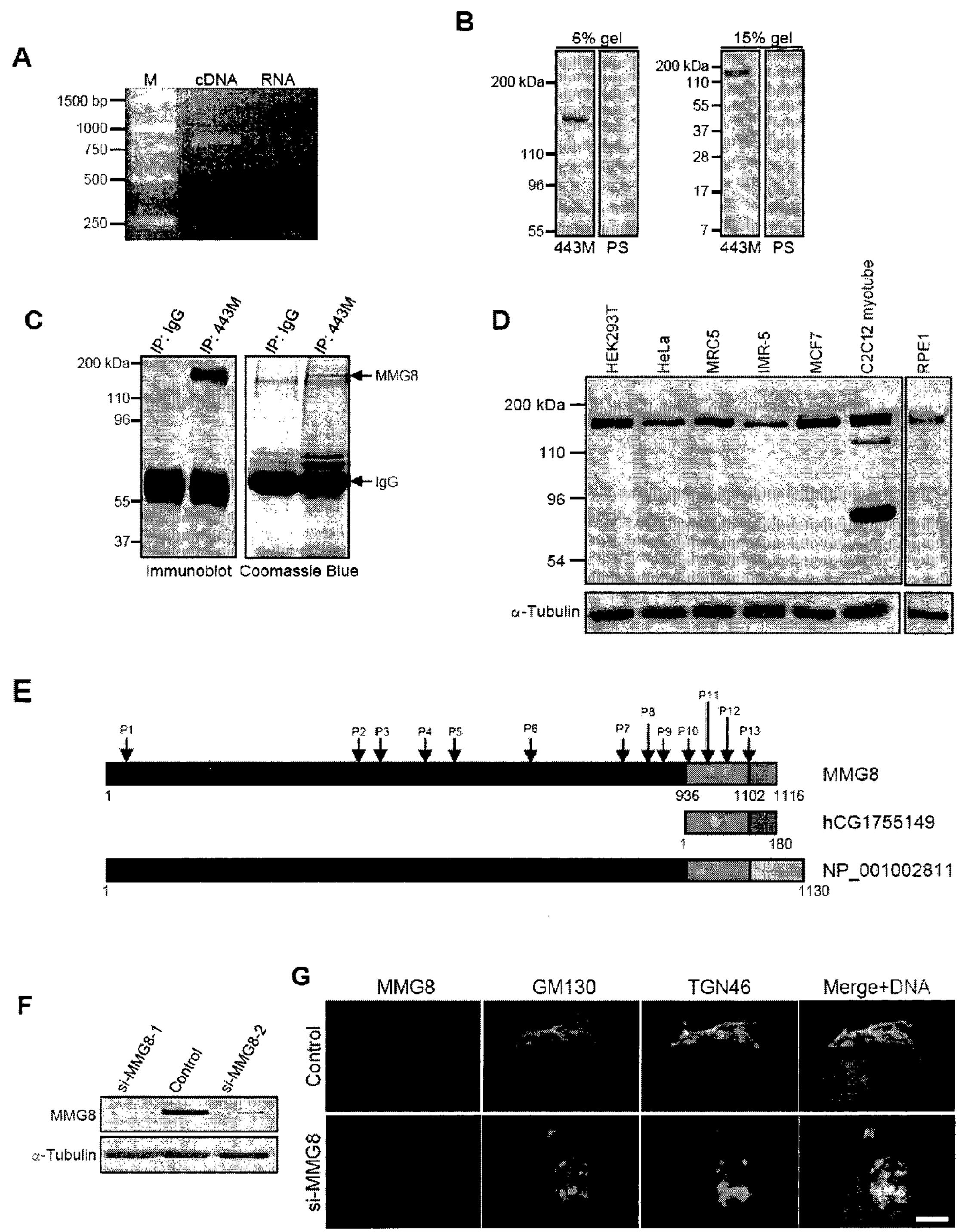
FIG. 1 shows that MMG8, a novel MMG isoform that localizes to cis-Golgi networks, is required for maintaining Golgi integrity. (A) An RT-PCR reaction was performed using oligonucleotide primers targeting a region encoding 474-762 of human MMG isoform 1. This targeted region is present in all currently-identified large sequences of MMG variants. The total RNA was extracted from HeLa cells. In the schematic representation, the region amplified in the RT-PCR and those targeted by the antibodies are labeled. The hatched region corresponds to amino acids 474-762 of MMG isoform 1 and 637-925 of MMG8. M, DNA Marker. (B) HeLa extracts resolved by SDS-PAGE (6% and 15% gels) were probed with the anti-MMG8 antibody 443M or the preimmune serum (PS). (C) Immunoprecipitations (IPs) were performed with 443M and nonspecific IgG. The immunoprecipitated proteins were resolved by SDS-PAGE for anti-MMG8 immunoblotting or Coomassie Blue staining. The protein of ~150 kDa was excised for sequencing by mass spectrometry. (D) MMG expression was examined in cell cultures by immunoblotting using 443M. (E) A schematic representation of the MMG variants. Identical sequences are labelled in same pattern. P1-13 denote peptides sequenced by mass spectrometry. (F) Immunoblotting of HeLa cells transfected with control or MMG8-targeting siRNAs. The transfection of si-MMG8-1 or si-MMG8-2 suppressed the expression of MMG8 by ~85%. (G) HeLa cells transfected with siRNAs were analyzed by immunofluorescence microscopy. Scale bars, 5 μm.

SEQ ID NO:1 is a nucleic acid sequence encoding the human myomegalin isoform of the present invention.

SEQ ID NO:2 is an amino acid sequence of the human myomegalin isoform of the present invention.

SEQ ID NO:3 is an amino acid sequence of a human myomegalin isoform (GenBank Accession No. NP_055459.4).

SEQ ID NO:4 is an amino acid sequence of a human myomegalin isoform (GenBank Accession No. NP_001002812.1).

SEQ ID NO:5 is an amino acid sequence of a human myomegalin isoform (GenBank Accession No. NP_071754.3).

SEQ ID NO:6 is an amino acid sequence of a human myomegalin isoform (GenBank Accession No. NP_001002810.1).

SEQ ID NO:7 is an amino acid sequence of a human myomegalin isoform (GenBank Accession No. NP_001002811.1).

SEQ ID NO:8 is an amino acid sequence of a human myomegalin isoform (GenBank Accession No. NP_001182189.1).

SEQ ID NO:9 is an amino acid sequence of a human myomegalin isoform (GenBank Accession No. NP_001182190.1).

SEQ ID NO:10 is an amino acid sequence of a human myomegalin isoform (GenBank Accession No. NP_001185761.1).

SEQ ID NO:11 is an amino acid sequence of a human myomegalin isoform (GenBank Accession No. NP_001185763.1).

SEQ ID NO:12 is an amino acid sequence of a *Pongo abelii* myomegalin isoform (GenBank Accession No. NP_001126198).

SEQ ID NO:13 is an amino acid sequence of a mouse myomegalin isoform (GenBank Accession No. AAI41173).

SEQ ID NO:14 is an amino acid sequence of a *Gallus gallus* myomegalin isoform (GenBank Accession No. XP_423459).

SEQ ID NO:15 is an amino acid sequence of an *Xenopus tropicalis* myomegalin isoform (GenBank Accession No. NP_001072886).

SEQ ID NO:16 is an amino acid sequence of a *Danio rerio* myomegalin isoform (GenBank Accession No. CAI11891).

SEQ ID NO:17 is an amino acid sequence of a *Danio rerio* myomegalin isoform (GenBank Accession No. NP_956195).

SEQ ID NO:18 is an amino acid sequence of a KIAA0477 protein (GenBank Accession No. KIAA0477).

SEQ ID NO:19 is a linker sequence useful according to the present invention.

SEQ ID NO:20 is a linker sequence useful according to the present invention.

SEQ ID NO:21 is a linker sequence useful according to the present invention.

SEQ ID NO:22 is a linker sequence useful according to the present invention.

SEQ ID NO:23 is a linker sequence useful according to the present invention.

SEQ ID NO:24 is a linker sequence useful according to the present invention.

SEQ ID NO:25 is an siRNA useful to the present invention.

SEQ ID NO:26 is an siRNA useful to the present invention.

SEQ ID NO:27 is an amino acid sequence of a fragment of the human myomegalin isoform of the present invention.

SEQ ID NO:28 is an amino acid sequence of a fragment of the human myomegalin isoform of the present invention.

SEQ ID NO:29 is an amino acid sequence of a fragment of the human myomegalin isoform of the present invention.

SEQ ID NO:30 is an amino acid sequence of a fragment of the human myomegalin isoform of the present invention.

SEQ ID NO:31 is an amino acid sequence of a fragment of the human myomegalin isoform of the present invention.

SEQ ID NO:32 is an amino acid sequence of a fragment of the human myomegalin isoform of the present invention.

SEQ ID NO:33 is an amino acid sequence of a fragment of the human myomegalin isoform of the present invention.

SEQ ID NO:34 is an amino acid sequence of a fragment of the human myomegalin isoform of the present invention.

SEQ ID NO:35 is an amino acid sequence of a fragment of the human myomegalin isoform of the present invention.

SEQ ID NO:36 is an amino acid sequence of a fragment of the human myomegalin isoform of the present invention.

SEQ ID NO:37 is an amino acid sequence of a fragment of the human myomegalin isoform of the present invention.

SEQ ID NO:38 is an amino acid sequence of a fragment of the human myomegalin isoform of the present invention.

SEQ ID NO:39 is an amino acid sequence of a fragment of the human myomegalin isoform of the present invention.

Detailed Description

The present invention provides novel myomegalin isoforms (MMG), nucleic acid molecules encoding the myomegalin isoforms, fusion constructs comprising the myomegalin isoforms, and antibodies that bind specifically to the myomegalin isoforms. In a specific embodiment, the present invention provides a novel MMG isoform, myomegalin variant 8 (MMG8), comprising SEQ ID NO:2. The myomegalin isoforms of the present invention regulate microtubule organization and nucleation at the Golgi apparatus; protein modification, secretion, and transport; and cell proliferation.

The present invention also provides uses of the myomegalin isoform as a diagnostic biomarker and as a target for screening for therapeutic agents for lysosomal storage diseases, diabetes, and cancer. Also provided are methods for treating diseases associated with myomegalin by modulating the expression or activity of the myomegalin isoform of the invention.

Specifically, the present invention provides methods for isolating protein complexes containing MMG8 and uses of MMG8 for regulating protein transport and glycosylation, and inhibiting cell proliferation. MMG8 is a splicing variant of MMG gene (1q12, human genome), and is the major MMG isoform expressed in all cell lines examined by the present inventors and also in C2C12 myotubes. MMG8 is predominantly present in the cis-Golgi networks, and is required for Golgi organization and microtubule nucleation at the Golgi apparatus. MMG8 forms a complex with AKAP450 at the cis-side of the Golgi apparatus to exert its functions. For example, MMG8 binds to γTuCs and is required for γTuCs localization to the Golgi apparatus for microtubule nucleation. MMG8 also interacts with EB1/EB3. The interaction recruits EB1 to the Golgi apparatus and mediates the association of microtubules with MMG8 at the Golgi apparatus.

MMG8 also plays an important role in ER-to-Golgi transport of the protein secretory pathway. The suppression of MMG8 expression induces the accumulation of LAMP-1—a diagnostic marker of lysosomal storage diseases, and reduces glycosylated mature CD44—a therapeutic target of metastatic tumors. In addition, the suppression of MMG8 expression inhibits proliferation of cancer cell lines. Microtubules have been used as a target for screening for anti-cancer agents. MMG8 can be used as a diagnostic marker and target of screening for therapeutic agents.

MMG8 Isoform and Variants

In one aspect, the present invention provides a novel human myomegalin (MMG), herein referred to as myomegalin variant 8 (MMG8), consisting of SEQ ID NO:2. The present invention also provides MMG8 "variants" comprising SEQ ID NO:2 or fragments thereof.

It is discovered that the naturally-occurring human MMG8 isoform is expressed in a variety of cell types, including proliferating epithelial, fibroblast, and neuroblastoma cells. In contrast, another human myomegalin isoform, MMG1 (SEQ ID NO: 3), is expressed in heart and skeletal muscles, but is not expressed or is only minimally expressed in proliferating epithelial, fibroblast, and cancer cells, when compared to the expression levels of the MMG8 isoform of SEQ ID NO:2.

In some embodiments, the present invention provides MMG8 variants. In preferred embodiments, the MMG8 variants bind to one or more of AKAP450, EB1, EB3, and subunits of the γ-tubulin complexes such as GCP2 and GCP3. The MMG8 variant of the subject invention is preferably of mammalian origin, more preferably, of human origin.

In an embodiment, the MMG8 variant comprises amino acids 1-389 of SEQ ID NO:2. In some embodiments, the MMG8 variant of the present invention comprises a polypeptide comprising amino acids 1-389 of SEQ ID NO:2, wherein the carboxy-terminus comprises amino acids 1098-1116 of SEQ ID NO:2 or a fragment comprising 1, 2, 3, 4, 5, 6, 7, 8, 9, 10, 11, 12, 13, 14, 15, 16, 17, or 18 contiguous amino acids of 1098-1116 of SEQ ID NO:2. For example, in certain embodiments, the carboxy-terminus of the MMG8 variant comprises a contiguous fragment starting at any of the amino acids 1098 to 1115 of SEQ ID NO:2, extends through, and terminates at, any of the amino acids 1099 to 1116 of SEQ ID NO:2. For example, in a specific embodiment, the carboxy-terminus of the MMG8 variant comprises amino acids 1103-1116 of SEQ ID NO:2, or a fragment comprising 1, 2, 3, 4, 5, 6, 7, 8, 9, 10, 11, 12, or 13 contiguous amino acids of 1103-1116 of SEQ ID NO:2.

In some embodiments, the MMG8 variant comprises a polypeptide having a sequence that is at least about 90%, 93%, 95%, 96%, 97%, 97.5%, 98%, 98.5%, 99%, or 99.5% identical to SEQ ID NO:2. In some embodiments, the MMG8 variant comprises a sequence that is at least 90%, 93%, 95%, 96%, 97%, 97.5%, 98%, 98.5%, 99%, or 99.5% identical to amino acids 1-389 of SEQ ID NO:2. In an embodiment, the MMG8 variant comprises the SxIP motif (Ser-x-Ile-Pro).

In some embodiments, the MMG8 variants of the present invention do not encompass any of SEQ ID NOs: 3-18. In some other embodiments, the MMG8 variants of the present invention do not encompass a polypeptide comprising a fragment of more than 10, 20, 30, 40, 50, 60, 70, 80, 90, 100, 200, 300, 400, 500, 600, 700, 800, 900, 1000, 1100 contiguous amino acids of any of SEQ ID NOs: 3-18.

A protein or polypeptide fragment, as used herein, unless explicitly specified otherwise, refers to a sequence comprising at least 250, 255, 260, 265, 270, 275, 280, 285, 290, 295, 300, 350, 389, 400, 500, 600, 700, 800, 900, or 1000 contiguous amino acids of a given protein or polypeptide sequence.

Unless otherwise specified, as used herein, percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

In some embodiments, the present invention provides MMG8 variants, wherein one or more amino acids of SEQ ID NO:2, or of a fragment thereof, are modified. Modification of amino acid sequences includes, but is not limited to, addition, deletion, and conservative substitution of amino acids of a given protein or polypeptide sequence. Based on the common knowledge of MMG structure, some amino acids of SEQ ID NO:2 may be substituted, deleted, or added, without detracting from the biological activities of the protein.

In some embodiments, the modification of amino acids is performed at amino acids 390-1116 of SEQ ID NO:2, amino acids 390-1097 of SEQ ID NO:2, or amino acids 390-1102 of SEQ ID NO:2. In an embodiment, the SxIP motif of SEQ ID NO:2 (amino acids 309, 311, and 312) is not modified.

In some embodiments, no more than 50 (e.g., no more than: 50, 45, 40, 35, 30, 25, 20, 15, 14, 13, 12, 11, 10, 9, 8, 7, 6, 5, 4, 3, 2, or 1) amino acids of SEQ ID NO:2 are modified. In some embodiments, no more than 50 (e.g., no more than: 50, 45, 40, 35, 30, 25, 20, 15, 14, 13, 12, 11, 10, 9, 8, 7, 6, 5, 4, 3, 2, or 1) amino acids of 1-389 of SEQ ID NO:2 are modified. In some embodiments, no more than 10, 9, 8, 7, 6, 5, 4, 3, 2, or 1 amino acids of 1098-1116 of SEQ ID NO:2 are modified.

Methods of conservative modifications are known in the art. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

Conservative modifications can produce molecules having functional and chemical characteristics similar to those of the molecule from which such modifications are made. In addition, substantial modifications in the functional and/or chemical characteristics of the molecules may be accomplished by selecting substitutions in the amino acid sequence that differ significantly in their effect on maintaining (a) the structure of the molecular backbone in the area of the substitution, for example, as a sheet or helical conformation, (b) the charge or hydrophobicity of the molecule at the target site, or (c) the size of the molecule. Therefore, it is possible to modify the amino acid sequences of the subject protein to obtain protein homologues with similar, or even more desirable properties. These modified proteins are within the scope of the present invention.

In certain embodiments, conservative amino acid substitutions also encompass non-naturally occurring amino acid residues which are typically incorporated by chemical peptide synthesis rather than by synthesis in biological systems. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Modifications of amino acid residues can also be achieved by direct mutation, phage display, or shuffling within the nucleic acids encoding the protein molecules, which are well known to those skilled in the art. In random mutagenesis, positions are chosen randomly or amino acid changes are made using simplistic rules. In addition, the amino acid derivative may contain substituted or non-substituted, linear, branched, or cyclic alkyl moieties, and may include one or more heteroatoms.

In an embodiment, the present invention provides isolated MMG8 and MMG8 variants. MMG8 and MMG8 variants can be isolated from epithelial cells, fibroblast cells, cancer or tumor cells, or cells undergoing division or proliferation.

The isolated MMG8 and MMG8 variants are substantially free of other cellular components, such as other biological molecules, proteins or peptides, nucleic acids, lipids and carbohydrates, which may normally be associated with MMG8 and MMG8 variants. The term "substantially free of," as used herein, encompasses preparations having less than about 20%, 10%, and preferably less than 5% (by dry weight) contaminating factors (such as biological molecules, proteins or peptides, nucleic acids, lipids, and carbohydrates and other cellular components).

The present invention also provides recombinant forms of MMG8 and MMG8 variants. In one embodiment, the MMG8 is encoded by a polynucleotide comprising SEQ ID NO:1. Proteins or peptides that are recombinantly-produced may be subject to post-translational modification such as glycosylation. The nature and extent of such modifications in large part will be determined by the post-translational modification capacity of the particular host cell and the modification signals that are present in the amino acid sequence of the peptide or protein in question. For instance, glycosylation patterns may vary between different types of host cell. Alternatively, unglycosylated proteins may be generated by expression in a system which is defective for glycosylation.

Fusion Constructs

In another aspect, the present invention provides fusion proteins comprising MMG8 or an MMG8 variant or a fragment thereof, a second protein, and optionally, a linker sequence that links the MMG8, MMG8 variant, or fragment thereof to the second protein.

In an embodiment, the N-terminal of the MMG8 protein or polypeptide is fused with a second protein, optionally, through a linker sequence. In another embodiment, the C-terminal of the MMG8 protein or polypeptide is fused with a second protein, optionally, through a linker sequence.

In a specific embodiment, the fusion protein comprises an MMG8 protein, wherein the MMG8 protein comprises SEQ ID NO:2. In an embodiment, the fusion protein comprises an MMG8 fragment, wherein the fragment comprises amino acids 1-389 of SEQ ID NO:2. In an embodiment, the fusion protein comprises an MMG8 variant, wherein in the MMG8 variant, no more than 50 (e.g., no more than: 50, 45, 40, 35, 30, 25, 20, 15, 14, 13, 12, 11, 10, 9, 8, 7, 6, 5, 4, 3, 2, or 1) amino acids of 1-389 of SEQ ID NO:2 are modified. In one embodiment, the fusion protein comprises MMG8 or an MMG8 variant, wherein the SxIP domain of MMG8 or MMG8 variant is not modified.

In an embodiment, the fusion protein comprises an MMG8 protein, the carboxy-terminus of which comprises a sequence comprising amino acids 1098-1116 of SEQ ID NO:2, or a fragment comprising 1, 2, 3, 4, 5, 6, 7, 8, 9, 10, 11, 12, 13, 14, 15, 16, 17, or 18 contiguous amino acids of 1098-1116 of SEQ ID NO:2. In another embodiment, the fusion protein comprises an MMG8 protein, the carboxy-terminus of which comprises a sequence comprising amino acids 1103-1116 of SEQ ID NO:2, or a fragment comprising 1, 2, 3, 4, 5, 6, 7, 8, 9, 10, 11, 12, or 13 contiguous amino acids of 1103-1116 of SEQ ID NO:2.

In some embodiments, the MMG8 protein or polypeptide is fused with a second protein that is an Fc domain. The term "Fc domain" encompasses the full length and fragments of native human and animal Fc and Fc variant molecules and sequences, including for example IgG, IgM, IgD, IgE, IgA and subtypes such as for example IgG1, IgG2, IgG3, IgG4, IgA1, and IgA2. As with Fc variants and native Fc's, the term "Fc domain" includes molecules in monomeric or multimeric form, whether digested from whole antibody or produced by other means.

The term "Fc variant" refers to a molecule or sequence that is modified from a native Fc, but still comprises a binding site for the salvage receptor. Fc domains include molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined below) such a native Fc.

The Fc domain within the scope of the invention can be of antibodies of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes. In a specific embodiment, the Fc domain is IgG1.

In another embodiment, the fusion protein of the present invention comprises a linker sequence that links the MMG8 protein or polypeptide to a second protein such as an Fc domain. Linker would typically be a peptide chain. The length of the peptide may be, for example, 6, 7, 8, 9, 10, 11, 12, 13, 14, 15, 16, 17, 18, 19, 20, 21, 22, 23, 24, 25, 30, 40, 50 or more amino acid residues, but typically is between 5 and 25 residues. Depending upon the length and side chain composition, a linker may have, but need not have, greater than average flexibility. Flexibility can be calculated using algorithms known in the art. Examples of useful linkers include, but are not limited to, 5GlyCys2ProCys (SEQ ID NO:19), 4Gly3Ser (SEQ ID NO:20), Ser Cys Val Pro Leu Met Arg Cys Gly Gly Cys Cys Asn (SEQ ID NO:21), Pro Ser Cys Val Pro Leu Met Arg Cys Gly Gly Cys Cys Asn (SEQ ID NO:22), Gly Asp Leu Ile Tyr Arg Asn Gln Lys (SEQ ID NO:23), and 9GlyProSerCysValProLeuMetArgCysGlyGlyCysCysAsn (SEQ ID NO:24).

Nucleic Acid Molecules

Another aspect of the invention pertains to nucleic acid molecules that encode the MMG8 or MMG8 variants, fragments, fusion proteins, and antibodies of the present invention. The nucleic acid molecules of the present invention encompass DNA molecules (e.g. genomic DNA and cDNA)

and RNA molecules (e.g. mRNA including pre-mRNA and mature mRNA). In addition, the subject nucleic acid molecules may be single-stranded or double-stranded.

In an embodiment, the nucleic acid molecule of the present invention encodes MMG8 having an amino acid sequence comprising SEQ ID NO:2. In an embodiment, the nucleic acid molecule of the present invention encodes an MMG8 variant comprising amino acids 1-389 of SEQ ID NO:2. In an embodiment, the nucleic acid molecule encodes an MMG8 variant, the carboxy-terminus of which comprises amino acids 1098-1116 of SEQ ID NO:2, or a fragment comprising 1, 2, 3, 4, 5, 6, 7, 8, 9, 10, 11, 12, 13, 14, 15, 16, 17, or 18 contiguous amino acids of 1098-1116 of SEQ ID NO:2. In an embodiment, the nucleic acid molecule encodes an MMG8 variant, the carboxy-terminus of which comprises amino acids 1103-1116 of SEQ ID NO:2, or a fragment comprising 1, 2, 3, 4, 5, 6, 7, 8, 9, 10, 11, 12, or 13 contiguous amino acids of 1103-1116 of SEQ ID NO:2.

In an embodiment, the nucleic acid molecule of the present invention comprises SEQ ID NO:1 or a fragment thereof, wherein the nucleic acid molecule encodes MMG8 or an MMG8 variant. In an embodiment, the nucleic acid molecule of the present invention comprises nucleic acids 1-1167 of SEQ ID NO:1, or a fragment thereof, or any complement thereof. In some embodiments, the nucleic acid molecule comprises a polynucleotide, wherein the 3' end of the polynucleotide sequence comprises 3292-3348 of SEQ ID NO:1, or a contiguous fragment of 3292-3348 of SEQ ID NO:1, or any complement thereof. In some embodiments, the nucleic acid molecule comprises a polynucleotide, wherein the 3' end of the polynucleotide sequence comprises 3309-3348 of SEQ ID NO:1, or a contiguous fragment of 3309-3348 of SEQ ID NO:1, or any complement thereof.

A polynucleotide fragment, as used herein, unless explicitly specified otherwise, refers to a sequence comprising at least 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, or 3400 contiguous nucleic acids of a given polynucleotide sequence.

In some embodiments, the nucleic acid molecule of the present invention comprises a polynucleotide having a sequence that is at least about 90%, 93%, 95%, 96%, 97%, 97.5%, 98%, 98.5%, 99%, or 99.5% identical to SEQ ID NO:1, or a fragment thereof, or any complement thereof. In some embodiments, the nucleic acid molecule of the present invention comprises a polynucleotide having a sequence that is at least about 90%, 93%, 95%, 96%, 97%, 97.5%, 98%, 98.5%, 99%, or 99.5% identical to nucleic acids 1-1167 of SEQ ID NO:1, or a fragment thereof, or any complement thereof. In an embodiment, the nucleic acid molecule encoding MMG8 or an MMG8 variant comprises the SxIP motif (Ser-x-Ile-Pro).

In an embodiment, the nucleic acid sequence of the present invention is identical to that of the mature mRNA that can be translated into MMG8 or an MMG8 variant of the present invention. In another embodiment, the nucleic acid molecule of the present invention is a cDNA molecule, of which one strand is complementary to a mature mRNA that can be translated into MMG8 or an MMG8 variant of the present invention. The DNA and RNA sequences of the subject invention can be readily determined by those skilled in the art based on degeneracy of the genetic code.

In addition, one or more nucleotides of the subject invention may be substituted, deleted or inserted. Natural nucleotides of DNA can be substitute with nucleotides having a base moiety including, but not limited to, inosine, 5-fluorouracil, 5-bromouracil, hypoxanthine, 1-methylguanine, 5-methylcytosine, and tritylated bases. The sugar moiety of the nucleotide in a sequence can also be modified, and such modification includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Further, the present invention provides nucleic acids, oligonucleotides, antisense oligonucleotides, and synthetic oligonucleotides that hybridize to the nucleic acid encoding MMG8 or an MMG8 variant, useful as agents to detect the presence or level of MMG8 nucleic acid molecules in the biological samples. The present invention contemplates the use of nucleic acid sequences corresponding to the coding sequence of MMG8 or MMG8 variants of the invention, and to the complementary sequence thereof.

In an embodiment, such a nucleic acid molecule can be used as an oligonucleotide or polynucleotide probe. The preferred oligonucleotides for detecting the presence or level of the MMG8 nucleic acid molecule in biological samples are those that are complementary to at least part of the cDNA sequence encoding the MMG8 or an MMG8 variant of the present invention. These complementary sequences are also known in the art as "antisense" sequences. These oligonucleotides may be oligoribonucleotides or oligodeoxyribonucleotides. In addition, oligonucleotides may be natural oligomers composed of the biologically significant nucleotides, i.e., A (adenine), dA (deoxyadenine), G (guanine), dG (deoxyguanine), C (cytosine), dC (deoxycytosine), T (thymine) and U (uracil), or modified oligonucleotide species, substituting, for example, a methyl group or a sulfur atom for a phosphate oxygen in the inter-nucleotide phosophodiester linkage.

The nucleic acid molecules of the present invention may be isolated from cells of interest (e.g. tissue cells of an organism or tissue-derived cell lines) or artificially created (e.g. recombinant DNA and chemically-synthesized polynucleotide molecules). For example, the oligonucleotides can be prepared by using any of the commercially available, automated nucleic acid synthesizers. Alternatively, the oligonucleotides may be created by standard recombinant DNA techniques, for example, inducing transcription of the noncoding strand. The DNA sequence encoding MMG8 or MMG8 variants may be inverted in a recombinant DNA system, e.g., inserted in reverse orientation downstream of a suitable promoter, such that the noncoding strand now is transcribed.

Although any length oligonucleotide may be utilized to hybridize to a nucleic acid encoding MMG8 or an MMG8 variant, oligonucleotides typically within the range of 8-200, 15-100, or 15-50 nucleotides are preferred.

"Hybridization" refers to a reaction in which one or more polynucleotides react to form a complex that is stabilized via hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. Various degrees of stringency of hybridization can be employed. The more severe the conditions, the greater the complementarity that is required for duplex formation. Severity of conditions can be controlled by temperature, probe concentration, probe length, ionic strength, time, and the like.

Preferably, hybridization is conducted under high stringency conditions by techniques well known in the art, as described, for example, in Keller, G. H. & M. M. Manak, *DNA*

*Probes*, and the companion volume *DNA Probes: Background, Applications, Procedures* (various editions, including $2^{nd}$ Edition, Nature Publishing Group, 1993). Hybridization is also described extensively in the Molecular Cloning manuals published by Cold Spring Harbor Laboratory Press, including Sambrook & Russell, *Molecular Cloning: A Laboratory Manual* (2001).

An example of high stringency conditions for hybridization is at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C. A non-limiting example of hybridization conditions are conditions selected to be about 1, 2, 3, 4, 5, 6, 7, 8, 9, 10, 11, 12, 13, 14, 15, 16, 17, 18, 19, 20, 21, 22, 23, 24, or 25° C. lower than the thermal melting point ($T_m$) for the specific sequence in the particular solution. $T_m$ is the temperature (dependent upon ionic strength and pH) at which 50% of the target sequence hybridizes to a perfectly matched probe. $T_m$ typically increases with $[Na^+]$ concentration because the sodium cations electrostatically shield the anionic phosphate groups of the nucleotides and minimize their repulsion. The washes employed may be for about 5, 10, 15, 20, 25, 30, or more minutes each, and may be of increasing stringency if desired.

Calculations for estimating $T_m$ are well-known in the art. For example, the melting temperature may be described by the following formula (Beltz, G. A., K. A. Jacobs, T. H. Eickbush, P. T. Cherbas, and F. C. Kafatos, *Methods of Enzymology*, R. Wu, L. Grossman and K. Moldave [eds.] Academic Press, New York 100:266-285, 1983).

$$Tm=81.5°\ C.+16.6\ \text{Log}\ [Na^+]+0.41(\%\ G+C)-0.61(\%\ \text{formamide})-600/\text{length of duplex in base pairs.}$$

A more accurate estimation of $T_m$ may be obtained using nearest-neighbor models. Breslauer, et al., *Proc. Natl. Acad. Sci. USA,* 83:3746-3750 (1986); SantaLucia, *Proc. Natl. Acad. Sci. USA,* 95: 1460-1465 (1998); Allawi & SantaLucia, *Biochemistry* 36:10581-94 (1997); Sugimoto et al., *Nucleic Acids Res.,* 24:4501-4505 (1996). $T_m$ may also be routinely measured by differential scanning calorimetry (Duguid et al., *Biophys J,* 71:3350-60, 1996) in a chosen solution, or by other methods known in the art, such as UV-monitored melting. As the stringency of the hydridization conditions is increased, higher degrees of homology are obtained.

The oligonucleotide selected for hybridizing to the MMG8 nucleic acid molecule, whether synthesized chemically or by recombinant DNA technology, can be isolated and purified using standard techniques and then preferably labeled (e.g., with $^{35}S$ or $^{32}P$) using standard labeling protocols.

The present invention also contemplates the use of oligonucleotide pairs in polymerase chain reactions (PCR) to detect the expression of MMG8 or MMG8 variants in biological samples. The oligonucleotide pairs include a forward MMG8 primer and a reverse MMG8 primer.

The presence of MMG8 or MMG8 variants in a sample from a patient may be determined by nucleic acid hybridization, such as but not limited to Northern blot analysis, dot blotting, Southern blot analysis, fluorescence in situ hybridization (FISH), and PCR. Chromatography, preferably HPLC, and other known assays may also be used to determine messenger RNA levels of MMG8 or MMG8 variants in a sample.

In one embodiment, the present invention contemplates the use of nucleic acids as agents for detecting MMG8 or an MMG8 variant in biological samples of patients, wherein the nucleic acids are labeled. The nucleic agents may be labeled with a radioactive label, a fluorescent label, an enzyme, a chemiluminescent tag, a colorimetric tag, or other labels or tags that are discussed above or that are known in the art.

In certain embodiment, the methods of detecting MMG8 nucleic acid in biological samples include Northern blot analysis, dot blotting, Southern blot analysis, FISH, and PCR.

In one embodiment, the present invention contemplates the use of Northern blot analysis to detect the presence of MMG8 mRNA in a sample of bodily fluid. The first step of the analysis involves separating a sample containing MMG8 nucleic acid by gel electrophoresis. The dispersed nucleic acids are then transferred to a nitrocellulose filter or another filter. Subsequently, the labeled oligonucleotide is exposed to the filter under suitable hybridizing conditions, e.g., 50% formamide, 5×SSPE, 2×Denhardt's solution, 0.1% SDS at 42° C., as described in Molecular Cloning: A Laboratory Manual, Maniatis et al. (1982, CSH Laboratory). Other useful procedures known in the art include solution hybridization, dot and slot RNA hybridization, and probe based microarrays. Measuring the radioactivity of hybridized fragments, using standard procedures known in the art quantitates the amount of MMG8 nucleic acid present in the biological fluid of a subject.

Dot blotting involves applying samples containing the nucleic acid of interest to a membrane. The nucleic acid can be denatured before or after application to the membrane. The membrane is incubated with a labeled probe. Dot blot procedures are well known to the skilled artisan and are described more fully in U.S. Pat. Nos. 4,582,789 and 4,617,261, the disclosures of which are incorporated herein by reference.

Polymerase chain reaction (PCR) is a process for amplifying one or more specific nucleic acid sequences present in a nucleic acid sample using primers and agents for polymerization and then detecting the amplified sequence. A specific example of PCR that is routinely performed by the skilled artisan to detect desired sequences is reverse transcript PCR (RT-PCR; Saiki et al., *Science,* 1985, 230:1350; Scharf et al., *Science,* 1986, 233:1076). RT-PCR involves isolating total RNA from biological fluid, denaturing the RNA in the presence of primers that recognize the desired nucleic acid sequence, using the primers to generate a cDNA copy of the RNA by reverse transcription, amplifying the cDNA by PCR using specific primers, and detecting the amplified cDNA by electrophoresis or other methods known to the skilled artisan.

Vectors, Expression Constructs and Host Cells

In another aspect, the present invention provides vectors, expression constructs, and host cells comprising a nucleic acid molecule of the present invention. In an embodiment, the vector, expression construct, or host cell of the present invention comprises a nucleic acid molecule comprising SEQ ID NO:1, or a fragment thereof, or any complement thereof.

In an embodiment, the vector, expression construct, or host cell of the present invention comprises a nucleic acid molecule, wherein the nucleic acid molecule comprises nucleic acids 1-1167 of SEQ ID NO:1, or a complement thereof. In some embodiments, the vector, expression construct, or host cell of the present invention comprises a nucleic acid molecule, wherein the nucleic acid molecule comprises a polynucleotide comprising nucleic acids 1-1167 of SEQ ID NO:1, wherein the 3' end of the polynucleotide sequence comprises 3292-3348 of SEQ ID NO:1, or a contiguous fragment of nucleic acids 3292-3348 of SEQ ID NO:1, or any complement thereof.

In some embodiments, the vector, expression construct, or host cell of the present invention comprises a nucleic acid molecule, wherein the nucleic acid molecule comprises a polynucleotide comprising nucleic acids 1-1167 of SEQ ID NO:1, wherein the 3' end of the polynucleotide sequence comprises 3292-3348 of SEQ ID NO:1, or a contiguous fragment having at least 75%, 80%, 85%, 90%, 95%, or 99% identity to nucleic acids 3292-3348 of SEQ ID NO:1, or any complement thereof.

In some embodiments, the vector, expression construct, or host cell of the present invention comprises a polynucleotide having a sequence that is at least about 90%, 93%, 95%, 96%, 97%, 97.5%, 98%, 98.5%, 99%, or 99.5% identical to SEQ ID NO:1, or a fragment thereof, or any complement thereof.

As used herein, the term "expression construct" refers to a combination of nucleic acid sequences that provides for transcription of an operably linked nucleic acid sequence. As used herein, the term "operably linked" refers to a juxtaposition of the components described, wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment.

Chemical enhancers are cis-acting elements that increase gene transcription and can also be included in the expression construct. Chemical enhancer elements are known in the art, and include, but are not limited to, the CaMV 35S enhancer element, cytomegalovirus (CMV) early promoter enhancer element, and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Host cells of the present invention include, for example, bacteria host cells, yeast host cells, plant host cells, insect host cells, mammalian host cells, and preferably human host cells. Host cells that can be used in the present invention include, but are not limited to, CHO cells, HEK-293 cells, 293T cells, COS cells, COS-7 cells, and NIH 3T3 cells.

MMG8 Antibodies and Aptamers

Another aspect of the present invention provides antibodies and aptamers that bind specifically to MMG8 or MMG8 variants of the present invention. In an embodiment, antibodies and aptamers of the subject invention bind specifically to the MMG8 isoform comprising SEQ ID NO:2. In certain embodiments, the antibodies and aptamers of the present invention bind specifically to an epitope at the carboxy-terminus of MMG8 of SEQ ID NO:2.

In certain embodiments, the antibodies and aptamers of the present invention bind specifically to an epitope comprising 926-1116 of SEQ ID NO:2, or an epitope comprising a fragment comprising 1, 2, 3, 4, 5, 6, 7, 8, 9, 10, 11, 12, 13, 14, 15, 16, 17, or 18 contiguous amino acids of 1098-1116 of SEQ ID NO:2.

In certain embodiments, the antibodies and aptamers of the present invention bind specifically to an epitope comprising 926-1116 of SEQ ID NO:2, or an epitope comprising a fragment of 926-1116 of SEQ ID NO:2, wherein the fragment has at least 75%, 80%, 90%, or 95% identity to 926-1116 of SEQ ID NO:2.

In certain embodiments, the antibodies and aptamers of the present invention bind specifically to an epitope comprising 926-1116 of SEQ ID NO:2, or an epitope comprising a fragment of 1098-1116 of SEQ ID NO:2, wherein the fragment has at least 75%, 80%, 90%, or 95% identity to 1098-1116 of SEQ ID NO:2.

In certain embodiments, the antibodies and aptamers of the present invention bind specifically to an epitope comprising 926-1116 of SEQ ID NO:2, or an epitope comprising a fragment of 1103-1116 of SEQ ID NO:2, wherein the fragment has at least 75%, 80%, 90%, or 95% identity to 1103-1116 of SEQ ID NO:2.

In a preferred embodiment, the anti-MMG8 antibody of the present invention is a humanized antibody.

In some embodiments, the antibodies and aptamers of the present invention do not bind to an epitope comprising amino acids 1-389 of SEQ ID NO:2, or an epitope comprising any fragment thereof. In some embodiments, the antibodies of the present invention do not bind to any one or more SEQ ID NOs: 3-18.

"Specific binding" or "specificity" refers to the ability of a protein to detectably bind an epitope presented on a protein or polypeptide molecule of interest, while having relatively little detectable reactivity with other proteins or structures. Specificity can be relatively determined by binding or competitive binding assays, using, e.g., Biacore instruments. Specificity can be exhibited by, e.g., an about 10:1, about 20:1, about 50:1, about 100:1, 10.000:1 or greater ratio of affinity/avidity in binding to the specific target molecule versus nonspecific binding to other irrelevant molecules.

"Selectivity" refers to the preferential binding of a protein to a particular region, target, or peptide as opposed to one or more other biological molecules, structures, cells, tissues, etc. For example, selectivity can be determined by competitive ELISA or Biacore assays. The difference in affinity/avidity that marks selectivity can be any detectable preference (e.g., a ratio of more than 1:1.1, or more than about 1:5, if detectable).

Antibodies of the subject invention can be in any of a variety of forms, including intact immunoglobulin molecules, fragments of immunoglobulin molecules such as Fv, Fab and similar fragments; multimers of immunoglobulin molecules (e.g., diabodies, triabodies, and bi-specific and tri-specific antibodies, as are known in the art; see, e.g., Hudson and Kortt, J. Immunol. Methods 231:177 189, 1999); fusion constructs containing an antibody or antibody fragment; and human or humanized immunoglobulin molecules or fragments thereof.

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Antibodies of the subject invention include polyclonal and monoclonal antibodies. The term “monoclonal antibody,” as used herein, refers to an antibody or antibody fragment obtained from a substantially homogeneous population of antibodies or antibody fragments (i.e. the individual antibodies within the population are identical except for possible naturally occurring mutations that may be present in a small subset of the antibody molecules).

Anti-MMG8 antibodies of the present invention can be prepared using isolated native MMG8 or recombinant MMG8. Preferably, antibodies used in the methods of the invention are reactive against MMG8 if they bind with a $K_a$ of greater than or equal to $10^7$ M. In a sandwich immunoassay of the invention, mouse polyclonal antibodies and rabbit polyclonal antibodies are utilized.

For use in detection of MMG8 or an MMG8 variant from biological sample, the purified antibodies can be covalently attached, either directly or via linker, to a compound which serves as a reporter group to permit detection of the presence of MMG8 or an MMG8 variant. A variety of different types of substances can serve as the reporter group including, but not limited to, enzymes, dyes, radioactive metal and non-metal isotopes, fluorogenic compounds, fluorescent compounds, etc. Methods for preparation of antibody conjugates of the antibodies (or fragments thereof) of the invention are described in U.S. Pat. Nos. 4,671,958; 4,741,900 and 4,867,973.

Assays for Detecting MMG8 Isoforms

Another aspect of the present invention provides assays for detecting the presence or level of MMG8 or an MMG8 variant in a sample. MMG8 proteins or MMG8 transcripts can be used to determine the level of MMG8 or an MMG8 variant in a sample. In an embodiment, the sample is a biological sample obtained from a subject.

In one embodiment, the method for detecting the presence or level of MMG8 or an MMG8 variant comprises:

(a) contacting a sample with an agent that binds to MMG8 or an MMG8 variant; and (b) detecting the binding of the agent to the MMG8 or an MMG8 variant.

Agents capable of binding to MMG8 or an MMG8 variant in the samples encompass those that interact or bind with the MMG8 polypeptide or the nucleic acid molecule encoding MMG8. Examples of such agents (also referred to herein as binding agents) include, but are not limited to, MMG8 antibodies or fragments thereof that bind specifically to MMG8, MMG8 binding partners, aptamers, and nucleic acid molecules that hybridize to the nucleic acid molecules encoding MMG8 polypeptides. Preferably, the binding agent is labeled with a detectable substance (e.g., a detectable moiety). The binding agent may itself function as a label.

In a specific embodiment, the agent that detects MMG8 or an MMG8 variant is an antibody that binds specifically to MMG8 or the MMG8 variant. In a specific embodiment, the anti-MMG8 antibody binds specifically to an epitope at the carboxy-terminus of MMG8 of SEQ ID NO:2.

In certain embodiments, the antibody or aptamer of the present invention binds specifically to an epitope comprising amino acids 926-1116 of SEQ ID NO:2, or an epitope comprising a fragment of 1, 2, 3, 4, 5, 6, 7, 8, 9, 10, 11, 12, 13, 14, 15, 16, 17, or 18 contiguous amino acids of 1098-1116 of SEQ ID NO:2.

In certain embodiments, the antibody or aptamer of the present invention binds specifically to an epitope comprising amino acids 926-1116 of SEQ ID NO:2, or an epitope comprising a fragment having at least 75%, 80%, 85%, 90%, or 95% identity to 926-1116 of SEQ ID NO:2.

In one embodiment, the agent (such as an anti-MMG8 antibody) that binds to the MMG8 or an MMG8 variant is labeled with a detectable substance. In a specific embodiment, the agent is fluorescently labeled. In one embodiment, the level of MMG8 or an MMG8 variant is determined by measuring the fluorescence level of the binding complex.

In a preferred embodiment, the invention provides a method for detecting the presence or level of MMG8 or an MMG8 variant, comprising:

(a) incubating a sample with a first antibody specific for MMG8 or an MMG8 variant wherein the first antibody is directly or indirectly labeled with a detectable substance, and a second antibody specific for MMG8 or the MMG8 variant wherein the second antibody is immobilized;

(b) separating the first antibody from the second antibody to provide a first antibody phase and a second antibody phase; and (c) detecting the detectable substance in the first or second antibody phase thereby quantitating MMG8 or the MMG8 variant in the sample.

In an embodiment, MMG8 or MMG8 variants can be detected by incubating a sample with a first antibody or a first aptamer and a second antibody or a second aptamer. In an embodiment, the first antibody or the first aptamer binds specifically to an epitope comprising amino acids 926-1116 of SEQ ID NO:2. In an embodiment, the first antibody or the first aptamer binds to an epitope comprising a fragment having at least 75%, 80%, 85%, 90%, or 95% identity to 926-1116 of SEQ ID NO:2. In an embodiment, the second antibody or the second aptamer that binds specifically to an epitope comprising a fragment comprising 50, 45, 40, 35, 30, 25, 20, 15, 14, 13, 12, 11, 10, 9, 8, 7, 6, or 5 amino acids of SEQ ID NO:2. In an embodiment, the second antibody or the second aptamer that binds specifically to an epitope having at least 75%, 80%, 85%, 90%, or 95% identity to a fragment comprising 50, 45, 40, 35, 30, 25, 20, 15, 14, 13, 12, 11, 10, 9, 8, 7, 6, or 5 amino acids of SEQ ID NO:2.

In another embodiment, the present invention provides a method for detecting the presence of a nucleic acid molecule encoding MMG8 or an MMG8 variant in a sample, comprising:

(a) contacting the sample with an agent that selectively binds to the nucleic acid molecule; and (b) detecting whether the agent binds to the nucleic acid molecule in the sample.

In a specific embodiment, the binding agent is a second nucleic acid molecule comprising at least 8 nucleic acids of SEQ ID NO:1, or a complement thereof. In a specific embodiment, the binding agent is a second nucleic acid molecule comprising 3294-3348 of SEQ ID NO:1, or a fragment of 3294-3351 of SEQ ID NO:1, or any complement thereof.

The terms "detecting" or "detect" include assaying or otherwise establishing the presence or absence of the target MMG8 or MMG8 variant (nucleic acids encoding MMG8 or an MMG8 variant), subunits thereof, or combinations of agent bound targets, and the like. The term encompasses quantitative, semi-quantitative, and qualitative detection methodologies.

Methods for detecting MMG8 and other biomarkers (e.g. protein or peptide and nucleic acids) of the subject invention are well known in the art, including but not limited to, Western blots, Northern blots, Southern blots, ELISA, PCR, immunoprecipitation, immunofluorescence, radioimmunoassay, flow cytometry, immunocytochemistry, nucleic acid hybridization techniques, nucleic acid reverse transcription methods, and nucleic acid amplification methods.

Preferably, in the various embodiments of the invention, the detection method provides an output (i.e., readout or signal) with information concerning the presence, absence, or amount of MMG8 in a sample from a subject. For example, the output may be qualitative (e.g., "positive" or "negative"), or quantitative (e.g., a concentration such as nanograms per milliliter).

The terms "sample", "biological sample", and the like refer to a type of material known to or suspected of expressing or containing MMG8 or an MMG8 variant. The sample can be derived from any biological source, such as tissues or extracts, including cells (e.g., tumor cells) and physiological fluids, such as, for example, whole blood, plasma, serum, peritoneal fluid, ascites, and the like. The sample can be obtained from animals, preferably mammals, most preferably humans. The sample can be pretreated by any method and/or can be prepared in any convenient medium that does not interfere with the assay. The sample can be treated prior to use, such as preparing plasma from blood, diluting viscous fluids, applying one or more protease inhibitors to samples. Sample treatment can involve filtration, distillation, extraction, concentration, inactivation of interfering components, the addition of reagents, and the like.

Drug Screening Assays

Another aspect of the present invention pertains to use of the MMG8 or an MMG8 variant for screening for therapeutic agents that can be used for treating diseases including, but not limited to, diseases involving defects in microtubule organization and/or nucleation; diseases associated with defects in protein modification, secretion, and trafficking; and diseases involving abnormal cell proliferation. In a specific embodiment, the MMG8 or MMG8 variants of the present invention can be used to screen for anti-cancer therapeutics. The therapeutic agent can be a drug, chemical, compound, protein or peptide, or a nucleic acid molecule (e.g. DNA, RNA such as siRNA).

In one embodiment, the subject methods can be used for screening for therapeutic agents that reduce levels of MMG8 or MMG8 transcripts (such as primary, intermediate, and mature mRNA transcripts of MMG8) in cells. In addition, the subject methods can be used for screening for therapeutic agents that inhibit or reduce MMG8 expression levels.

In one embodiment, the present invention provides a method for screening for therapeutics that inhibits MMG8 or an MMG8 variant, wherein the method comprises:

a) providing a test sample containing cells expressing MMG8 or the MMG8 variant;

b) contacting a candidate agent with the test sample;

c) determining a level of MMG8 or the MMG8 variant in the test sample; and d) selecting the candidate agent if said agent reduces the level of MMG8 or the MMG8 variant in the test sample.

The level of MMG8 or an MMG8 variant can be determined by measuring the levels of MMG8 proteins and/or MMG8 transcripts.

In one embodiment, the methods can be used for screening for therapeutic agents that modulate the activity of MMG8 or MMG8 variants of the invention. In certain embodiments, the present invention provides methods for screening for therapeutic agents that modulate, enhance, or inhibit the association between MMG8 or MMG8 variants with proteins selected from AKAP450, EB1, EB3 and γ-tubulin complexes such as GCP2 and GCP3. In certain embodiments, the present invention can be used for screening for therapeutic agents that modulate cellular activities including, but not limited to, microtubule organization; microtubule nucleation; post-translational protein modification, secretion and transport; and cell division, proliferation and migration.

In an embodiment, the present invention provides a method for selecting an agent that modulates the activity of MMG8 or an MMG8 variant, comprising:

a) providing a first test sample containing cells expressing MMG8 or the MMG8 variant;

b) contacting the first test sample with a protein that interacts with MMG8 or the MMG8 variant;

c) determining a first level of the binding of MMG8 or the MMG8 variant to said protein that interacts with MMG8 or the MMG8 variant in the first test sample;

d) providing a second test sample containing cells expressing MMG8 or the MMG8 variant;

e) contacting the second sample with a candidate agent;

f) after step e), contacting the second test sample with said protein that interacts with MMG8 or the MMG8 variant;

g) determining a second level of the binding of MMG8 or the MMG8 variant to said protein that interacts with MMG8 or the MMG8 variant in the second test sample; and h) selecting the candidate agent as a modulator of MMG8 or the MMG8 variant, if said second level is different from said first level.

In an embodiment, the protein that interacts with MMG8 or MMG8 variants is selected from AKAP450, EB1, EB3, GCP2, or GCP3. In an embodiment, the candidate agent is selected as an MMG8 modulator, if the difference between the first level and the second level is more than 10%, 15%, 20%, 25%, 30%, 40%, 50%, 60% m 70%, 80%, 90%, or 100%. In an embodiment, if said second level is lower than said first level, the selected agent is an MMG8 inhibitor. In an embodiment, if said second level is higher than said first level, the selected agent is an MMG8 inhibitor.

Agents that modulate the level and/or activity of MMG8 or MMG8 variants of the invention can be used for treatment of diseases including, but not limited to, diseases involving defects in microtubule organization and/or nucleation; diseases associated with defects in protein modification, secretion, and trafficking; and diseases involving abnormal cell proliferation. In a specific embodiment, agents that modulate MMG8 level or activity can be used to treat diseases including, but not limited to, neuronal diseases, diabetes, cystic fibrosis, and lysosomal storage diseases (such as diseases involving LAMP-1).

In another specific embodiment, agents that modulate MMG8 level or activity can be used to treat or retard cancer cell division, proliferation, and/or migration. The MMG8- modulators can be used to treat cancer including, but not limited to, brain carcinoma, skin cancer, stomach cancer, and breast cancer.

In a further embodiment, the present invention provides a method for screening for anti-cancer agents, wherein the method comprises:

a) providing a test sample containing tumor cells expressing MMG8 or an MMG8 variant;

b) contacting a candidate agent with the test sample;

c) determining a level of tumor cell population in a test sample;

d) comparing said level in the test sample with that of a control sample; and e) selecting the candidate agent if said level in the test sample is lower than that of the control sample.

In an embodiment, the candidate agent is selected as an anti-cancer agent, if the level of tumor cell population in the test sample is more than 10%, 15%, 20%, 25%, 30%, 40%, 50%, 60%, 70%, 80%, 90%, or 100% lower than that of the control sample.

Treatment of Diseases Associated with MMG8

In another aspect, the present invention provides prevention or treatment of diseases associated with defects in MMG8. In one embodiment, the present invention can be used to treat diseases including, but not limited to, neuronal diseases, diabetes, cystic fibrosis, lysosomal storage diseases, and cancer.

In one embodiment, the present invention provides a method for treating a disease associated with abnormally increased level of MMG8 or an MMG8 variant, comprising: inhibiting or reducing the expression of MMG8 or the MMG8 variant in a subject.

In a specific embodiment, the present invention provides a method for treating a disease associated with abnormally increased level of MMG8, comprising administering, to a subject in need of such treatment, an effective amount of an si-RNA that inhibits the expression of MMG8 or MMG8 variants in the subject. In another specific embodiment, the level or activity of MMG8 or MMG8 variants can be reduced or inhibited by administering, to a subject in need of such treatment, an effective amount of an anti-MMG8 antibody that binds specifically to MMG8 or an MMG8 variant. Diseases associated with abnormally increased level of MMG8 include, for example, cancer such as brain carcinoma, skin cancer, stomach cancer, and breast cancer. Specifically, the present invention can be used to inhibit tumor metastasis.

In another embodiment, the present invention provides a method for treating a disease associated with abnormally reduced level of MMG8, comprising: increasing the expression MMG8 or an MMG8 variant.

In a specific embodiment, the present invention provides a method for treating a disease associated with abnormally reduced level of MMG8, comprising administering, to a subject in need of such treatment, an effective amount of an MMG8 protein or a fragment thereof, a nucleic acid molecule encoding the MMG8 protein or a fragment thereof, or a vector or host cell comprising said nucleic acid molecule. Diseases associated with abnormally decreased MMG8 level include lysosomal storage diseases.

In another aspect, the present invention provides a method for modulating a cellular activity, comprising modulating the level or activity of MMG8 in a subject. Cellular activities that can be modulated in accordance with the present invention include, but are not limited to, microtubule growth, organization, and/or nucleation at the Golgi apparatus; the stability of AKAP450; the localization of γTuCs to the Golgi apparatus; and post-translation modification (such as glycosylation), transport, and secretion of proteins.

In one embodiment, the present invention provides a method of inhibiting ER-to-Golgi transport of LAMP-1, by inhibiting the expression or activity of myomegalin, wherein the method comprises administering, to cells in which said inhibition is desired, an effective amount of an siRNA that inhibits the expression of the myomegalin isoform of the present invention, or an antibody or aptamer that binds specifically to the myomegalin isoform of present invention. In a specific embodiment, the method can be used to treat LAMP-1-related lysosomal storage diseases.

In another embodiment, the present invention provides a method of reducing the level of glycosylated CD44 having a molecular weight of about 90 kDa, comprising administering to cells in which said reduction is desired, an effective amount of an siRNA that inhibits the expression of the myomegalin isoform of the present invention, or an antibody or aptamer that binds specifically to the myomegalin isoform of the present invention.

In another embodiment, the present invention provides a method of increasing the level of glycosylated CD44 having a molecular weight of about 90 kDa, comprising administering to cells in which said increase is desired, an effective amount of the myomegalin isoform of the present invention, or a nucleic acid molecule encoding the myomegalin isoform of the present invention.

The term "subject," as used herein, describes an organism, including mammals such as primates. Mammalian species that can benefit from the subject methods include, but are not limited to, apes, chimpanzees, orangutans, humans, monkeys; and domesticated and/or laboratory animals such as dogs, cats, horses, cattle, pigs, sheep, goats, chickens, mice, rats, guinea pigs, and hamsters. Typically, the subject is a human.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "prevention" or any grammatical variation thereof (e.g., prevent, preventing, and prevention etc.), as used herein, includes but is not limited to, delaying the onset of symptoms, preventing relapse to a disease, increasing latency between symptomatic episodes, or a combination thereof. Prevention, as used herein, does not require the complete absence of symptoms.

"A subject in need of such treatment", as used herein, includes a subject who is specifically at risk of, has symptoms of, or is diagnosed with, a diseases associated with MMG8 or an MMG isoform. In a specific embodiment, the present invention comprises diagnosing whether a subject has a disease associated with MMG8, wherein the therapeutic agents and compositions of the present invention are administered to the subject who is diagnosed with such disease.

The term "effective amount," as used herein, refers to an amount that is capable of preventing, ameliorating, or treating a disease. In certain embodiments, the effective amount enables at least 5%, 10%, 15%, 20%, 25%, 30%, 35%, 40%, 45%, 50%, 60%, 70%, 80%, 90%, or 100% modulation of the level and/or activity of MMG8.

Therapeutic Compositions and Formulations

The subject invention further provides therapeutic compositions that contain a therapeutically effective amount of the therapeutic agents and compositions and a pharmaceutically acceptable carrier or adjuvant.

The terms “pharmaceutically acceptable,” “physiologically tolerable,” and grammatical variations thereof, as used herein, include compositions, carriers, diluents, and reagents, are used interchangeably, and represent that the materials are capable of administration to or upon a subject such as mammal.

The term “carrier” refers to an adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin.

Suitable carriers also include ethanol, dimethyl sulfoxide, glycerol, silica, alumina, starch, sorbitol, inosital, xylitol, D-xylose, mannitol, powdered cellulose, microcrystalline cellulose, talc, colloidal silicon dioxide, calcium carbonate, calcium phosphate, calcium aluminium silicate, aluminium hydroxide, sodium starch phosphate, lecithin, and equivalent carriers and diluents. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents.

The amount of active ingredient that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

The therapeutic agents and compositions of the subject invention can be formulated according to known methods for preparing pharmaceutically useful compositions. Formulations are described in detail in a number of sources which are well known and readily available to those skilled in the art. For example, Remington’s Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

The therapeutic or pharmaceutical compositions of the subject invention can also be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use also can be prepared. The preparation also can be emulsified, such as oil-in-water emulsion.

The invention also provides a pharmaceutical pack or kit comprising one or more containers filled with one or more of the ingredients, e.g., compound, carrier suitable for administration.

Routes of Administration

The therapeutic agents and compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural, and intrasternal injection, infusion, and electroporation, as well as co-administration as a component of any medical device or object to be inserted (temporarily or permanently) into a subject.

The amount of the therapeutic agent or pharmaceutical composition of the subject invention which is effective in the treatment of a disease will depend on the nature of the disease, condition or disorder and can be determined by standard clinical techniques. In general, the dosage ranges from about 0.01 to about 2000 mg, about 0.01 to about 1000 mg, about 0.01 to about 500 mg, about 0.01 to about 300 mg, about 0.01 to about 200 mg, or about 0.01 to about 100 mg. Such a unit dose may be administered once to several times (e.g. two, three and four times) every two weeks, every week, twice a week, or every day, according to the judgment of the practitioner and each patient’s circumstances.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg and preferably about 1 to 100 mg/kg; intranasal instillation, 0.01 to about 20 mg/kg; and aerosol, 0.01 to about 20 mg/kg of animal (body) weight.

Once improvement of the patient’s condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient’s circumstances. Effective doses may be extrapolated from dose-response curves derived from in vitro or animal model test systems.

Diagnosis of Diseases Associated with MMG8

Another aspect of the present invention pertains to methods for diagnosis of a disease associated with an abnormal level of MMG8 or an MMG8 variant of the invention. In an embodiment, the method comprises:

a) obtaining a biological sample from a subject;

b) measuring a level of MMG8 or an MMG8 variant in the biological sample; and c) characterizing the subject’s level of MMG8 or the MMG8 variant.

In a specific embodiment, the MMG8 protein biomarker comprises SEQ ID NO:2.

Detection of MMG8-associated diseases can be based on characterizing the level of MMG8 or an MMG8 variant in a sample with a predetermined level of the biomarker in a normal population sample and correlating such levels with factors such as the incidence, severity, and/or frequency of developing the specific disease in a population. In addition, the predetermined value can be a single value, multiple values, a single range, or multiple ranges. Thus, diagnosis may be based on determining in which of the predetermined reference values or ranges the subject's level falls.

The MMG8 level can be determined based on the levels of MMG8 proteins or MMG8 transcripts. In a specifically exemplified embodiment, the MMG8 biomarker can be used for diagnosis of lysosomal storage diseases.

Devices

The methods of the invention can be carried out on a solid support. The solid supports used may be those which are conventional for the purpose of assaying an analyte in a biological sample, and are typically constructed of materials such as cellulose, polysaccharide such as Sephadex, and the like, and may be partially surrounded by a housing for protection and/or handling of the solid support. The solid support can be rigid, semi-rigid, flexible, elastic (having shape-memory), etc., depending upon the desired application. MMG8 can be detected in a sample in vivo or in vitro (ex vivo). When, according to an embodiment of the invention, the amount of MMG8 in a sample is to be determined without removing the sample from the body (i.e., in vivo), the support should be one which is harmless to the subject and may be in any form convenient for insertion into an appropriate part of the body. For example, the support may be a probe made of polytetrafluoroethylene, polystyrene or other rigid non-harmful plastic material and having a size and shape to enable it to be introduced into a subject. The selection of an appropriate inert support is within the competence of those skilled in the art, as are its dimensions for the intended purpose.

A contacting step in the assay (method) of the invention can involve contacting, combining, or mixing the biological sample and the solid support, such as a reaction vessel, microvessel, tube, microtube, well, multi-well plate, or other solid support. In an embodiment of the invention, the solid support to be contacted with the biological sample has an absorbent pad or membrane for lateral flow of the liquid medium to be assayed, such as those available from Millipore Corp. (Bedford, Mass.), including but not limited to Hi-Flow Plus™ membranes and membrane cards, and SureWick™ pad materials.

Immunochromatographic assays, also known as lateral flow test strips or simply strip tests, for detecting various analytes of interest, have been known for some time, and may be used for detection of MMG8. The benefits of lateral flow tests include a user-friendly format, rapid results, long-term stability over a wide range of climates, and relatively low cost to manufacture. These features make lateral flow tests ideal for applications involving home testing, rapid point of care testing, and testing in the field for various analytes. The principle behind the test is straightforward. Essentially, any ligand that can be bound to a visually detectable solid support, such as dyed microspheres, can be tested for, qualitatively, and in many cases even semi-quantitatively. For example, a one-step lateral flow immunostrip for the detection of free and total prostate specific antigen in serum is described in Fernandez-Sanchez et al. (J. *Immuno. Methods,* 2005, 307(1-2):1-12, which is incorporated herein by reference) and may be adapted for detection of MMG8 in a biological sample.

Samples and/or MMG8-specific binding agents may be arrayed on the solid support, or multiple supports can be utilized, for multiplex detection or analysis. "Arraying" refers to the act of organizing or arranging members of a library (e.g., an array of different samples or an array of devices that target the same target molecules or different target molecules), or other collection, into a logical or physical array. Thus, an "array" refers to a physical or logical arrangement of, e.g., biological samples. A physical array can be any "spatial format" or physically gridded format" in which physical manifestations of corresponding library members are arranged in an ordered manner, lending itself to combinatorial screening. For example, samples corresponding to individual or pooled members of a sample library can be arranged in a series of numbered rows and columns, e.g., on a multi-well plate. Similarly, binding agents can be plated or otherwise deposited in microtitered, e.g., 96-well, 384-well, or -1536 well, plates (or trays). Optionally, MMG8-specific binding agents may be immobilized on the solid support.

Detection of MMG8 and other biomarkers, and other assays that are to be carried out on samples, can be carried out simultaneously or sequentially with the detection of other target molecules, and may be carried out in an automated fashion, in a high-throughput format.

The MMG8-specific binding agents can be deposited but "free" (non-immobilized) in the conjugate zone, and be immobilized in the capture zone of a solid support. The MMG8-specific binding agents may be immobilized by non-specific adsorption onto the support or by covalent bonding to the support, for example. Techniques for immobilizing binding agents on supports are known in the art and are described for example in U.S. Pat. Nos. 4,399,217, 4,381,291, 4,357,311, 4,343,312 and 4,260,678, which are incorporated herein by reference.

Kits

In another aspect, the present invention provides kits comprising the required elements for detecting the level or activity of MMG8 or an MMG8 variant, screening for therapeutic agents, and/or diagnosing or monitoring a disease associated with MMG8 or an MMG8 variant. Preferably, the kits comprise a container for collecting biological fluid from a patient and an agent for detecting the presence of MMG8 or its encoding nucleic acid in the fluid. The components of the kits can be packaged either in aqueous medium or in lyophilized form.

In a preferred embodiment, the present invention provides a protein chip comprising the MMG8 or MMG8 variants of the present invention. In a specific embodiment, the protein chip comprises the MMG8 isoform comprising SEQ ID NO:2.

The methods of the invention can be carried out using a diagnostic kit for qualitatively or quantitatively detecting MMG8 in a sample. By way of example, the kit can contain binding agents (e.g., antibodies) specific for MMG8, antibodies against the antibodies labeled with an enzyme; and a substrate for the enzyme. The kit can also contain a solid support such as microtiter multi-well plates, standards, assay diluent, wash buffer, adhesive plate covers, and/or instructions for carrying out a method of the invention using the kit. In one embodiment, the kit includes one or more protease inhibitors (e.g., a protease inhibitor cocktail) to be applied to the biological sample to be assayed.

The agent(s) can be packaged with a container for collecting the biological fluid from a patient. When the antibodies or binding partner are used in the kits in the form of conjugates in which a label is attached, such as a radioactive metal ion or a moiety, the components of such conjugates can be supplied either in fully conjugated form, in the form of intermediates or as separate moieties to be conjugated by the user of the kit.

Kits containing one or more agents that detect MMG8 nucleic acid molecules, such as but not limited to, the full length MMG8 nucleic acid, MMG8 oligonucleotides, and pairs of MMG8 primers can also be prepared. The agent(s) can be packaged with a container for collecting biological samples from a patient. The nucleic acid can be in the labeled form or to be labeled form.

Other components of the kit may include, but are not limited to, means for collecting biological samples, means for labeling the detecting agent (binding agent), membranes for immobilizing the MMG8 protein or MMG8 nucleic acid in the biological sample, means for applying the biological sample to a membrane, means for binding the agent to MMG8 in the biological sample of a subject, a second antibody, a means for isolating total RNA from a biological fluid of a subject, means for performing gel electrophoresis, means for generating cDNA from isolated total RNA, means for performing hybridization assays, and means for performing PCR, etc.

In these exemplary embodiments, the antibodies can be labeled with pairs of FRET dyes, bioluminescence resonance energy transfer (BRET) protein, fluorescent dye-quencher dye combinations, beta gal complementation assays protein fragments. The antibodies may participate in FRET, BRET, fluorescence quenching or beta-gal complementation to generate fluorescence, colorimetric or enhanced chemiluminescence (ECL) signals, for example.

These methods are routinely employed in the detection of antigen-specific antibody responses, and are well described in general immunology text books such as Immunology by Ivan Roitt, Jonathan Brostoff and David Male (London: Mosby, c1998. 5th ed. and Immunobiology: Immune System in Health and Disease/Charles A. Janeway and Paul Travers. Oxford: Blackwell Sci. Pub., 1994), the contents of which are herein incorporated by reference.

Materials and Methods

Cloning of MMG8:

Based on peptide sequences revealed by mass spectrometry, the coding sequence of MMG8 was constructed by replacing a carboxy-terminal sequence of KIAA0477 with the corresponding sequence of MMG8 amplified by RT-PCR. Mutations were introduced into MMG8 by site-directed mutagenesis.

Generation of MMG8 Antibodies:

Two MMG8 fragments, 637-925 and 926-1116, were cloned and bacterially expressed in fusion with a $His_6$-tag. The proteins were purified using $Ni^{2+}$-nitrilotriacetic acid resins (Qiagen) in the presence of 6 M urea, and were dialyzed against phosphate-buffered saline. Thereafter, rabbits were immunized with the 637-925 or 926-1116 fragment. Antisera generated against 637-925 and 926-1116 were designated as 443M and 532C, respectively. Antibodies were purified from the sera using respective antigens immobilized onto nitrocellulose membranes.

Suppression of MMG8 Expression:

Two siRNA duplexes were synthesized to target MMG8 (si-MMG8-1, AACCUCCAGUGGCUGAAAGAA (SEQ ID NO: 25); si-MMG8-2, AAGCAGAGAGACAGCUCUAUA) (SEQ ID NO: 26). The siRNAs were delivered into the cells with Lipofectamine 2000 (Invitrogen). MMG8 expression was reduced by 80-90% at 70-80 hours post-transfection.

Isolation of MMG8 and its Interacting Proteins:

To immunoprecipitate MMG8, cell extracts were prepared in RIPA buffer (25 mM Tris-HCl, pH7.4, 150 mM NaCl, 1% NP-40, 1% sodium deoxycholate, and 0.1% SDS) supplemented with the Protease Inhibitor Cocktail (Roche) and clarified. After pre-cleared with Protein A-Agarose (Invitrogen), the extracts were incubated with MMG8 antibodies bound to Protein A beads for 4 h at 4° C. with agitation. The beads were extensively washed before the immunoprecipitates were eluted for SDS-PAGE.

To prepare for mass spectrometry analysis, protein bands visualized by Coomassie Blue staining were excised and then subjected to in-gel tryptic digestion. Recovered peptides were introduced through a nanoelectrospray ion source into a quadrupole/time-of-flight mass spectrometer. Protein identity was revealed by searching a nonredundant sequence database with tandem mass spectra.

Anti-FLAG immunoprecipitation was performed using anti-FLAG-coupled beads (M2, Sigma) in cell extracts prepared with a lysis buffer (20 mM Tris-HCl, pH7.4, 150 mM NaCl, 1 mM EDTA, 1% Triton X-100, 1 mM dithiothreitol, and the Protease Inhibitor Cocktail). Immunoprecipitated proteins were detected by immunoblotting.

Immunofluorescence Microscopy:

Cell cultures were maintained in media containing 10% fetal bovine serum at 37° C. in 5% $CO_2$. HeLa, HEK293T, MCF-7, IMR-5 (human neuroblastoma cell line) and C2C12 (mouse myoblast) were grown in DMEM; human retinal pigment epithelial cells hTERT-RPE1 (RPE1) was in DMEM:Ham's F12 (1:1) (Invitrogen); human fetal lung fibroblasts MRC-5 were grown in MEM (Invitrogen). C2C12 was differentiated into myotubes in the medium of DMEM supplemented with 20% horse serum.

To perform immunostaining, cells were fixed either with cold methanol for 5 min at −20° C. or with 4% paraformaldehyde/phosphate-buffered saline for 15 min at room temperature. After staining with primary and subsequently secondary antibodies, cell images were acquired on an epifluorescence microscope (Eclipse TE2000, Nikon).

To visualize γ-tubulin and EB1 on the Golgi apparatus, cells were extracted on ice for 30 min in a saponin extraction buffer (0.1 M K-PIPES, pH6.9, 2 M glycerol, 5 mM $MgCl_2$, 2 mM EGTA, and 0.1% saponin) before methanol fixation. To enhance γ-tubulin signals, the cells were stained sequentially with two secondary antibodies, AlexaFluor dye-labeled goat secondary antibody (Invitrogen), followed by donkey anti-goat secondary antibody labeled with same dye.

Microtubule Regrowth Assays:

Cellular microtubules were completely depolymerized by placing cells on ice for 1 h or treating them with 10 mg/ml nocodazole for 2 h. To initiate microtubule regrowth, cells treated under cold conditions were transferred to a 37° C. water bath. Nocodazole-treated cells were washed several times with ice-cold phosphate-buffered saline and then incubated in medium prewarmed to 37° C. Before fixation, cells were extracted briefly with a cytoskeleton-stabilizing buffer (50 mM imidazole, pH6.8, 50 mM KCl, 0.5 mM $MgCl_2$, 0.1 mM EGTA and 0.1 mM EDTA, 4% PEG4000, and 0.1% saponin).

Microtubule Binding Assay:

To test microtubule association, HEK293T extracts were prepared in PEM buffer (100 mm PIPES, pH6.9, 1 mm EGTA, 1 mm $MgCl_2$, and 1% Triton X-100) on ice and clarified by centrifugation at 100,000g for 30 min. Microtubules were then polymerized in the extracts with 20 μM taxol and 0.5 mM GTP at 37° C. for 20 min. After polymerization, microtubules were overlaid on a cushion of 20% sucrose in the buffer for sedimentation by centrifugation (30,000g; 30 min) at 25° C. The supernatants and pellets were resolved by SDS-PAGE for immunoblotting.

Cell Proliferation Assay:

HeLa cells growing on tissue culture dishes were transfected with control or MMG8-targeting siRNA. Cells were then trypsinized at the indicated time points to count cell numbers with a hemocytometer. Data presented are from three independent assays.

EXAMPLES

Following are examples that illustrate procedures for practicing the invention. These examples should not be construed as limiting. All percentages are by weight and all solvent mixture proportions are by volume unless otherwise noted.

Example 1

Identification of MMG8

To detect MMG in proliferating cell cultures, RT-PCR was performed with oligonucleotide primers targeting the region encoding 474-762 of human MMG isoform 1. This targeted region is present in all currently-identified large MMG variants based on searches of gene databases. An oligonucleotide band was specifically amplified at the expected size from total RNA extracted from HeLa cells (FIG. 1A). The sequence of the RT-PCR product was verified. This fragment corresponds to the region encoding amino acids 474-762 of MMG isoform 1 and 637-925 of MMG8.

The RT-PCR product was also cloned into an expression vector and expressed in bacteria. The expressed protein was purified for immunizing rabbits. The resulting antibody, designated as 443M, specifically detected a human MMG protein—a single band of ~150 kDa on the immunoblots of HeLa extracts (FIG. 1B).

The MMG protein was immunoprecipitated by 443M from HeLa extracts prepared in the RIPA buffer (FIG. 1C), and excised for mass spectrometric analysis. In total, 13 peptide sequences were revealed by tandem mass spectrometry. Most of the peptide sequences matched the MMG variant GenBank Accession No. NP_001002811 (SEQ ID NO:7), and the last 4 peptides encoded by the cDNA sequence hCG1755149 (FIG. 1E and TABLE 1). In particular, Peptide 13 began with the last 9 residues encoded by the overlapping region of these two cDNA sequences followed by 7 residues present only in hCG1755149. The sequence of immunoprecipitated protein MMG8 is largely similar to NP_001002811 (SEQ ID NO:7), with the exception of the carboxyl tail region.

TABLE 1

Peptides identified from MMG8 by mass spectrometry

| Peptide No. | Sequence |
|---|---|
| P1 | IEALSIER (SEQ ID NO: 27) |
| P2 | IQQTEATNK (SEQ ID NO: 28) |
| P3 | QDGTIQNLK (SEQ ID NO: 29) |
| P4 | ALQQLQEELQNK (SEQ ID NO:30 ) |
| P5 | EQLLQEFRELLQYR (SEQ ID NO: 31) |
| P6 | EQESIIQQLQTSLHDR (SEQ ID NO: 32) |
| P7 | NSELQALR (SEQ ID NO: 33) |
| P8 | QTDQGSMQIPSR (SEQ ID NO: 34) |
| P9 | STLGDLDTVAGLEK (SEQ ID NO: 35) |
| P10 | LTQEVLLLR (SEQ ID NO: 36) |
| P11 | LNEALQAER (SEQ ID NO: 37) |
| P12 | TLQVELEGAQVLR (SEQ ID NO: 38) |
| P13 | LETLAAIGGGELESVR (SEQ ID NO: 39) |

The novel MMG isoform, designated as MMG8, was cloned based on protein sequencing and RT-PCR data. The carboxy-terminal region of MMG8 is different from all other MMG variants. The homolog of MMG8 was detected in *Pongo abelii* (Genbank accession: NP_001126198) (SEQ ID NO: 12) and mouse (Genbank accession: AAI41173) (SEQ ID NO: 13), with overall sequence homologies of 98% and 92%, respectively. MMG8 also exhibits significant homology to *Gallus gallus* XP_423459 (SEQ ID NO: 14), *Xenopus tropicalis* NP_001072886 (SEQ ID NO: 15), and *Danio rerio* CAI11891 (SEQ ID NO: 16) and NP_956195 (SEQ ID NO: 17). MMG8 homologues have been observed in chicken, *Xenopus*, and zebrafish, in addition to mammals, suggesting their conservation in vertebrates. In the cell cultures examined, MMG8 is the major isoform expressed from the human MMG gene, which is multispliced. To date, the other known splice product of human MMG is MMG isoform 1 (Verde et al., *J. Biol. Chem.* 276:11189-11198 (2001)).

A second antibody, 532C, was generated against the carboxy-terminus of MMG8. The 523C and 443M antibodies yielded identical results in immunoprecipitation and immunoblots; unless otherwise specified, the results shown herein were obtained with 532C.

A single protein band of MMG8 was detected on an immunoblot of proliferating epithelial, fibroblast, and neuroblastoma cells (FIG. 1D). In C2C12 myotubes, two smaller protein bands were found beside the ~150 kDa species (FIG. 1D), suggesting the existence of other isoforms or proteolytic products. However, MMG isoform 1, a ~230 kDa species, was not detectable in these cell cultures (FIG. 1D), although it was readily recognized by the antibody in rat heart tissue.

To explore the function of MMG8, RNAi-mediated suppression of MMG8 expression was performed. Two siRNA oligonucleotides were designed to target MMG8. Transfection of either siRNA effectively depleted the protein by ~90% (FIG. 1F). Cells expressing MMG8 showed prominent Golgi localization; whereas cells transfected with MMG8-targeting siRNA exhibited a weak background when labeled with anti-MMG8 antibodies and showed no Golgi localization pattern (FIG. 1G), corroborating the specificity of anti-MMG8 staining. In addition, in cells transfected with MMG8-siRNA, the Golgi ribbons broke into patches that overlapped largely with the nuclei (FIG. 1G). The results showed that MMG8 is required for the Golgi structural organization.

Example 2

Association of MMG8 with AKAP450

To identify proteins that bind to MMG8, MMG8 immunoprecipitation was performed and the immunoprecipitates were analyzed by mass spectrometry. The results show that MMG8 interacts with the regulatory subunit of protein kinase A (PKA) and EB1.

Figure 2:
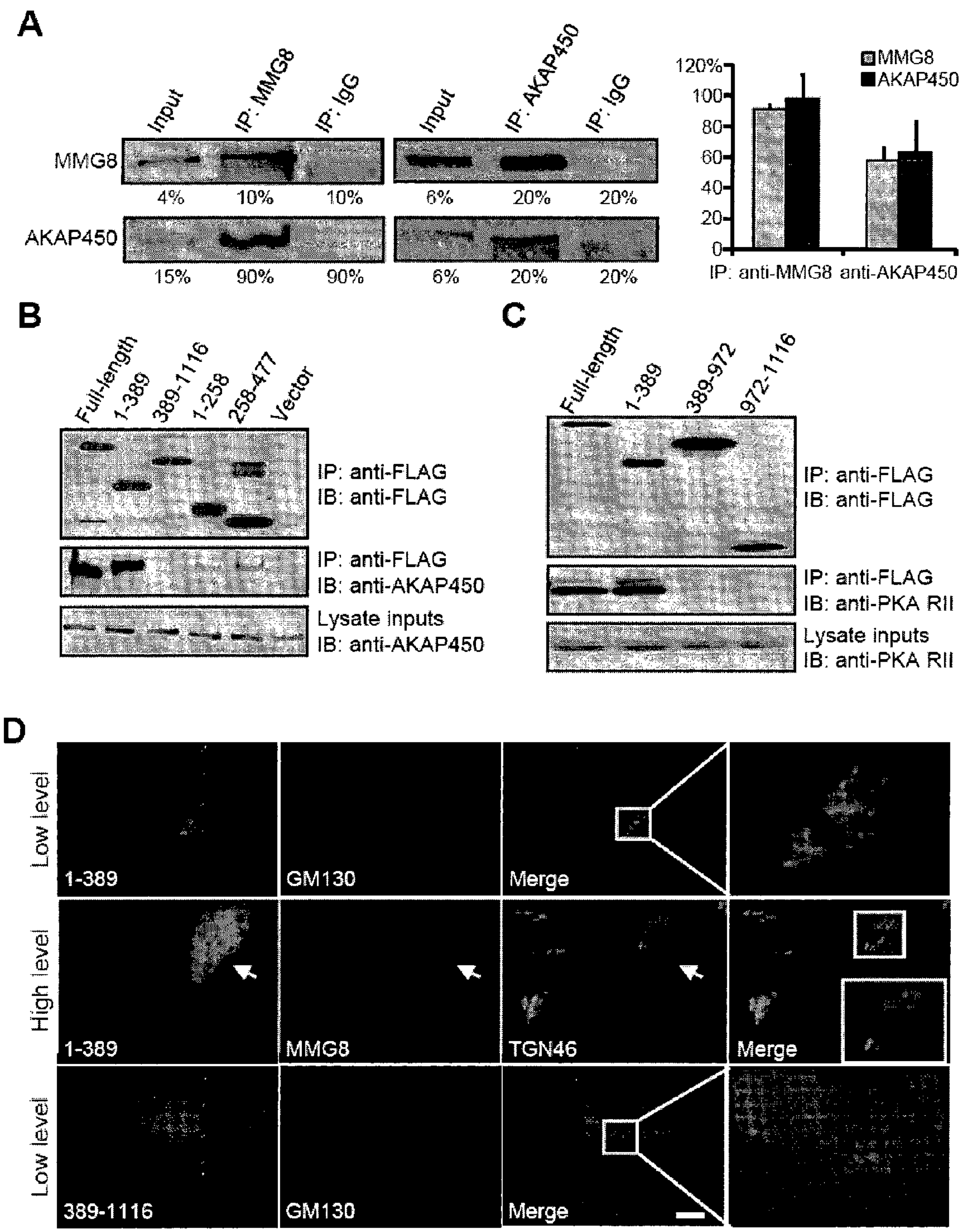
FIG. 2 shows that MMG8 interacts with AKAP450. (A) Anti-MMG8 and anti-AKAP450 immunoprecipitations (IPs) were performed with HeLa extracts. The immunoprecipitated proteins and inputs were analyzed by immunoblotting and quantified. The histogram shows the amount of the precipitated proteins relative to that of the respective inputs. Data shown are means±S.D. from three independent experiments. (B-C) HEK293T cells expressing various MMG8 constructs containing a FLAG tag were subjected to anti-FLAG immunoprecipitation. The immunoprecipitates and inputs were immunoblotted (IB) for the MMG8 fragments (anti-FLAG) and AKAP450 (B) or the RII subunit of protein kinase A (C). (D) MMG8 fragments were transiently expressed in HeLa cells. The cells were stained for endogenous MMG8 and the Golgi markers as labeled. The arrow indicates a transfected cell. Boxed areas are enlarged. Scale bars, 5 μm.

To investigate the interaction between MMG8 and PKA, co-immunoprecipitation of MMG8 and AKAP450 was performed. AKAP450 is a cis-Golgi protein that binds to the regulatory subunit of protein kinase A (Keryer et al., *Exp. Cell Res.* 204:230-240 (1993); Schmidt et al., *J. Biol. Chem.* 274: 3055-3066 (1999); Takahashi et al., *J. Biol. Chem.* 274: 17267-17274 (1999); Witczak et al., *EMBO J.* 18:1858-1868 (1999); Rivero et al., *EMBO J.* 28:1016-1028 (2009)). The reciprocal experiments revealed that MMG8 and AKAP450 co-precipitated each other specifically (FIG. 2A). The immunodepletion of MMG8 almost completely depleted AKAP450 from the HeLa lysates (FIG. 2A). In the reciprocal experiment, anti-AKAP450 immunoprecipitation proportionally co-precipitated MMG8 (FIG. 2A). The quantification of the co-immunoprecipitates revealed that MMG8 and AKAP450 formed a stoichiometric complex in lysates.

To identify the MMG8 domain that interacts with AKAP450, various MMG8 fragments were ectopically expressed for AKAP450 co-immunoprecipitation. The results showed that the head region consisting of amino acids 1-389 was essential for binding with AKAP450; whereas the MMG8 fragment comprising amino acids 390-1116 did not bind to AKAP450 (FIG. 2B). In addition, truncation of 1-389 significantly impaired the AKAP450 binding activity (FIG. 2B). Also, only the fragment that comprises 1-389 of MMG8 binds to protein kinase A (FIG. 2C). The results showed that MMG8 indirectly associates with protein kinase A through AKAP450.

When expressed at low levels, the MMG8 fragment comprising amino acids 1-389 displayed specific Golgi localization (FIG. 2D). When highly expressed, this MMG8 fragment dislodged endogenous MMG8 from the Golgi apparatus (FIG. 2D). In contrast, the expression of 389-1116 did not display any specific pattern (FIG. 2D). The results show that amino acid residues 1-389 serve as the AKAP450-binding and Golgi-targeting domain of MMG8.

Figure 3:
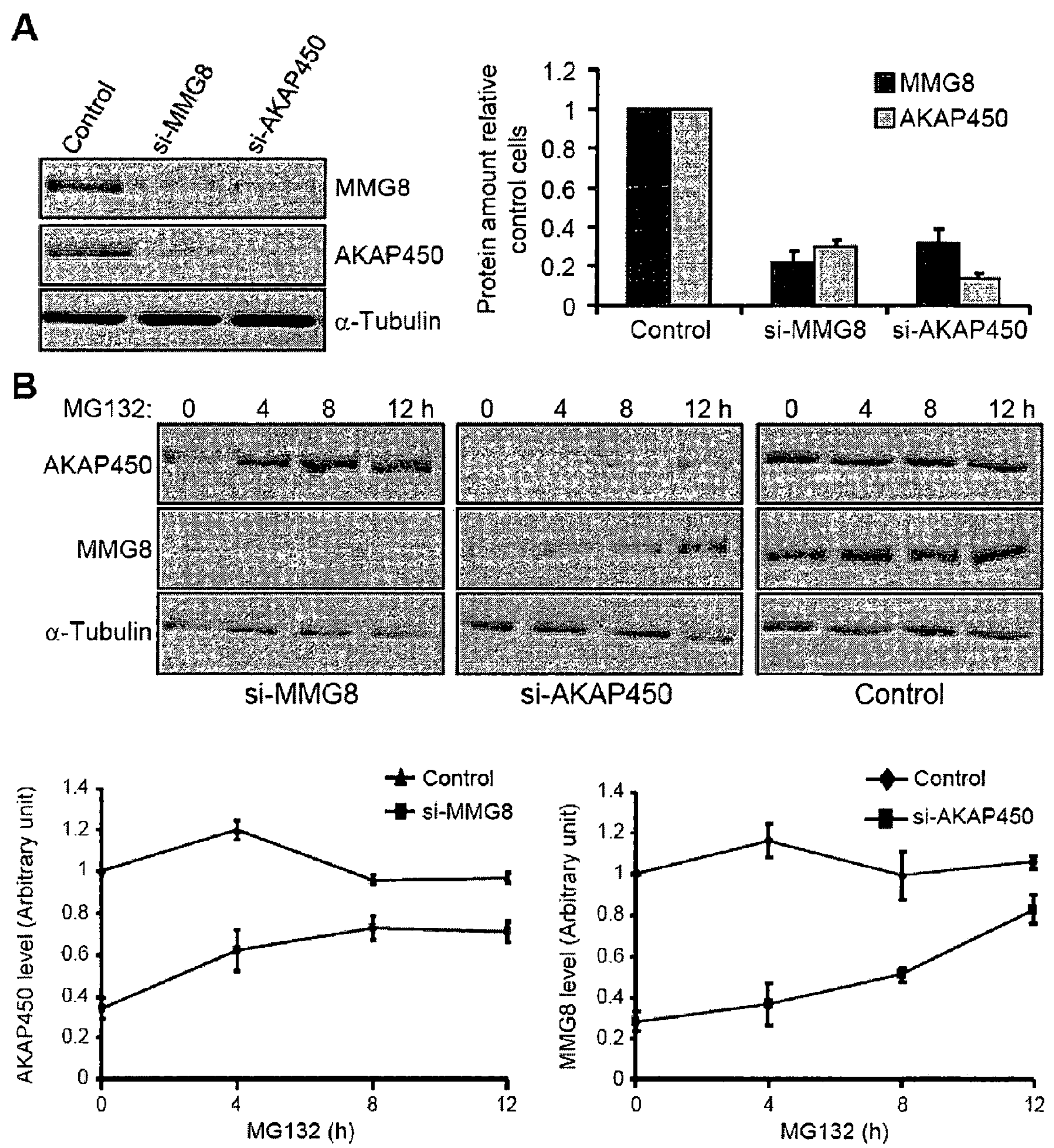
FIG. 3 shows that MMG8 and AKAP450 are mutually dependent for stability. (A) hTERT-RPE1 cells were transfected with siRNAs as labeled. The cell extracts were examined by immunoblotting. After quantification, the amounts of MMG8 and AKAP450 in the siMMG8 or siAKAP450-transfected extracts were expressed as percentages of the respective amounts in the control extracts. Data from three independent experiments are shown. (B) Cells transfected with siRNAs were treated with MG132 at 72 h post-transfection. After treatment, the cells were analyzed on immunoblots for MMG8, AKAP450, and α-tubulin. The amounts of MMG8 and AKAP450 were plotted with quantification data of three independent experiments.

In experiments on RNAi-mediated MMG8 depletion, AKAP450 was probed on immunoblots. The effective suppression of MMG8 expression remarkably reduced the protein level of AKAP450; the reduction of AKAP450 correlated with that of MMG8 (FIG. 3A). Similarly, the amount of MMG8 decreased significantly (by ~65%) when the expression of AKAP450 was suppressed by ~80% using siRNA (FIG. 3A). The results showed that the protein levels of MMG8 and AKAP450 are interrelated.

To investigate whether MMG8 and AKAP450 depend on each other for stability, a proteasome inhibitor, MG132, was applied to cells either depleted of MMG8 or AKAP450. The protein level of AKAP450 in MMG8-depleted cells increased along the time course of MG132 treatment and eventually approached the level in control cells (FIG. 3B). The amount of MMG8 in AKAP450-depleted cells also increased significantly by the MG132 treatment (FIG. 3B). In control-transfected cells, the levels of MMG8 and AKAP450 were not significantly altered by MG132 (FIG. 3B). The results reveal that in the absence of either MMG8 or AKAP450, the remaining protein becomes unstable and is degraded by the proteasome.

Example 3

Effects of MMG80n Microtubule Nucleation at the Golgi Apparatus

This Example assesses whether MMG8 interacts with the γTuCs, which associates with AKAP450—a cis-Golgi protein indispensable for microtubule nucleation at the Golgi apparatus (Rivero et al., EMBO J. 28:1016-1028 (2009); Takahashi et al., *Mol. Biol. Cell* 13:3235-3245 (2002)).

Figure 4:
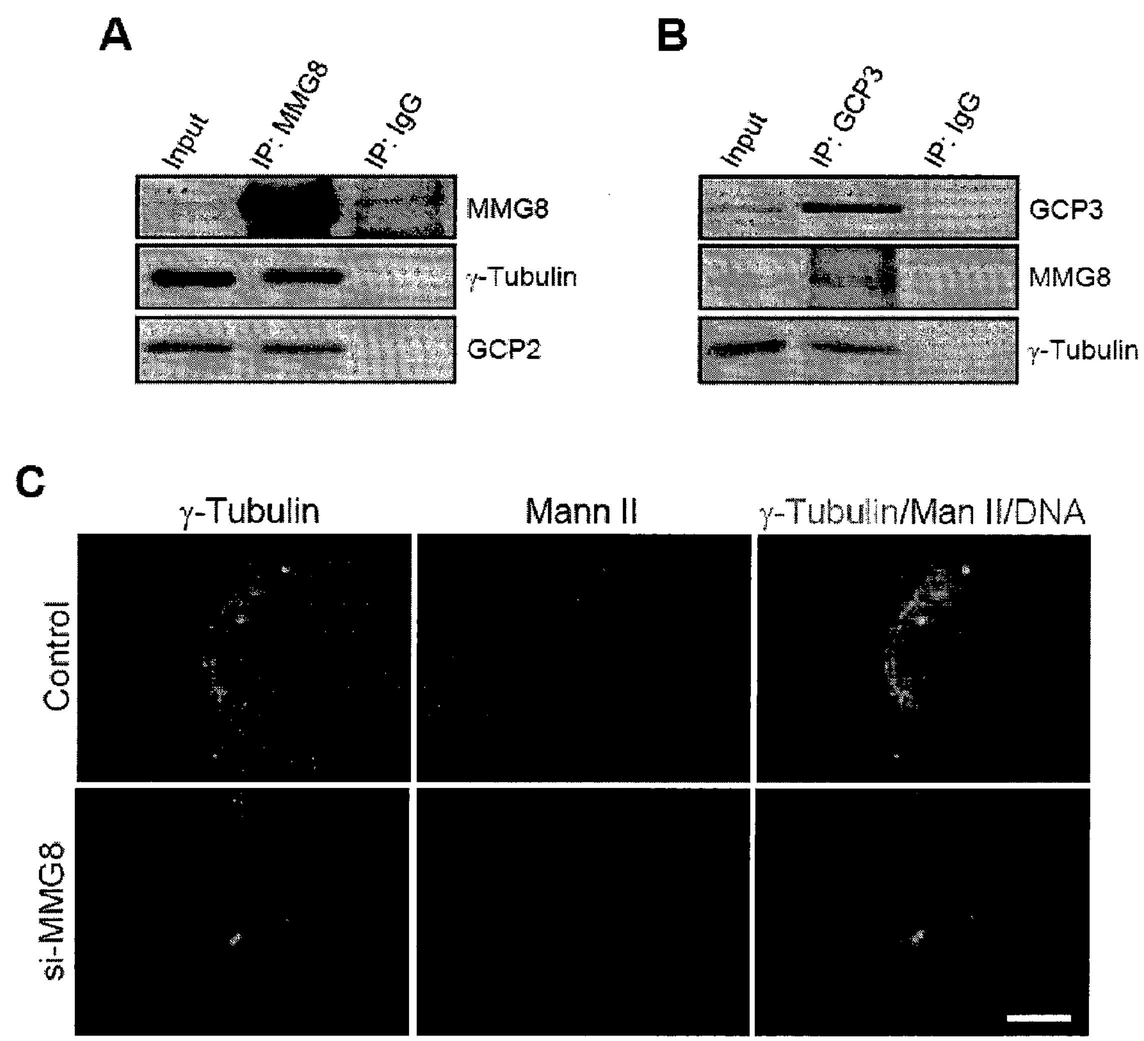
FIG. 4 shows that MMG8 associates with γ-tubulin complexes at the Golgi apparatus. (A-B) anti-MMG8 (A) and anti-GCP3 (B) immunoprecipitations were performed with HeLa extracts. The immunoprecipitates and inputs were examined on immunoblots. (C) Cells transfected with siRNAs were subjected to immunostaining of γ-tubulin and mannosidase II (Man II). Scale bars, 5 μm.

Anti-MMG8 immunoprecipitation co-precipitated γ-tubulin and GCP2 (gamma-tubulin complex protein 2), which are core components of the γTuCs examined (FIG. 4A). In a reciprocal experiment, MMG8 specifically co-precipitated with GCP3 (gamma-tubulin complex protein 3), another core component of γTuCs (FIG. 4B). These results demonstrate that MMG8 associates with γTuCs.

To examine whether the Golgi localization of γTuCs requires MMG8, MMG8 expression was silenced and immunostaining of γ-tubulin was performed. RNAi-mediated depletion of MMG8 eliminated the Golgi attachment of γ-tubulin, without apparently affecting its centrosomal staining (FIG. 4C). The results show that MMG8 is required for the recruitment of γTuCs to the Golgi apparatus, but is not required for the recruitment of γTuCs to centrosomes.

Figure 5:
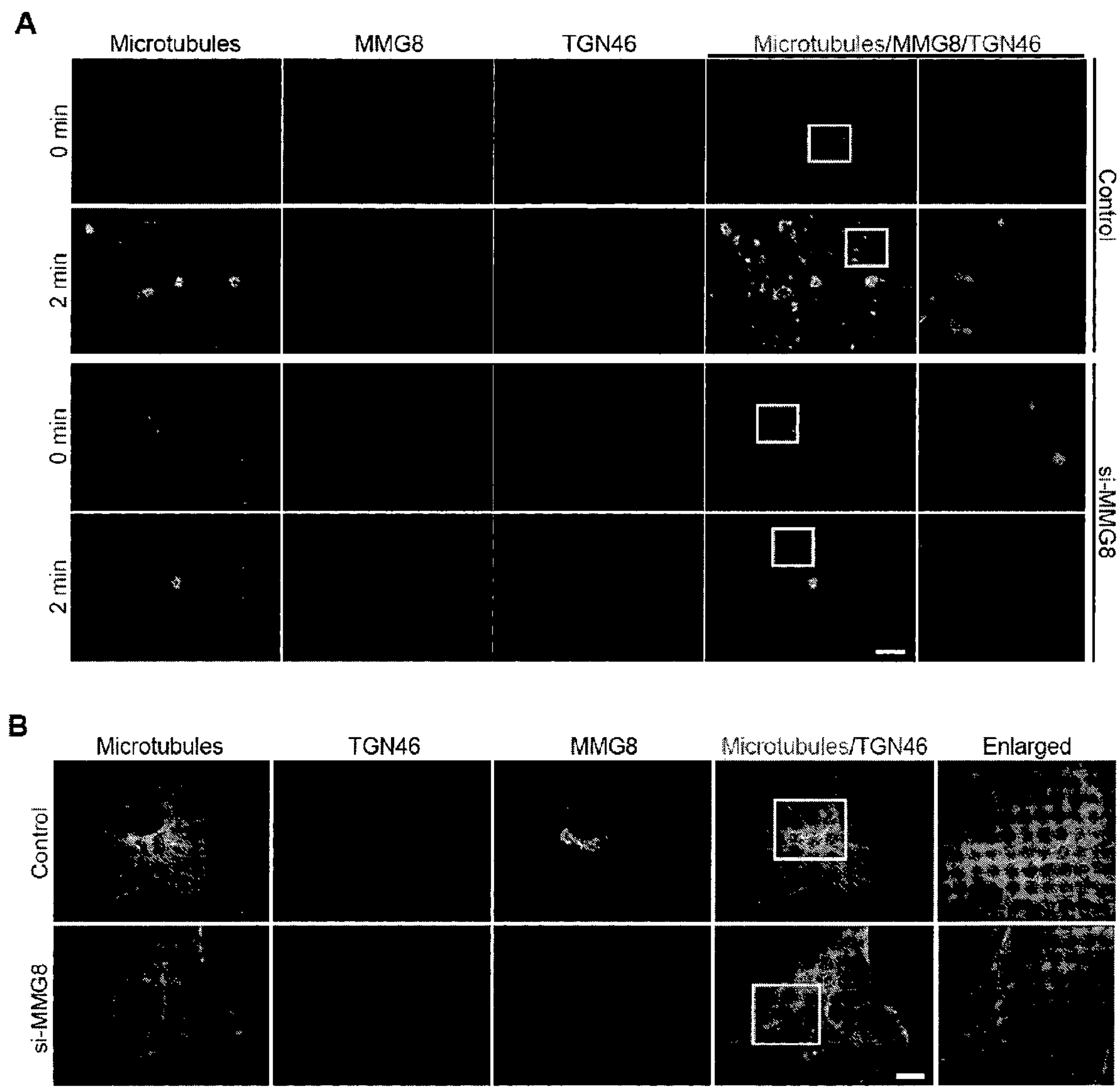
FIG. 5 shows that MMG8 is required for microtubule nucleation at the Golgi apparatus. (A) hTERT-RPE1 cells were transfected with siRNAs. After nocodazole depolymerization of microtubules, microtubule regrowth was initiated by nocodazole washout. The cells were then stained for MMG8, TGN46, and microtubules (anti-α-tubulin). (B) Immunofluorescence micrographs of cells transfected with siRNAs. Boxed areas are enlarged. Scale bars, 5 μm.

This Example also examined the role of MMG8 in microtubule nucleation after nocodazole-induced depolymerization. Prior to the assays, RPE1 cells were transfected with either a control or MMG8-targeting siRNA. In nocodazole-treated control cells, short microtubules appeared at the fragmented Golgi apparatus as well as a centrosomal aster of microtubules 2 min after nocodazole washout (FIG. 5A). In comparison, the MMG8-depleted cells did not exhibit microtubule growth from the Golgi apparatus; the centrosomal regrowth was not discernibly affected by MMG8 depletion (FIG. 5A). The results showed that MMG8 depletion inhibits microtubule nucleation at the Golgi apparatus, but does not affect centrosomal nucleation.

In RPE1 cells, microtubules are focused on the Golgi apparatus and its colocalized centrosomes to form a radial pattern, and the Golgi region harbors a high density of microtubules (FIG. 5B). The suppression of MMG8 expression significantly reduced microtubule density at the Golgi apparatus (FIG. 5B). Also, in MMG8-depleted cells, the microtubules were unfocused on the Golgi region (FIG. 5B). The data further support that MMG8 is required for microtubule growth and organization at the Golgi apparatus.

Example 4

Association of MMG8 with EB1/EB3

The mass spectrometry results showed that MMG8 interacts with EB1. Anti-MMG8 immunoprecipitation was carried out to detect whether MMG8 co-precipitates with endogenous EB1. Immunoblotting of the immunoprecipitates revealed the specific association of EB1 with MMG8 (FIG. 6A).

MMG8 comprises a putative SxIP motif that is a microtubule plus-end-tracking signal associated with EB1/EB3. Within the motif, the Ile/Leu-Pro dipeptide is critical for EB1/EB3 binding (Honnappa et al., *EMBO J.* 24:261-269 (2005)). A mutant MMG8 was constructed, wherein the dipeptide residue Leu311-Pro312 was substituted with two alanines. An MMG8 fragment (i.e., 1-389) that encompasses the SxIP motif (Ser-x-Ile-Pro) and its L311A/P312A mutant were constructed.

Figure 6:
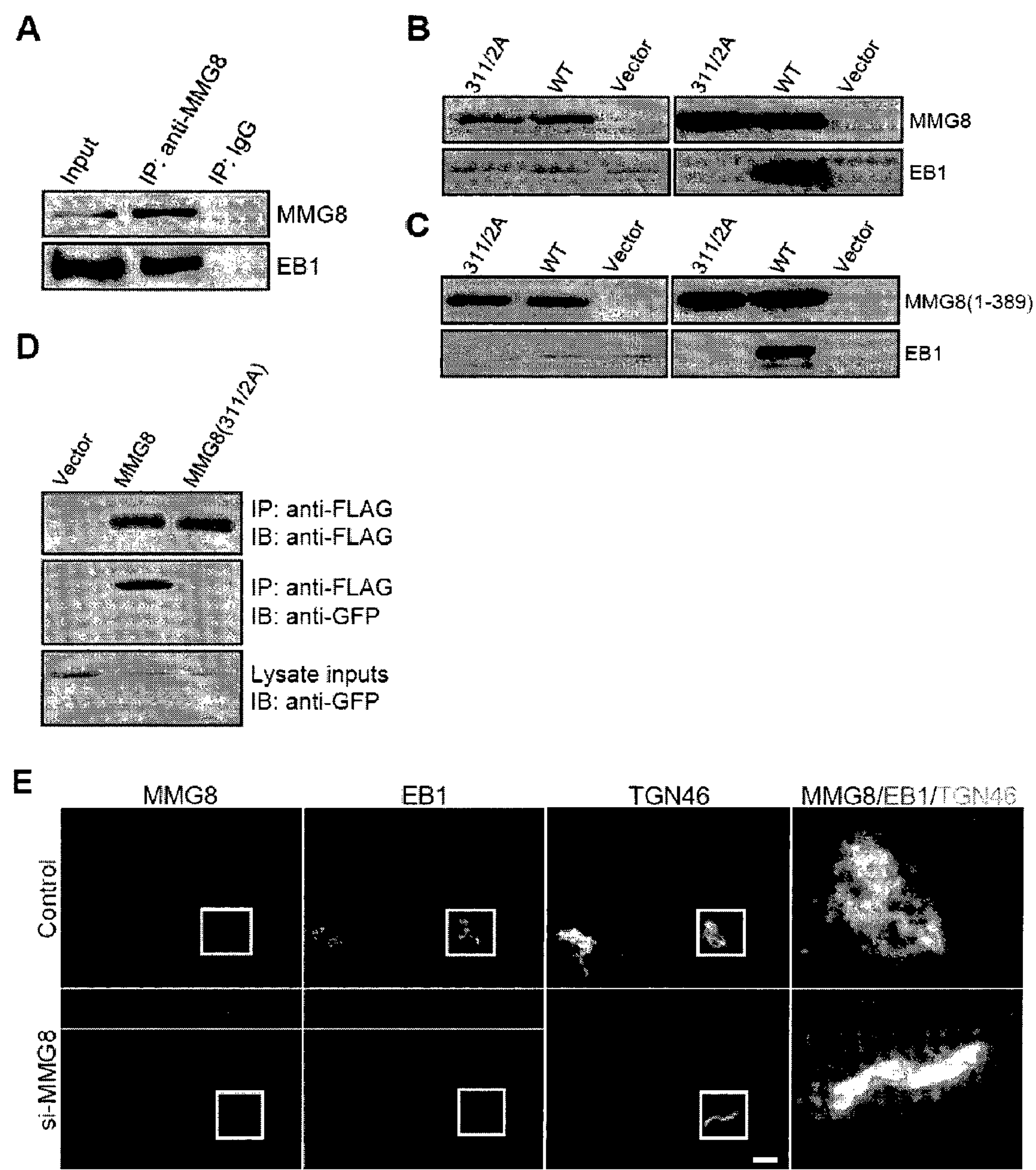
FIG. 6 shows that MMG8 binds to EB1 and EB3, and mediates EB1 recruitment to the Golgi apparatus. (A) Co-immunoprecipitation of EB1 with MMG8. After anti-MMG8 immunoprecipitation, the immunoprecipitates and inputs were examined on immunoblots. (B-C) The full-length MMG8 (B) and its fragment 1-389 (C) were ectopically expressed with a FLAG tag. After anti-FLAG immunoprecipitation, the immunoprecipitates and inputs were probed on immunoblots. WT, MMG8 wild-type; 311/2A, MMG8 (L311A/P312A). (D) HEK293T was double transfected with GFP-EB3 and a FLAG-tagged construct of MMG8 or its L311A/P312A mutant (311/2A). After anti-FLAG immunoprecipitation, the precipitated proteins and inputs were analyzed for EB3 (anti-GFP) and MMG8 (anti-FLAG). Vec, FLAG vector; WT, wild-type MMG8; 311/2A, MMG8 (L311A/P312A) (E) HeLa cells transfected with siRNAs were triple stained for MMG8, EB1, and TGN46. Scale bars, 5 μm.

Fragment 1-389 displayed a similar EB1-binding activity as the full-length protein (FIG. 6, B-C). Unlike the wild-type MMG8, L311A/P312A mutants completely lost the binding activity (FIG. 6, B-C). The data confirmed that the SAP motif of MMG8 is required for binding to EB1.

The Example also examines the interaction between MMG8 and EB3. EB3 was detected in the immunoprecipitates of wild-type MMG8, but not in the immunoprecipitates of the L311A/P312A mutant (FIG. 6D). The results show that the SxIP motif of MMG8 is required for EB3 binding.

EB1 resides in the cytoplasm and associates with microtubules. To visualize whether EB1 localizes at the Golgi apparatus, cells were extracted under a condition to preserve Golgi networks and to remove cytosolic and microtubule-associated proteins. Following extraction, cells were subjected to immunostaining. EB1 displayed Golgi patterns that merged well with the fluorescent signals of MMG8 (FIG. 6E). The RNAi-mediated MMG8 depletion eliminated the Golgi staining of EB1 (FIG. 6E), but did not discernibly affect attachment of EB1 to the growing microtubule tips. The results show that EB1 targets the Golgi apparatus in a manner dependent on its association with MMG8.

To test whether MMG8 associates with microtubules and whether EB1/EB3 is involved in such association, a microtubule binding assay was performed. Briefly, microtubules were pelleted from cell extracts after taxol-induced polymerization. To disrupt the interaction between MMG8 and EB1/EB3, the carboxy-terminal fragment EB1(185-268), which harbors the EBH domain that binds to the SxIP motif (Askham et al., *Mol. Biol. Cell* 13:3627-3645 (2002)), was over-expressed. As a control, the ectopic tag (GFP) was expressed.

Figure 7:
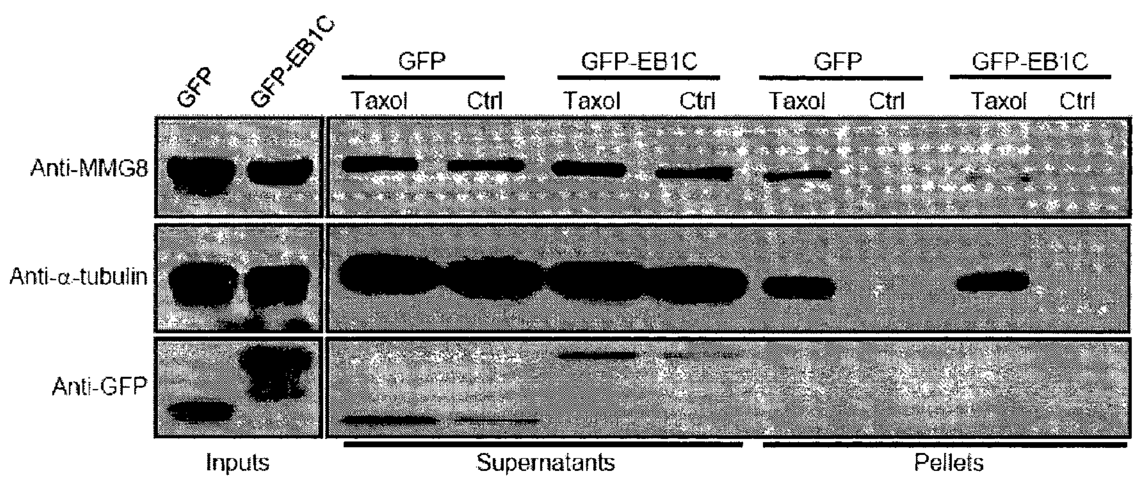
FIG. 7 shows that EB1 mediates the interaction between MMG8 and microtubules. Microtubules were polymerized with taxol in HEK293T extracts expressing GFP or GFP-EB1 (185-268). Taxol was absent in control (Ctrl). After microtubule sedimentation, the supernatants and pellets were probed for MMG8, α-tubulin and the GFP proteins. GFP-EB1C, GFP-EB1(185-268).

The results showed that, in the absence of microtubules, MMG8 did not sediment (FIG. 7). In control cells, MMG8 was readily detected in the microtubule pellet (FIG. 7). The over-expression of the EB1 fragment 185-268 dramatically reduced the co-sedimentation of MMG8 with microtubules (FIG. 7). The results show that MMG8 associates with microtubules by forming a complex with EB1/EB3.

Example 5

MMG8 is Required for Cell Proliferation

Figure 8:
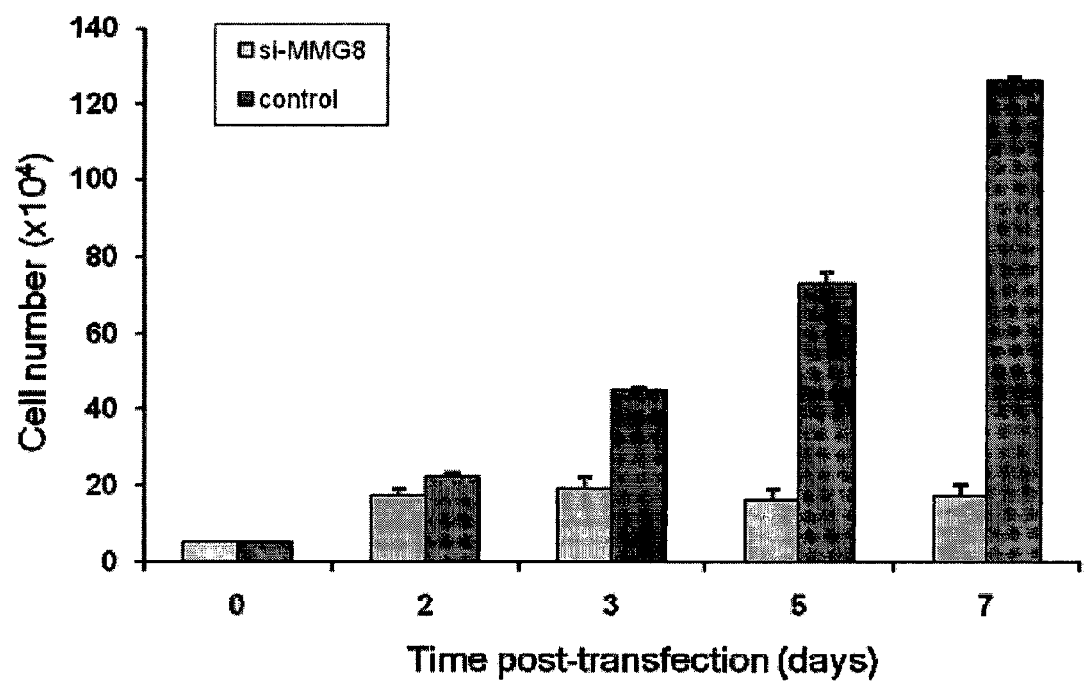
FIG. 8 shows that MMG8 is required for cell proliferation. HeLa cells were transfected with control siRNA or MMG8-targeting siRNA. Cell numbers were counted at various time points.

This Example shows that MMG8 is required for cell proliferation. HeLa cells transfected with control siRNA exhibited normal cell growth (FIG. 8). The disruption of MMG8 expression blocked cell proliferation (FIG. 8). In addition, the expression disruption did not cause significant cell death. Similar results were obtained using the breast cancer line MCF-7. The results show that MMG8 inhibition suppresses cancer cell proliferation and MMG8 can serve as a target for screening of candidate anti-cancer therapeutics.

Example 6

Knockdown of MMG8 Causes Defective Protein Glycosylation

Various membrane-bound or secreted proteins are transported from the ER to the Golgi apparatus, where they undergo post-translational modifications such as glycosylation. This Example investigates the effects of MMG8 on post-translational modification such as glycosylation.

To illustrate, the glycosylation of LAMP-1 and CD44 were examined. LAMP-1 is a lysosomal membrane protein that undergoes two-stage glycosylation: at the ER during synthesis (the first stage) and at the Golgi apparatus (the second stage) (Carlsson et al., *J. Biol. Chem.* 263:18911-18919 (1988)). MMG8-knockdown cells contain both the LAMP-1 precursor and mature LAMP-1 (FIG. 9A), indicating that MMG8-knockdown impaired protein degradation in the lysosome (Meikle et al., *Clin. Chem.* 43:1325-1335 (1997)) that might be resulted from the affected or slowed transport of proteases to the lysosome (Zhu et al., *Mol. Biol. Cell.* 10:537-549 (1999)). Also, the amount of mature LAMP-1 was reduced in MMG8-knockdown cells by ~15% when compared to controls (FIG. 9A), indicating that the ER-to-Golgi transport of LAMP-1 is impaired.

Figure 9:
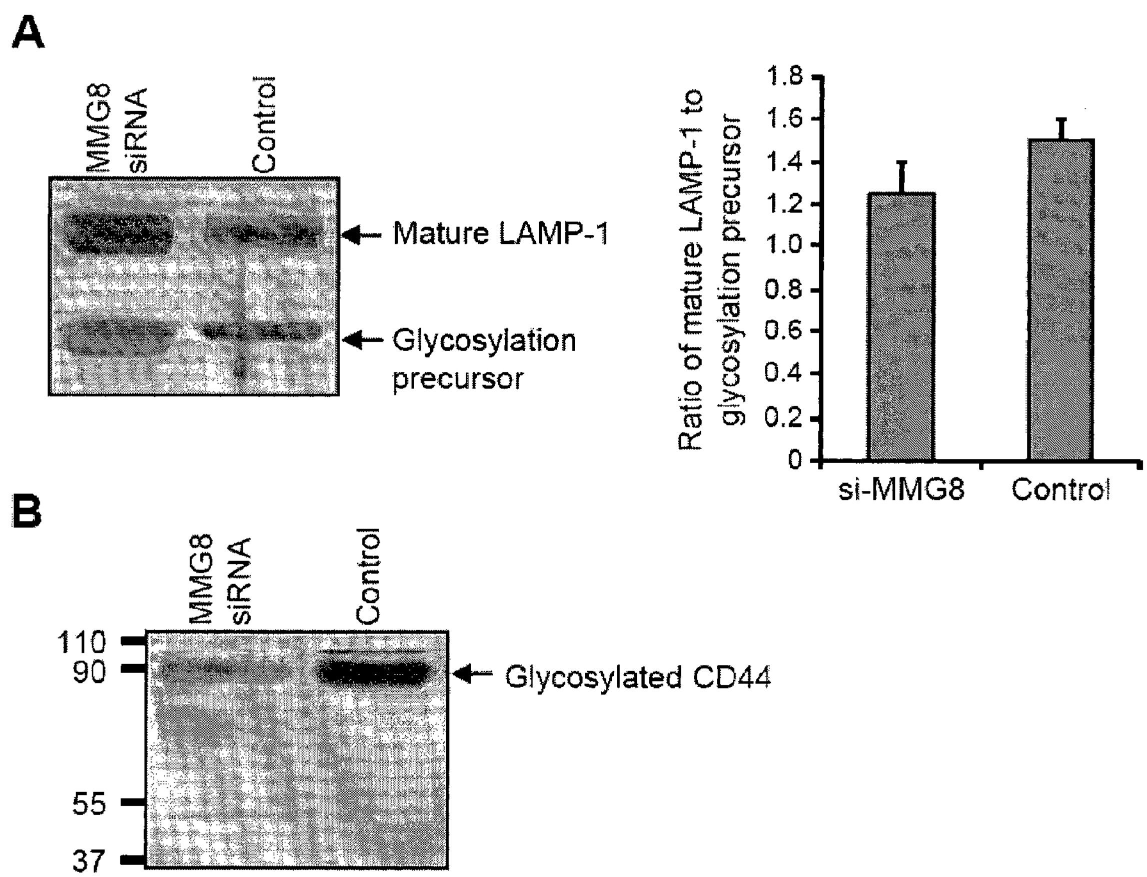
FIG. 9 shows that suppression of MMG8 expression disrupts glycosylation of LAMP-1 and CD44. HeLa cells transfected with control or MMG8 siRNA were analyzed for LAMP-1 and CD44 on immunoblots.

CD44 is a plasma membrane protein that has various species of proteolysis and glycosylation isoforms ranging from ~42 kDa to ~90 kDa (Lokeshwar and Bourguignon, *J. Biol. Chem.* 266:17983-17989 (1991)). In MMG8-depleted cells, fully glycosylated CD44 running at ~90 kDa was significantly reduced (FIG. 9B).

LAMP-1 is a diagnostic marker of lysosomal storage diseases and CD44 has been used as a target for cancer therapy. Therefore, MMG8 can be used for the diagnosis and treatment of lysosomal storage diseases and cancer.

All patents, patent applications, provisional applications, and publications referred to or cited herein are incorporated by reference in their entirety, including all figures and tables, to the extent they are not inconsistent with the explicit teachings of this specification. It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A nucleic acid molecule comprising a cDNA polynucleotide, or a DNA complementary to the full-length of said cDNA polynucleotide, encoding a myomegalin isoform comprising the amino acid sequence of SEQ ID NO:2, or a variant of SEQ ID NO:2 having at least 95% identity to the amino acid sequence of SEQ ID NO:2 and having the ability to promote at least one of microtubule assembly, protein trafficking, and golgi assembly.

2. The nucleic acid molecule of claim 1, comprising a polynucleotide having at least 95% identity to nucleic acids 1-1167 of SEQ ID NO:1, wherein the 3' end of the polynucleotide has at least 95% identity to nucleic acids 3292-3348 of SEQ ID NO:1, or a DNA complement of said polynucleotide.

3. The nucleic acid molecule of claim 1, comprising, of a polynucleotide having at least 95% identity to nucleic acids 1-1167 of SEQ ID NO:1, wherein the 3' end of the polynucleotide has at least 95% identity to nucleic acids 3292-3348 of SEQ ID NO:1, or a DNA complement of said polynucleotide.

4. The nucleic acid molecule of claim 1, wherein the variant of SEQ ID NO:2 has at least 95% identity to the corresponding amino acids 1-389 or 389-1116 or 1098-1116of SEQ ID NO: 2.

5. The nucleic acid molecule of claim 2, comprising the nucleic acid sequence of SEQ ID NO:1.

6. A vector comprising the nucleic acid molecule of claim 1.

7. An isolated host cell comprising the nucleic acid molecule of claim 1.

* * * * *